(12) United States Patent
Jagtap et al.

(10) Patent No.: US 7,863,253 B2
(45) Date of Patent: Jan. 4, 2011

(54) PURINE DERIVATIVES AND METHODS OF USE THEREOF

(75) Inventors: Prakash Jagtap, North Andover, MA (US); Andrew L. Salzman, Belmont, MA (US); Csaba Szabo, Budapest (HU)

(73) Assignee: Inotek Pharmaceuticals Corporation, Lexington, MA (US)

( * ) Notice: Subject to any disclaimer, the term of this patent is extended or adjusted under 35 U.S.C. 154(b) by 838 days.

(21) Appl. No.: 11/230,089

(22) Filed: Sep. 19, 2005

(65) Prior Publication Data

US 2006/0128652 A1 Jun. 15, 2006

Related U.S. Application Data

(60) Provisional application No. 60/611,669, filed on Sep. 20, 2004.

(51) Int. Cl.
 A61K 31/70 (2006.01)
 C07H 19/167 (2006.01)
(52) U.S. Cl. .............. 514/46; 536/27.23; 536/27.63
(58) Field of Classification Search ............ None
 See application file for complete search history.

(56) References Cited

U.S. PATENT DOCUMENTS

| | | | |
|---|---|---|---|
| 3,832,341 A | 8/1974 | Duschinsky | |
| 4,443,836 A | 4/1984 | Horiuchi et al. | |
| 4,968,697 A | 11/1990 | Hutchison | |
| 5,140,015 A | 8/1992 | Olsson et al. | |
| 5,219,840 A | 6/1993 | Gadient et al. | |
| 5,278,150 A | 1/1994 | Olsson et al. | |
| 5,280,015 A | 1/1994 | Jacobson et al. | |
| 5,443,836 A | 8/1995 | Downey et al. | |
| 5,589,467 A | 12/1996 | Lau et al. | |
| 5,789,416 A | 8/1998 | Lum et al. | |
| 6,180,615 B1 | 1/2001 | Zablocki et al. | |
| 6,214,807 B1 | 4/2001 | Zablocki et al. | |
| 6,326,359 B1 | 12/2001 | Monaghan et al. | |
| 6,368,573 B1 | 4/2002 | Leung | |
| 6,403,567 B1 | 6/2002 | Zablocki et al. | |
| 6,426,337 B1 | 7/2002 | Cox et al. | |
| 6,440,948 B1 | 8/2002 | Zablocki et al. | |
| 6,448,236 B1 | 9/2002 | Monaghan | |
| 6,525,032 B2 | 2/2003 | Mantell et al. | |
| 6,528,494 B2 | 3/2003 | Cox et al. | |
| 6,531,457 B2 | 3/2003 | Linden et al. | |
| 6,534,486 B1 | 3/2003 | Allen et al. | |
| 6,638,914 B1 | 10/2003 | Fishman et al. | |
| 6,753,322 B2 | 6/2004 | Mantell et al. | |
| 6,921,753 B2 | 7/2005 | Mantell et al. | |
| 7,238,676 B2 * | 7/2007 | Mantell et al. ........... | 514/46 |
| 2001/0051612 A1 | 12/2001 | Cristalli | |
| 2003/0013675 A1 | 1/2003 | Yeadon et al. | |
| 2003/0055021 A1 | 3/2003 | DeNinno et al. | |
| 2005/0282768 A1 | 12/2005 | Jagtap et al. | |
| 2007/0238694 A1 | 10/2007 | Salzman et al. | |

FOREIGN PATENT DOCUMENTS

| | | |
|---|---|---|
| WO | WO-95/02604 | 1/1995 |
| WO | WO-95/11681 | 5/1995 |
| WO | WO-96/02553 | 2/1996 |
| WO | WO-97/33590 | 9/1997 |
| WO | WO-97/33879 | 9/1997 |
| WO | WO-98/50047 | 11/1998 |
| WO | WO-99/20284 | 4/1999 |
| WO | 99/34804 A1 | 7/1999 |
| WO | WO-01/19360 | 3/2001 |
| WO | WO-02/055085 | 7/2002 |
| WO | WO-02/083152 | 10/2002 |

OTHER PUBLICATIONS

Jagtap, Prakash G. et al., "2-(N-Acyl) and 2-N-acyl-$N^6$-substituted analogues of adenosine and their affinity at the human adenosine receptors," *Bioorganic & Medicinal Chemistry Letters*, vol. 14:1495-1498 (2004).
International Search Report for Application No. PCT/US05/33476, dated Jan. 2, 2008.

(Continued)

*Primary Examiner*—Lawrence E Crane
(74) *Attorney, Agent, or Firm*—Nelson Mullins Riley & Scarborough LLP; Jane E. Remillard; Brian C. Trinque

(57) ABSTRACT

The invention relates to Purine Derivatives; compositions comprising an effective amount of a Purine Derivative; and methods for treating or preventing an ischemic condition, reperfusion injury, a cellular proliferative disorder, a cardiovascular disease, a neurological disorder, a skin disorder, a radiation-induced injury, a wound, or an inflammatory disease comprising administering an effective amount of a Purine Derivative to a subject in need thereof. The Purine Derivatives include compounds of the following formula:

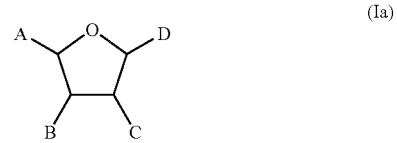

(Ia)

Figure 1:
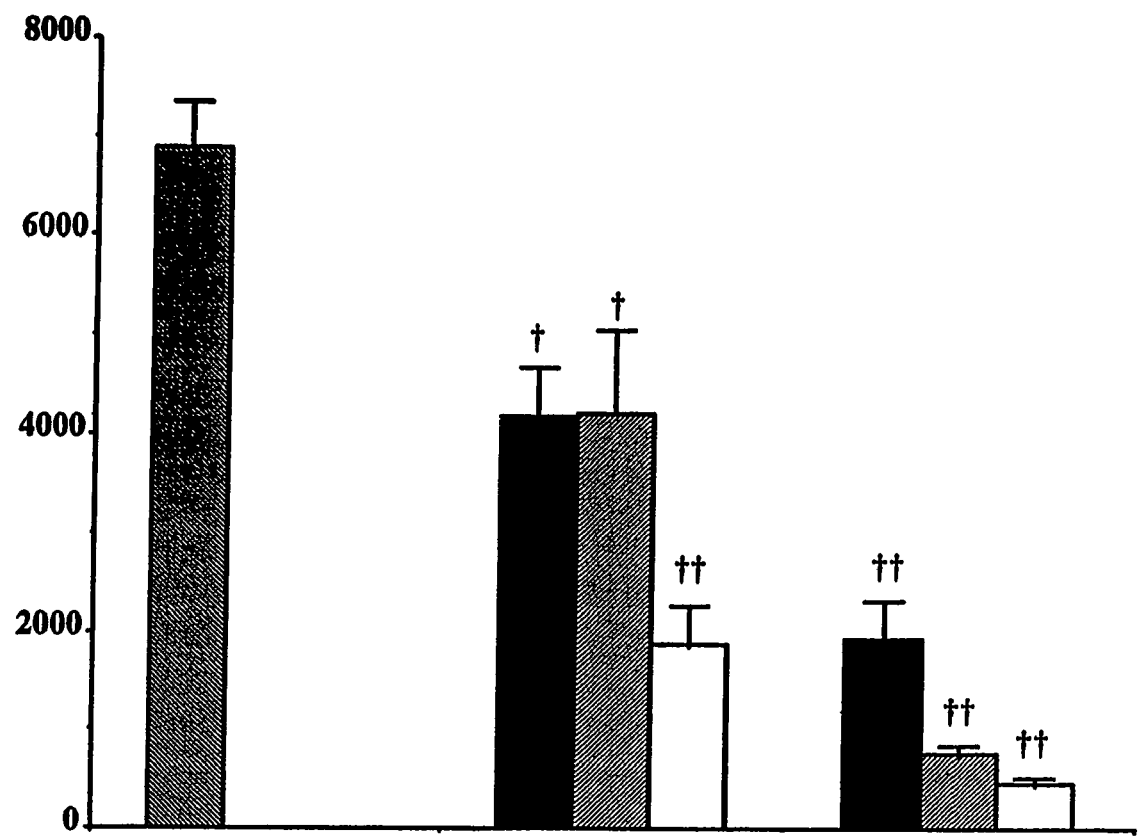

or a pharmaceutically acceptable salt thereof,
wherein
 A is —C(O)$NHR^3$;
 B and C are —OH;
 D is

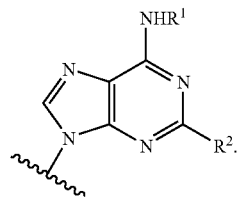

10 Claims, 2 Drawing Sheets

OTHER PUBLICATIONS

Al-Mughales et al., "The chemoattractant activity of rheumatoid synovial fluid for human lymphocytes is due to multiple cytokines." *Clin. Exp. Immunol.*, 1996, vol. 106, pp. 230-236.

Baraldi et al.,"Synthesis and Biological Activity of a New Series of $N^6$-Arylcarbamoyl, 2-(Ar)alkynyl-$N^6$-arylcarbamoyl, and $N^6$-Carboxamido Derivatives of Adenosine-5'-N-ethyluronamide as $A_1$ and $A_3$ Adenosine Receptor Agonists" *J. Med. Chem.*, 1998, vol. 41, pp. 3174-3185.

Beukers et al., "New, Non-Adenosine, High-Potency Agonists for the Human Adenosine $A_{2B}$ Receptor with an Improved Selectivity Profile Compared to the Reference Agonist N-Ethylcarboxamidoadenosine" *J. Med. Chem.*, 2004, vol. 47, pp. 3707-3709.

Beukers, et al., "$N^6$-Cyclopentyl-2-(3-phenylaminocarbonyltriazene-1-yl)adenosine (TCPA), a Very Selective Agonist with High Affinity for the Human Adenosine $A_1$ Receptor."*J. Med. Chem.*, 2003, 46:1492-1503.

Bouma et al. "Differential Regulatory Effects of Adenosine on Cytokine Release by Activated Human Monocytes." *J. Immunol.*, 1994, vol. 153, pp. 4159-4168.

Bradley et al., "Purine Nucleoside-Dependent Inhibition of Cellular Proliferation in 1321N1 Human Astrocytoma Cells." *J. Pharmacol. Expt. Ther.*, 2001, vol. 299, pp. 748-752.

Camaioni, et al., "Adenosine receptor agonists: Synthesis and biological evaluation of the diastereoisomers of 2-(3-hydroxy-3-phenyl-1-propyn-1-yl)NECA." *Bioorg. Med. Chem.*, 1997, 5(12):2267-2275.

Cristalli et al., "2-Alkynyl Derivatives of Adenosine and Adenosine-5'-N-ethyluronamide as Selective Agonists a $A_2$ Adenosine Receptors" *J. Med Chem*, 1992, vol. 35, pp. 2363-2368.

Cristalli et at., "2-Alkynyl Derivatives of Adenosine-5'-N-ethyluronamide: Selective $A_2$ Adenosine Receptor Agonists with Potent Inhibitory Activity on Platelet Aggregation." *J. Med. Chem.*, 1994, vol. 37, pp. 1720-1726.

Cristalli et al., "2-Aralkynyl and 2-Heteroalkynyl Derivatives of Adenosine-5'-N-ethyluronamide as Selective $A_{2a}$ Adenosine Receptor Agonists." *J. Med. Chem.*, 1995, vol. 38, pp. 1462-1472.

Dalpiaz, et al., "Synthesis and Study of 5'-Ester Prodrugs of $N^6$-Cyclopentyladenosine, a Selective A1 Receptor Agonist." *Pharm. Res.*, 2001, 18(4):531-536.

De Lean, et al., "Validation and statistical analysis of a computer modeling method for quantitative analysis of radioligand binding data for mixtures of pharmacological receptor subtypes." *Mol. Pharm.*, 1982, 21:5-16.

DeNinno et al., "3'-Aminoadenosine-5'-uronamides: Discovery of the First Highly Selective Agonist at the Human Adenosine $A_3$ Receptor" *J. Med. Chem.*, 2003, vol. 46, pp. 353-355.

Fisher et al., "Treatment of Septic Shock with the Tumor Necrosis Factor Receptor:Fc Fusion Protein" *N. Engl. J. Med.*, 1996, vol. 334, pp. 1697-1702.

Francis et al., "Highly Selective Adenosine $A_2$ Receptor Agonists in a Series of N-Alkylated 2- Aminoadenosines" *J. Med. Chem.*, 1991, vol. 34, pp. 2570-2579.

Hasko et al. "Adenosine Receptor Agonists Differentially Regulate IL-10, TNF-α, and Nitric Oxide Production in RAW 264.7 Macrophages and in Endotoxemic Mice." *J. Immunol.*, 1996, vol. 157, pp. 4634-4640.

Homma et al., "Nucleosides and Nucleotides. 112. 2-(1-Hexyn-1-yl)adenosine-5'-uronamides: A New Entry of Selective $A_2$ Adenosine Receptor Agonists with Potent Antihypertensive Activity" *J. Med. Chem.*, 1992, vol. 35, pp. 2881-2890.

Hutchison et al., "2-(Arylalkylamino)adenosin-5'-uronamides: A New Class of Highly Selective Adenosine $A_2$ Receptor Ligands" *J. Med. Chem.*, 1990, vol. 33, pp. 1919-1924.

Klotz et al., "Comparative pharmacology of human adenosine receptor subtypes—characterization of stably transfected receptors in CHO cells." *Naunyn-Schmiedeberg's Arch. Pharmacol.*, 1998, vol. 357, pp. 1-9.

Klotz et al., "Photoaffinity Labeling of $A_1$-adenosine Receptors" *J. Biol. Chem.*, 1985, vol. 260, pp. 14659-14664.

Kunkel et al.., "The role of chemokines in inflammatory joint disease" *J. Leukocyte Biol.*, 1996, vol. 59, pp. 6-12.

Lichtenthaler, et al., "Nucleosides, XVIII[1]. Improved Preparation of Nucleoside 5'-Nitrates." *Synthesis*, 1974, 199-201.

Lohse et al., "8-Cyclopentyl-1,3-dipropylxanthine (DPCPX)—a selective high affinity antagonist radioligand for $A_1$ adenosine receptors" *Naunyn-Schmiedeberg's Arch. Pharmacol.*, 1987, vol. 336, pp. 204-210.

Mager et al., "Molecular simulation applied to 2-(N'-alkylidenehydrazino)- and 2-(N'aralkylidenehydrazino)adenosine $A_2$ agonists" *Eur. J. Med. Chem.*, 1995, vol. 30, pp. 15-25.

Matsuda et al., "Nucleosides and Nucleotides. 103. 2-Alkynyladenosines: A Novel Class of Selective Adenosine $A_2$ Receptor Agonists with Potent Antihypertensive Effects." *J.Med. Chem.*, 1992, vol. 35, pp. 241-252.

McWhinney et al., "Activation of adenosine $A_3$ receptors on macrophages inhibits tumor necrosis factor-α" *Eur. J. Pharmacol.*, 1996, vol. 310, pp. 209-216.

Moos, et al., "$N^6$-cycloalkyladenosines. Potent, A1-selective adenosine agonists." *J. Med. Chem.*, 1985, 28(10):1383-1384.

Muller, "Adenosine Receptor Ligands-Recent Developments Part I. Agonists." *Current Medicinal Chemistry*, 2000, vol. 7, pp. 1269-1288.

Nair et al., "Novel, Stable Congeners of the Antiretroviral Compound 2',3'-Dideoxyadenosine." *J. Am. Chem. Soc.*, 1989, vol. 111, pp. 8502-8504.

Niiya et al., "2-(N'-Alkylidenehydrazino)adenosines: Potent and Selective Coronary Vasodilators." *J. Med. Chem.*, 1992, vol. 35, pp. 4557-4561.

Ohno et al., "Modulation of adenosine receptor affinity and intrinsic efficacy in adenine nucleosides substituted at the 2-position." *Bioorg. Med. Chem.*, 2004, vol. 12, pp. 2995-3007.

Ongini et al., "Pharmacology of adenosine $A_{2A}$ receptors."*Trends Pharmacol. Sci.*, 1996, vol. 17, pp. 364-372.

Parmely et al. "Adenosine and a Related Carbocyclic Nucleoside Analogue Selectivity Inhibit Tumor Necrosis Factor-α Production and Protect Mice against Endotoxin Challenge." *J. Immunol.*, 1993, vol. 151, pp. 389-396.

Pitcher, G. M., et al., "Paw withdrawal threshold in the von Frey hair test is influenced by the surface on which the rat stands." *J. Neurosci. Methods*, 1999, 87(2):185-193.

Reinhart et al., "Assessment of the safety and efficacy of the monoclonal anti-tumor necrosis factor antibodyfragment, MAK 195F, in patients with sepsis and septic shock: A multicenter, randomized, placebo-controlled, dose-ranging study." *Crit. Care Med.*, 1996, vol. 24, pp. 733-742.

Reinstein et al., "Suppression of Lipopolysaccharide-stimulated Release of Tumor Necrosis Factor by Adenosine: Evidence for $A_2$ Receptors on Rat Kupffer Cells" *Hepatology*, 1994, vol. 19, pp. 1445-1452.

Riche et al., "High Tumor Necrosis Factor Serum Level is Associated with Increased Survival in Patients with Abdominal Septic Shock: A prospective study in 59 patients." *Surgery*, 1996, vol. 120, pp. 801-807.

Rieger et al., "Design, Synthesis, and Evaluation of Novel $A_{2A}$ Adenosine Receptor Agonists." *J. Med. Chem.*, 2001, vol. 44, pp. 531-539.

Roelen, et al., "$N^6$,C8-Disubstituted Adenosine Derivatives as Partial Agonists for Adenosine $A_1$ Receptors." *J. Med. Chem.*, 1996, 39:1463-1471.

Sajjadi et al., "Inhibition of TNF-α Expression by Adenosine—Role of A3 Adenosine Receptors" *J. Immunol.*, 1996, vol. 156, p. 3435-3442.

Schleef et al., "The Effect of Fibrin on Endothelial Cell Migration *In Vitro.*" *Tissue & Cell*, 1982, vol. 14, pp. 629-636.

Thompson, et al., "Activity of $N^6$-substituted 2-chloroadenosines at $A_1$ and $A_2$ adenosine receptors." *J. Med. Chem.*, 1991, 34:3388-3390.

Van der Wenden, et al., "5'-Substituted Adenosine Analogs as New High-Affinity Partial Agonists for the Adenosine $A_1$ Receptor." *J. Med. Chem.*, 1998, 41:102-108.

Van Tilburg et al. "2,5'-Disubstituted Adenosine Derivatives: Evaluation of Selectivity and Efficacy for the Adenosine $A_1$, $A_{2A}$, and $A_3$ Receptor." *J. Med. Chem.*, 2002, vol. 45, pp. 420-429.

Virag et al., "Effects of poly(ADP-ribose) polymerase Inhibition on inflammatory cell migration in a murine model of asthma." *Med. Sci. Monit.*, 2004, vol. 10, pp. BR77-BR83.

Vitorri et al., "2-Alkenyl and 2-Alkyl Derivatives of Adenosine and Adenosine-5'-*N*-Ethyluronamide: Different Affinity and Selectivity of E- and Z-Diastereomers at $A_{2A}$ Adenosine Receptors." *J. Med. Chem.*, 1996, vol. 39, pp. 4211-4217.

Vittori, et al., "N-Cycloalkyl Derivatives of Adenosine and 1-Deazaadenosine as Agonists and Partial Agonists of the $A_1$ Adenosine Receptor." *J. Med. Chem.*, 2000, 43(2):250-260.

Viziano et al. "2-[*N*'-(3-Arylallylidene)hydrazino]adenosines Showing $A_{2a}$ Adenosine Agonist Properties and Vasodilation Activity." *J. Med. Chem.*, 1995, vol. 38, pp. 3581-3585.

Jagtap, Prakash G. et al., "Synthesis of (R)-3,4-dihydro-2H-pyran-2-carboxaldehyde: application to the synthesis of potent adenosine A2A and A3 receptor agonist," Tetrahedron Letters, vol. 50:2693-2696 (2009).

Supplementary European Search Report for Application No. 0598096.3, dated Jul. 26, 2010.

\* cited by examiner

PURINE DERIVATIVES AND METHODS OF USE THEREOF

This application claims the benefit of U.S. Provisional Application No. 60/611,669, filed Sep. 20, 2004, which is incorporated by reference herein in its entirety.

1. FIELD OF THE INVENTION

The invention relates to Purine Derivatives; compositions comprising an effective amount of a Purine Derivative; and methods for treating or preventing an ischemic condition, reperfusion injury, a cellular proliferative disorder, a cardiovascular disease, a neurological disorder, a skin disorder, a radiation-induced injury, a wound, or an inflammatory disease comprising administering an effective amount of a Purine Derivative to a subject in need thereof.

2. BACKGROUND OF THE INVENTION

Adenosine is a naturally occurring purine nucleoside that is ubiquitous in mammalian cell types. Adenosine exerts its biological effects by interacting with $A_1$, $A_2$ (further subclassified as $A_{2A}$ and $A_{2B}$) and $A_3$ cell surface receptors, which modulate important physiological processes.

The $A_1$ and $A_{2A}$ receptor subtypes are believed to play complementary roles in adenosine's regulation of a cell's energy supply. Adenosine, which is a metabolic product of ATP, diffuses from the cell and locally activates the $A_1$ receptor to decrease the oxygen demand or activates the $A_{2A}$ receptor to increase the oxygen supply, thereby reinstating the balance of energy supply and demand within the tissue. The combined action of $A_1$ and $A_2$ subtypes increases the amount of available oxygen to tissue and protects cells against damage caused by a short-term imbalance of oxygen. One of the important functions of endogenous adenosine is to prevent tissue damage during traumas such as hypoxia, an ischemic condition, hypotension and seizure activity.

In addition, modulation of $A_{2A}$ receptors also regulates coronary vasodilation and $A_{2A}$ agonists are known to down-regulate the production of multiple inflammatory mediators and are beneficial in various animal models of inflammation.

Adenosine is also a neuromodulator, which modulates molecular mechanisms underlying many aspects of physiological brain function by mediating central inhibitory effects. An increase in neurotransmitter release follows traumas such as hypoxia, ischemia and seizures. Neurotransmitters are ultimately responsible for neural degeneration and neural death, which can cause brain damage or death. Adenosine is thought to be an endogenous anticonvulsant agent that inhibits glutamate release from excitory neurons and neuronal firing. Adenosine agonists, therefore, are useful as antiepileptic agents.

Adenosine plays an important role as a cardioprotective agent. Levels of endogenous adenosine increase in response to ischemia and hypoxia and protect cardiac tissue during and after trauma (preconditioning). Adenosine agonists thus are useful as cardioprotective agents.

Adenosine $A_{2B}$ receptors are ubiquitous and regulate multiple biological activities. $A_{2B}$ receptors have been implicated in mast-cell activation, asthma, vasodilation, regulation of cell growth, intestinal function, and modulation of neurosecretion. For example, adenosine binds to $A_{2B}$ receptors on endothelial cells and stimulates angiogenesis. Adenosine also regulates the growth of smooth muscle cell populations in blood vessels and stimulates $A_{2B}$ receptors on mast cells, thus modulating Type I hypersensitivity reactions. In addition, Adenosine stimulates gastrosecretory activity by ligation with $A_{2B}$ in the intestine.

In vitro studies have shown that adenosine receptor agonists promote the migration of endothelial cells and fibroblasts, and adenosine receptor agonists have proven to be useful to treat wounds and promote wound healing.

Adenosine $A_3$ receptors modulate cell proliferation processes. See Bradley et al., J. Pharmacl. Expe.l Ther. 2001, 299:748-52.

International Publication No. WO 95/02604 discloses $A_3$ adenosine receptor agonists and their use as locomotor depressants, hypotensive agents, anxiolytic agents, cerebroprotectants and antiseizure agents. U.S. Pat. No. 5,443,836 to Downey et al., discloses the use of adenosine $A_3$ agonists for preventing ischemic heart damage. International Publication Nos. WO 98/50047 and WO 99/20284 also relate to ischemic protection.

International Publication No. WO 01/19360 discloses the use of $A_3$ agonists to induce G-CSF secretion, induce proliferation or differentiation of bone marrow or white blood cells, treat or prevent leukopenia, treat or prevent toxic side effects of certain drugs, inhibit abnormal cell growth, and treat cancer.

International Publication No. WO 01/083152 discloses the use of adenosine $A_3$ receptor agonists to activate natural killer (NK) cells.

International Publication No. WO 02/055085 discloses the use of adenosine $A_3$ agonists to inhibit viral replication.

For a review of recent developments in the field of adenosine receptor agonists, see C. E. Muller, "Adenosine Receptor Ligands-Recent Developments Part I. Agonists," in *Current Medicinal Chemistry* 2000, 7:1269-1288.

2-(N'-Alkylidenehydrazino)adenosines and their 5'-S-alkyl-5'-thio derivatives are reported in U.S. Pat. No. 5,278, 150 to Olsson et al.; International Publication No. WO 9602553 to Di Ayres; Niiya et al. *J. Med. Chem.* 35:4557-4561 (1992); Niiya et al., *J. Med. Chem.* 35:4562-4566 (1992); Maget et al., *Eur. J. Med. Chem.* 30:15-25 (1995); Viziano et al., *J. Med. Chem.* 38:3581-3585 (1995); and Tilburg et al., *J. Med. Chem.* 45:420-429 (2002).

2-Cyanoadenosine derivatives are reported in Nair et al., *J. Am. Chem. Soc.* 111:8502-8504 (1989) and Ohno et al., *Bioorg. Med. Chem.*, 12:2995-3007 (2004).

2-Cyano-6-substituted purines are disclosed in U.S. Pat. No. 5,219,840 to Gadient et al.; U.S. Pat. No. 6,448,236 to Monaghan; U.S. Pat. No. 6,638,914 to Fishman et al.; U.S. Pat. No. 6,921,753 to Mandell et al.; U.S. Patent Publication No. US 2002/0032168 to Mantell et al.; and U.S. Patent Publication No. US 2002/0058641 to Mantell et al.

2-Aminosubstituted adenosines and their 5'-amide derivatives are reported in Francis et al., *J. Med. Chem.* 34:2570-2579 (1991); Hutchison et al., *J. Med. Chem.* 33:1919-1924 (1990); U.S. Pat. No. 4,968,697 to Hutchison et al.; U.S. Pat. No. 5,280,015 to Jacobsen et al.; and U.S. Pat. No. 6,368,573 to Leung et al.

2-Alkylideneadenosines, 2-Alkyleneadenosines and 5'-carboxamides thereof are reported in Cristalli et al., *J. Med. Chem.* 38:1462-1472 (1995); Cristalli et al., *J. Med. Chem.* 37:1720-1726 (1994); Homma et al., *J. Med. Chem.* 35:2881-2890 (1992); Matsuda et al., *J. Med. Chem.* 35:241-252 (1992); Rieger et al., *J. Med. Chem.* 44:531-539 (2001); Beraldi et al., *J. Med. Chem.* 41:3174-3185 (1998); Vittori et al., *J. Med. Chem.* 39:4211-4217; U.S. Pat. No. 6,531,457 to Linden et al.; and U.S. Pat. No. 6,180,615 to Zablocki et al.

2-Chloro and 5'-substituted adenosines are disclosed in U.S. Pat. No. 5,589,467 to Lau et al.

2-Pyrazole and thiophene derivatives are disclosed in U.S. Pat. No. 6,403,567 to Zablocki et al.; U.S. Pat. No. 6,214,807 to Zablocki et al.; and U.S. Pat. No. 6,440,948 to Zablocki et al.

2-Carboxamides and aminomethyleneadenosine derivatives are disclosed in U.S. Pat. No. 6,525,032 to Mantell et al.; U.S. Patent Publication No. US 2002/0032168 to Mantell et al.; and U.S. Patent Publication No. US 2002/0058641 to Mantell et al.

2-Alkyl and aminoalkyl adenosine are disclosed in U.S. Pat. No. 6,326,359 to Monaghan et al.; U.S. Pat. No. 6,448,236 to Monaghan et al.; and U.S. Patent Publication No. US 2003/0013675 to Yeadon et al.

2-Thioether nucleosides are reported in U.S. Patent Publication No. US 2001/0051612 to Cristalli.

2-Aminoalkyl and 5'-heterocyclic nucleosides are disclosed in U.S. Pat. No. 6,426,337 to Cox et al.; U.S. Pat. No. 6,534,486 to Allen et al.; and U.S. Pat. No. 6,528,494 to Cox et al.

2-Alkoxyadenosines are reported in U.S. Pat. No. 5,140,015 to Olsson et al.

3'-Aminoadenosine derivatives are reported as highly selective $A_3$ agonists in DiNinno et al., *J. Med. Chem.*, 46:353-355, (2003); and U.S. Patent Publication No. 2003/0055021 to DeNinno et al.

Non-adenosine adenosine $A_{2B}$ receptor agonists are reported in Beukers et al., *J. Med. Chem.*, 47:3707-3709 (2004).

The citation of any reference in Section 2 of this application is not an admission that the reference is prior art to this application.

3. SUMMARY OF THE INVENTION

In one embodiment, the invention provides compounds having the Formula (Ia):

(Ia)

and pharmaceutically acceptable salts thereof, wherein
A is —C(O)NHR$^3$;
B and C are —OH;
D is:

A and B are trans with respect to each other;
B and C are cis with respect to each other;
C and D are cis or trans with respect to each other;
R$^1$ is -3- to 7-membered monocyclic heterocycle or –8- to 12-membered bicyclic heterocycle;

R$^2$ is —CN, —NHCOOR$^4$, —NHCONHR$^4$, —NHNHCOR$^4$, —NHNHCONHR$^4$, NHNHCOOR$^4$, —NH—N=C(R$^5$)R$^6$, —NR$^5$—N=C(R$^5$)R$^6$ or —NR$^5$—N(R$^7$)R$^8$;

R$^3$ is —C$_1$-C$_{10}$ alkyl, -aryl, -3- to 7-membered monocyclic heterocycle, -8- to 12-membered bicyclic heterocycle, —C$_3$-C$_8$ monocyclic cycloalkyl, —C$_3$-C$_8$ monocyclic cycloalkenyl, —C$_8$-C$_{12}$ bicyclic cycloalkyl or —C$_8$-C$_{12}$ bicyclic cycloalkenyl;

R$^4$ is —C$_1$-C$_{10}$ alkyl, -aryl, —(CH$_2$)$_n$-aryl, —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$—(3- to 7-membered monocyclic heterocycle) or —(CH$_2$)$_n$—(8- to 12-membered bicyclic heterocycle);

each occurrence of R$^5$ is independently —C$_1$-C$_{10}$ alkyl, -aryl, —(CH$_2$)$_n$-aryl, —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$—(-3- to 7-membered monocyclic heterocycle), —(CH$_2$)$_n$—(-8- to 12-membered bicyclic heterocycle), -phenylene-(C$_2$-C$_{10}$ alkynyl), —(CH$_2$)$_m$-phenylene-(CH$_2$)$_m$COOH, —(CH$_2$)$_m$-phenylene-(CH$_2$)$_m$COO—(C$_1$-C$_{10}$ alkyl), —(CH$_2$)$_m$-phenylene-(CH$_2$)$_m$-(-3- to 7-membered monocyclic heterocycle), or $\geq$(CH$_2$)$_m$-C(O)—(C$_1$-C$_{10}$ alkyl), or R$^5$ and R$^6$, together with the carbon atom to which they are attached, join to form a cyclopentyl, 2-cyclopentenyl, 3-cyclopentenyl, cyclohexyl, 2-cyclohexenyl or 3-cyclohexenyl ring;

R$^6$ is —H, —C$_1$-C$_{10}$ alkyl, -aryl, —(CH$_2$)$_n$-aryl, —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$-(-3- to 7-membered monocyclic heterocycle), —(CH$_2$)$_m$-(-8- to 12-membered bicyclic heterocycle), —(CH$_2$)$_m$-phenylene-(CH$_2$)$_m$-(-3- to 7-membered monocyclic heterocycle), —(CH$_2$)$_m$-phenylene-(CH$_2$)$_m$COOH or —(CH$_2$)$_m$-phenylene-(CH$_2$)$_m$COO—(C$_1$-C$_{10}$ alkyl);

R$^7$ is —C$_1$-C$_{10}$ alkyl, -aryl, —(CH$_2$)$_n$-aryl, —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$-(-3- to 7-membered monocyclic heterocycle), —(CH$_2$)$_n$-(-8- to 12-membered bicyclic heterocycle), —(CH$_2$)$_m$-phenylene-(C$_2$-C$_{10}$ alkynyl), —(CH$_2$)$_m$-phenylene-(CH$_2$)$_m$-(-3- to 7-membered monocyclic heterocycle), —(CH$_2$)$_m$-phenylene-(CH$_2$)$_m$COOH, —(CH$_2$)$_m$-phenylene-(CH$_2$)$_m$COO—(C$_1$-C$_{10}$ alkyl), —(CH$_2$)$_m$—C(O)—(C$_1$-C$_{10}$ alkyl), or R$^7$ and R$^8$, together with the nitrogen atom to which they are attached, join to form a -3- to 7-membered nitrogen-containing monocyclic heterocycle or a -8- to 12-membered nitrogen-containing bicyclic heterocycle;

R$^8$ is C$_1$-C$_{10}$ alkyl, -aryl, —(CH$_2$)$_n$-aryl, —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$-(-3- to 7-membered monocyclic heterocycle), —(CH$_2$)$_n$-(-8- to 12-membered bicyclic heterocycle), —(CH$_2$)$_m$-phenylene-(C$_2$-C$_{10}$ alkynyl), —(CH$_2$)$_m$-phenylene-(CH$_2$)$_m$COOH, —(CH$_2$)$_m$-phenylene-(CH$_2$)$_m$COO—(C$_1$-C$_{10}$ alkyl), or —(CH$_2$)$_m$—C(O)—(C$_1$-C$_{10}$ alkyl);

In another embodiment, the invention provides compounds having the Formula (Ib):

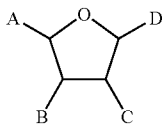

(Ib)

and pharmaceutically acceptable salts thereof, wherein
A is —C(O)NHR$^3$;
B and C are —OH;
D is

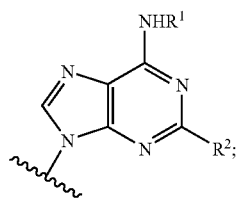

A and B are trans with respect to each other;
B and C are cis with respect to each other;
C and D are cis or trans with respect to each other;
R$^1$ is —H, —C$_1$-C$_{10}$ alkyl, -aryl, —C$_3$-C$_8$ monocyclic cycloalkyl, —C$_3$-C$_8$ monocyclic cycloalkenyl, —C$_8$-C$_{12}$ bicyclic cycloalkyl, —C$_8$-C$_{12}$ bicyclic cycloalkenyl, or —(CH$_2$)$_n$-aryl;
R$^2$ is —NHCOOR$^4$, —NHCONHR$^4$, —NHNHCOR$^4$, —NHNHCONHR$^4$, —NHNHCOOR$^4$, —NH—N=C(R$^9$)R$^{10}$, —NR$^5$—N=C(R$^5$)R$^6$ or —NR$^5$—N(R$^7$)R$^8$;
R$^3$ is —C$_1$-C$_{10}$ alkyl, -aryl or -3- to 7-membered monocyclic heterocycle;
R$^4$ is —C$_1$-C$_{10}$ alkyl, -aryl, —(CH$_2$)$_n$-aryl, —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl)$_n$—(CH$_2$)$_n$—(C$_8$-C$_{12}$ bicyclic cycloalkenyl), —(CH$_2$)$_n$-(-3- to 7-membered monocyclic heterocycle) or —(CH$_2$)$_n$-(-8- to 12-membered bicyclic heterocycle);
each occurrence of R$^5$ is independently —C$_1$-C$_{10}$ alkyl, —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$-(-3- to 7-membered monocyclic heterocycle), —(CH$_2$)$_n$-(-8- to 12-membered bicyclic heterocycle), -phenylene-(C$_2$-C$_{10}$ alkynyl), -phenylene-(CH$_2$)$_m$COOH, -phenylene-(CH$_2$)$_m$-(-3- to 7-membered monocyclic heterocycle), -phenylene-(CH$_2$)$_m$COO—(C$_1$-C$_{10}$ alkyl) or —C(O)—(C$_1$-C$_{10}$ alkyl), or R$^5$ and R$^6$, together with the carbon atom to which they are attached, join to form a cyclopentyl, 2-cyclopentenyl, 3-cyclopentenyl, cyclohexyl, 2-cyclohexenyl or 3-cyclohexenyl ring;
R$^6$ is —H, —C$_1$-C$_{10}$ alkyl, —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$-(-3- to 7-membered monocyclic heterocycle), —(CH$_2$)$_n$-(-8- to 12-membered bicyclic heterocycle), -phenylene-(C$_2$-C$_{10}$ alkynyl), phenylene-(CH$_2$)$_m$COOH, -phenylene-(CH$_2$)$_n$-(-3- to 7-membered monocyclic heterocycle), or -phenylene-(CH$_2$)$_m$COO—(C$_1$-C$_{10}$ alkyl);
R$^7$ is —C$_1$-C$_{10}$ alkyl, -aryl, —(CH$_2$)$_n$-aryl, -(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$-(-3- to 7-membered monocyclic heterocycle), —(CH$_2$)$_n$-(-8- to 12-membered bicyclic heterocycle), -phenylene-(C$_2$-C$_{10}$ alkynyl), -phenylene-(CH$_2$)$_m$COOH, -phenylene-(CH$_2$)$_m$-(-3- to 7-membered monocyclic heterocycle), -phenylene-(CH$_2$)$_m$COO—(C$_1$-C$_{10}$ alkyl) or —C(O)—(C$_1$-C$_{10}$ alkyl), or R$^7$ and R$^8$, together with the nitrogen atom to which they are attached, join to form a -3- to 7-membered nitrogen-containing monocyclic heterocycle or a -8- to 12-membered nitrogen-containing bicyclic heterocycle;
R$^8$ is —C$_1$-C$_{10}$ alkyl, -aryl, —(CH$_2$)$_n$-aryl, —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$-(-3- to 7-membered monocyclic heterocycle), —(CH$_2$)$_n$-(-8- to 12-membered bicyclic heterocycle), -phenylene-(C$_2$-C$_{10}$ alkynyl), -phenylene-(CH$_2$)$_m$COOH, -phenylene-(CH$_2$)$_m$-(-3- to 7-membered monocyclic heterocycle), -phenylene-(CH$_2$)$_m$COO—(C$_1$-C$_{10}$ alkyl) or —C(O)—(C$_1$-C$_{10}$ alkyl);
R$^9$ is —C$_1$-C$_{10}$ alkyl, —(CH$_2$)$_p$—(C$_3$-C$_8$ monocyclic cycloalkenyl), —(CH$_2$)$_p$—(C$_8$-C$_{12}$ bicyclic cycloalkyl), —(CH$_2$)$_p$—(C$_8$-C$_{12}$ bicyclic cycloalkenyl), —(CH$_2$)$_p$-(-3- to 7-membered monocyclic heterocycle), —(CH$_2$)$_p$-(-8- to 12-membered bicyclic heterocycle), -phenylene-(C$_2$-C$_{10}$ alkynyl), -phenylene-(CH$_2$)$_m$COOH, -phenylene-(CH$_2$)$_m$-(-3- to 7-membered monocyclic heterocycle), -phenylene-(CH$_2$)$_m$COO—(C$_1$-C$_{10}$ alkyl), —C(O)-phenyl or —C(O)—(C$_1$-C$_{10}$ alkyl), or R$^9$ and R$^{10}$, together with the carbon atom to which they are attached, join to form a cyclopentyl, 2-cyclopentenyl, 3-cyclopentenyl, cyclohexyl, 2-cyclohexenyl, 3-cyclohexenyl or 1,2,3,4-tetrahydronaphthalene group;
R$^{10}$ is —H, —C$_1$-C$_{10}$ alkyl, —(CH$_2$)$_p$—(C$_3$-C$_8$ monocyclic cycloalkenyl), —(CH$_2$)$_p$—(C$_8$-C$_{12}$ bicyclic cycloalkyl), —(CH$_2$)$_p$—(C$_8$-C$_{12}$ bicyclic cycloalkenyl), —(CH$_2$)$_p$-(-3- to 7-membered monocyclic heterocycle), —(CH$_2$)$_p$-(-8- to 12-membered bicyclic heterocycle), -phenylene-(C$_2$-C$_{10}$ alkynyl), —(CH$_2$)$_m$-phenylene-(CH$_2$)$_m$COOH, -phenylene-(CH$_2$)$_m$-(-3- to 7-membered monocyclic heterocycle) or —(CH$_2$)$_m$-phenylene-(CH$_2$)$_m$COO—(C$_1$-C$_{10}$ alkyl);

each m is independently an integer ranging from 1 to 4;
each n is independently an integer ranging from 1 to 5; and
each p is independently an integer ranging from 0 to 5.

In still another embodiment, the invention provides compounds having the Formula (Ic):

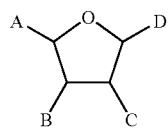

(Ic)

and pharmaceutically acceptable salts thereof, wherein
A is —C(O)NHR³;
B and C are —OH;
D is

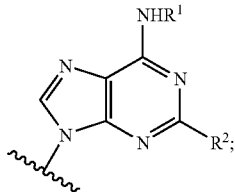

A and B are trans with respect to each other;
B and C are cis with respect to each other;
C and D are cis or trans with respect to each other;
R¹ is —H, —$C_1$-$C_{10}$ alkyl, -aryl, —$C_3$-$C_8$ monocyclic cycloalkyl, —$C_3$-$C_8$ monocyclic cycloalkenyl, —$C_8$-$C_{12}$ bicyclic cycloalkyl, —$C_8$-$C_{12}$ bicyclic cycloalkenyl, or —$(CH_2)_n$-aryl;
R² is —CN, —NHCOOR⁴, —NHCONHR⁴, —NHNHCOR⁴, —NHNHCONHR⁴, —NHNHCOOR⁴, —NR⁵—N=C(R⁵)R or —NR⁵—N(R⁷)R⁸;
R³ is —$C_3$-$C_8$ monocyclic cycloalkenyl, —$C_8$-$C_{12}$ bicyclic cycloalkyl, —$C_8$-$C_{12}$ bicyclic cycloalkenyl, -3- to 7-membered monocyclic heterocycle or -8- to 12-membered bicyclic heterocycle;
R⁴ is —$C_1$-$C_{10}$ alkyl, -aryl, —$(CH_2)_n$-aryl, —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), —$(CH_2)_n$-(-3- to 7-membered monocyclic heterocycle) or —$(CH_2)_n$-(-8- to 12-membered bicyclic heterocycle);
each occurrence of R⁵ is independently —$C_1$-$C_{10}$ alkyl, -aryl, —$(CH_2)_n$-aryl, —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), —$(CH_2)_n$-(-3- to 7-membered monocyclic heterocycle), —$(CH_2)_n$-(-8- to 12-membered bicyclic heterocycle), —$(CH_2)_m$-phenylene-($C_2$-$C_{10}$ alkynyl), —$(CH_2)_m$-phenylene-$(CH_2)_m$COOH, —$(CH_2)_m$-phenylene-$(CH_2)_m$-(-3- to 7-membered monocyclic heterocycle), —$(CH_2)_m$-phenylene-$(CH_2)_m$COO—($C_1$-$C_{10}$ alkyl) or —$(CH_2)_m$—C(O)—($C_1$-$C_{10}$ alkyl), or R⁵ and R⁶, together with the carbon atom to which they are attached, join to form a cyclopentyl, 2-cyclopentenyl, 3-cyclopentenyl, cyclohexyl, 2-cyclohexenyl or 3-cyclohexenyl ring;
R⁶ is —H, —$C_1$-$C_{10}$ alkyl, -aryl, —$(CH_2)_n$-aryl, —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), —$(CH_2)_n$-(-3- to 7-membered monocyclic heterocycle), —$(CH_2)_n$-(-8- to 12-membered bicyclic heterocycle), -phenylene-($C_2$-$C_{10}$ alkynyl), -phenylene-$(CH_2)_m$COOH, -phenylene-$(CH_2)_m$-(-3- to 7-membered monocyclic heterocycle) or -phenylene-$(CH_2)_m$COO—(COO—($C_1$-$C_{10}$ alkyl);
R⁷ is —$C_1$-$C_{10}$ alkyl, -aryl, —$(CH_2)_n$-aryl, —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), —$(CH_2)_n$-(-3- to 7-membered monocyclic heterocycle), —$(CH_2)_n$-(-8- to 12-membered bicyclic heterocycle-$(CH_2)_m$-phenylene-($C_2$-$C_{10}$ alkynyl), —$(CH_2)_m$-phenylene-$(CH_2)_m$COOH, —$(CH_2)_m$-phenylene-$(CH_2)_m$-(-3- to 7-membered monocyclic heterocycle), —$(CH_2)_m$-phenylene-$(CH_2)_m$COO—($C_1$-$C_{10}$ alkyl) or —$(CH_2)_m$—C(O)—($C_1$-$C_{10}$ alkyl), or R⁷ and R⁸, together with the nitrogen atom to which they are attached, join to form a a -3- to 7-membered nitrogen-containing monocyclic heterocycle or a -8- to 12-membered nitrogen-containing bicyclic heterocycle;
R⁸ is —$C_1$-$C_{10}$ alkyl, -aryl, —$(CH_2)_n$-aryl, —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), —$(CH_2)_n$-(-3- to 7-membered monocyclic heterocycle), —$(CH_2)_n$-(-8- to 12-membered bicyclic heterocycle), -phenylene-($C_2$-$C_{10}$ alkynyl), -phenylene-$(CH_2)_m$COOH, -phenylene-$(CH_2)_m$-(-3- to 7-membered monocyclic heterocycle), -phenylene-$(CH_2)_m$COO—($C_1$-$C_{10}$ alkyl) or —C(O)—($C_1$-$C_{10}$ alkyl);
each m is independently an integer ranging from 0 to 4; and
each n is independently an integer ranging from 1 to 5.

In a further embodiment, the invention provides compounds having the Formula (Id):

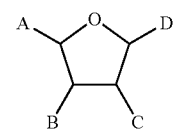

(Id)

and pharmaceutically acceptable salts thereof,
wherein
A is —C(O)NHR³;
B and C are —OH;
D is

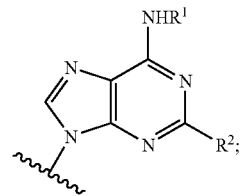

A and B are trans with respect to each other;
B and C are cis with respect to each other;
C and D are cis or trans with respect to each other;
R¹ is —H, —$C_1$-$C_{10}$ alkyl, -aryl, -3- to 7-membered monocyclic heterocycle, -8- to 12-membered bicyclic heterocycle, —$C_3$-$C_8$ monocyclic cycloalkyl, —$C_3$-$C_8$ monocyclic cycloalkenyl, —$C_8$-$C_{12}$ bicyclic cycloalkyl, —$C_8$-$C_{12}$ bicyclic cycloalkenyl, or —$(CH_2)_n$-aryl;
R² is —CN, —NHCOOR⁴, —NHCONHR⁴, —NHNHCOR⁴, —NHNHCONHR⁴, NHNHCOOR⁴, —NH—N=C(R⁵)R⁶, —NR⁵—N=C(R⁵)R⁶or —NR⁵—N(R⁷)R⁸;
R³ is —$C_{13}$-$C_{10}$ alkyl, -aryl, -3- to 7-membered monocyclic heterocycle, -8- to 12-membered bicyclic heterocycle, —$C_3$-$C_8$ monocyclic cycloalkyl, —$C_3$-$C_8$ monocyclic cycloalkenyl, —$C_8$-$C_{12}$ bicyclic cycloalkyl or —$C_8$-$C_{12}$ bicyclic cycloalkenyl;
R⁴ is —$C_1$-$C_{10}$ alkyl, -aryl, —$(CH_2)_n$-aryl, —$(CH_2)_n$—($C_3$-$C_8$ monocyclic cycloalkyl), —$(CH_2)_n$—($C_3$-$C_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$-(-3- to 7-membered monocyclic heterocycle) or —(CH$_2$)$_n$-(-8- to 12-membered bicyclic heterocycle);

each occurrence of R$^5$ is independently —C$_1$-C$_{10}$ alkyl, -aryl, —(CH$_2$)$_n$-aryl, —(CH$_2$)$_n$—(C$_3$-C$_8$ monocyclic cycloalkyl), —(CH$_2$)$_m$—(C$_3$-C$_8$ monocyclic cycloalkenyl), —(CH$_2$)$_m$—(C$_8$-C$_{12}$ bicyclic cycloalkyl), —(CH$_2$)$_m$—(C$_8$-C$_{12}$ bicyclic cycloalkenyl), —(CH$_2$)$_m$-(-3- to 7-membered monocyclic heterocycle), —(CH$_2$)$_m$-(-8- to 12-membered bicyclic heterocycle), -phenylene-(C$_2$-C$_{10}$ alkynyl), -phenylene-(CH$_2$)$_m$COOH, -phenylene-(CH$_2$)$_m$-(-3- to 7-membered monocyclic heterocycle), -phenylene-(CH$_2$)$_m$COO—(C$_1$-C$_{10}$ alkyl) or —C(O)—(C$_1$-C$_{10}$ alkyl), or R$^5$ and R$^{6,}$ together with the carbon atom to which they are attached, join to form a cyclopentyl, 2-cyclopentenyl, 3-cyclopentenyl, cyclohexyl, 2-cyclohexenyl or 3-cyclohexenyl ring;

R$^6$ is —H, —C$_1$-C$_{10}$ alkyl, -aryl, —(CH$_2$)$_n$-aryl, —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$-(-3- to 7-membered monocyclic heterocycle), —(CH$_2$)$_n$-(-8- to 12-membered bicyclic heterocycle), -phenylene-(C$_2$-C$_{10}$ alkynyl), -phenylene-(CH$_2$)$_m$COOH, -phenylene-(CH$_2$)$_m$-(-3- to 7-membered monocyclic heterocycle) or -phenylene-(CH$_2$)$_m$COO—(C$_1$-C$_{10}$ alkyl);

R$^7$ is —C$_1$-C$_{10}$ alkyl, -aryl, —(CH$_2$)$_n$-aryl, —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$-(-3- to 7-membered monocyclic heterocycle), —(CH$_2$)$_n$-(-8- to 12-membered bicyclic heterocycle), -phenylene-(C$_2$-C$_{10}$ alkynyl), —(CH$_2$)$_m$-phenylene-(CH$_2$)$_m$COOH, -phenylene-(CH$_2$)$_m$-(-3- to 7-membered monocyclic heterocycle), -phenylene-(CH$_2$)$_m$COO—(C$_1$-C$_{10}$ alkyl) or —C(O)—(C$_1$-C$_{10}$ alkyl), or R$^7$ and R$^8$, together with the nitrogen atom to which they are attached, join to form a -3- to 7-membered nitrogen-containing monocyclic heterocycle or a -8- to 12-membered nitrogen-containing bicyclic heterocycle;

R$^8$ is —C$_1$-C$_{10}$ alkyl, -aryl, —(CH$_2$)$_n$-aryl, —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_1$-(-3- to 7-membered monocyclic heterocycle), —(CH$_2$)$_n$-(-8- to 12-membered bicyclic heterocycle), -phenylene-(C$_2$-C$_{10}$ alkynyl), -phenylene-(CH$_2$)$_m$COOH, -phenylene-(CH$_2$)$_m$-(-3- to 7-membered monocyclic heterocycle), -phenylene-(CH$_2$)$_m$COO—(C$_1$-C$_{10}$ alkyl) or —C(O)—(C$_1$-C$_{10}$ alkyl);

each m is independently an integer ranging from 0 to 4; and each n is independently an integer ranging from 1 to 5.

A compound of Formula (Ia), (Ib), (Ic) or (Id) or a pharmaceutically acceptable salt thereof (a "Purine Derivative") is useful for treating or preventing a cardiovascular disease, a neurological disorder, a skin disorder, an ischemic condition, a reperfusion injury, a wound, a radiation-induced injury, an inflammatory disease or a cellular proliferative disorder (each being a "Condition").

The invention also provides compositions comprising an effective amount of a Purine Derivative and a physiologically acceptable vehicle. The compositions are useful for treating or preventing a Condition.

The invention further provides methods for treating or preventing a Condition, the methods comprising administering an effective amount of a Purine Derivative to a subject in need thereof.

The details of the invention are set forth in the accompanying description below. Other features, objects, and advantages of the invention will be apparent from the description and from the claims. All patents, patent applications and publications cited in this specification are incorporated herein by reference for all purposes.

4. BRIEF DESCRIPTION OF THE DRAWINGS

FIG. 1 shows the effect of Compound 24 on TNF-α levels (pg/mL) in a BALB-C murine model of asthma-associated inflammation. The shaded bar at the far left represents TNF-α levels (pg/mL) in untreated control mice. The center grouping of bars represents TNF-α levels (pg/mL) in mice treated via oral administration of Compound 24 at dosages of 0.03 mg/kg (black bar), 0.1 mg/kg (gray bar), and 0.3 mg/kg (white bar). The grouping of bars at the far right represents TNF-α levels (pg/mL) in mice treated via intraperitoneal administration of Compound 24 at dosages of 0.03 mg/kg (black bar), 0.1 mg/kg (gray bar), and 0.3 mg/kg (white bar).

Figure 2:
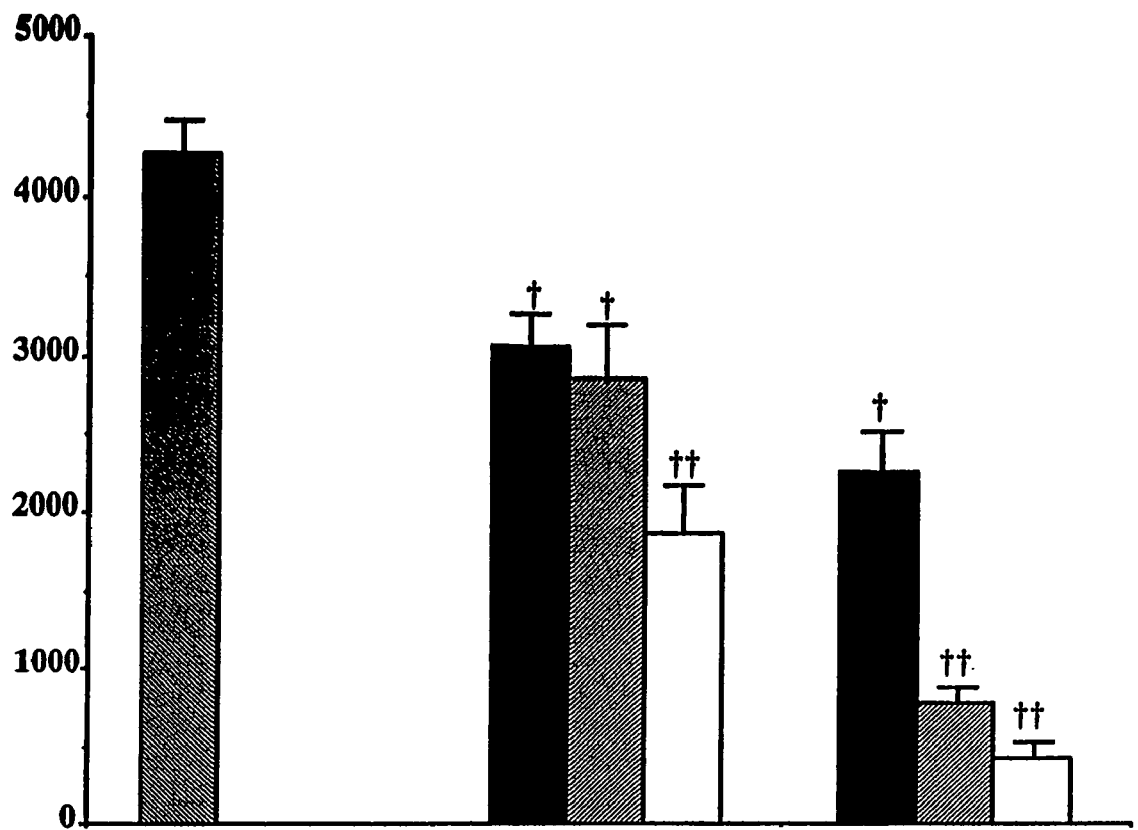

FIG. 2 shows the effect of Compound 24 on MIP-1α levels (pg/mL) in a BALB-C murine model of asthma-associated inflammation. The shaded bar at the far left represents MIP-1α levels (pg/mL) in untreated control mice. The center grouping of bars represents MIP-1α levels (pg/mL) in mice treated via oral administration of Compound 24 at dosages of 0.03 mg/kg (black bar), 0.1 mg/kg (gray bar), and 0.3 mg/kg (white bar). The grouping of bars at the far right represents MIP-1α levels (pg/mL) in mice treated via intraperitoneal administration of Compound 24 at dosages of 0.03 mg/kg (black bar), 0.1 mg/kg (gray bar), and 0.3 mg/kg (white bar).

5. DETAILED DESCRIPTION OF THE INVENTION

5.1 Definitions

The term "C$_1$-C$_6$ alkyl" as used herein refers to a straight or branched chain, saturated hydrocarbon having from 1 to 6 carbon atoms. Representative C$_1$-C$_6$ alkyl groups include, but are not limited to methyl, ethyl, propyl, isopropyl, butyl, sec-butyl, tert-buty, pentyl, isopentyl, neopentyl, hexyl, isohexyl, and neohexyl. In one embodiment, the C$_1$-C$_6$ alkyl group is substituted with one or more of the following groups: -halo, —O—(C$_1$-C$_6$ alkyl), —OH, —CN, —COOR', —OC(O)R', —N(R')$_2$, —NHC(O)R' or —C(O)NHR' groups wherein each R' is independently —H or unsubstituted —C$_1$-C$_6$ alkyl. Unless indicated, the C$_1$-C$_6$ alkyl group is unsubstituted.

The term "C$_1$-C$_{10}$ alkyl" as used herein refers to a straight or branched chain, saturated hydrocarbon having from 1 to 10 carbon atoms. Representative C1-C$_{10}$ alkyl groups include, but are not limited to methyl, ethyl, propyl, isopropyl, butyl, sec-butyl, tert-butyl, pentyl, isopentyl, neopentyl, hexyl, isohexyl, neohexyl, heptyl, isoheptyl, neoheptyl, octyl, isooctyl, neooctyl, nonyl, isononyl, neononyl, decyl, isodecyl and neodecyl. In one embodiment, the C$_1$-C$_{10}$ alkyl group is substituted with one or more of the following groups: -halo, —O—(C$_1$-C$_6$ alkyl), —OH, —CN, —COOR', —OC(O)R', —N(R')$_2$, —NHC(O)R' or —C(O)NHR' groups wherein each R' is independently —H or unsubstituted —C$_1$-C$_6$ alkyl. Unless indicated, the C$_1$-C$_{10}$ alkyl group is unsubstituted.

"$C_2$-$C_6$ alkynyl" refers to a straight or branched chain unsaturated hydrocarbon containing 2-6 carbon atoms and at least one triple bond. Examples of a $C_2$-$C_6$ alkynyl group include, but are not limited to, acetylene, propyne, 1-butyne, 2-butyne, isobutyne, sec-butyne, 1-pentyne, 2-pentyne, isopentyne, 1-hexyne, 2-hexyne, 3-hexyne and isohexyne.

"$C_2$-$C_{10}$ alkynyl" refers to a straight or branched chain unsaturated hydrocarbon containing 2-10 carbon atoms and at least one triple bond. Examples of a $C_2$-$C_{10}$ alkynyl group include, but are not limited to, acetylene, propyne, 1-butyne, 2-butyne, isobutyne, sec-butyne, 1-pentyne, 2-pentyne, isopentyne, 1-hexyne, 2-hexyne, 3-hexyne, isohexyne, 1-heptyne, 2-heptyne, 3-heptyne, isoheptyne, 1-octyne, 2-octyne, 3-octyne, 4-octyne, isooctyne, 1-nonyne, 2-nonyne, 3-nonyne, 4-nonyne, isononyne, 1-decyne, 2-decyne, 3-decyne, 4-decyne, 5-decyne, and isodecyne.

The term "aryl" as used herein refers to a phenyl group or a naphthyl group. In one embodiment, the aryl group is substituted with one or more of the following groups: -halo, —O—($C_1$-$C_6$ alkyl), —OH, —CN, —COOR', —OC(O)', —N(R')$_2$, —NHC(O)R' or —C(O)NHR' groups wherein each R' is independently —H or unsubstituted —$C_1$-$C_6$ alkyl. Unless indicated, the aryl group is unsubstituted.

The term "$C_3$-$C_8$ monocyclic cycloalkyl" as used herein is a 3-, 4-, 5-, 6-, 7- or 8-membered saturated non-aromatic monocyclic cycloalkyl ring. Representative $C_3$-$C_8$ monocyclic cycloalkyl groups include, but are not limited to, cyclopropyl, cyclobutyl, cyclopentyl, cyclohexyl, cycloheptyl and cyclooctyl. In one embodiment, the $C_3$-$C_8$ monocyclic cycloalkyl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently -H or unsubstituted —$C_1$-$C_6$ alkyl. Unless indicated, the $C_3$-$C_8$ monocyclic cycloalkyl group is unsubstituted.

The term "$C_3$-$C_8$ monocyclic cycloalkenyl" as used herein is a 3-, 4-, 5-, 6-, 7- or 8-membered non-aromatic monocyclic carbocyclic ring having at least one endocyclic double bond, but which is not aromatic. It is to be understood that when any two groups, together with the carbon atom to which they are attached form a $C_3$-$C_8$ monocyclic cycloalkenyl group, the carbon atom to which the two groups are attached remains tetravalent. Representative $C_3$-$C_8$ monocyclic cycloalkenyl groups include, but are not limited to, cyclopropenyl, cyclobutenyl, 1,3-cyclobutadienyl, cyclopentenyl, 1,3-cyclopentadienyl, cyclohexenyl, 1,3-cyclohexadienyl, cycloheptenyl, 1,3-cycloheptadienyl, 1,4-cycloheptadienyl, -1,3,5-cycloheptatrienyl, cyclooctenyl, 1,3-cyclooctadienyl, 1,4-cyclooctadienyl, -1,3,5-cyclooctatrienyl. In one embodiment, the $C_3$-$C_8$ monocyclic cycloalkenyl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the $C_3$-$C_8$ monocyclic cycloalkenyl group is unsubstituted.

The term "$C_8$-$C_{12}$ bicyclic cycloalkyl" as used herein is a 8-, 9-, 10-, 11- or 12-membered saturated, non-aromatic bicyclic cycloalkyl ring system. Representative $C_8$-$C_{12}$ bicyclic cycloalkyl groups include, but are not limited to, decahydronaphthalene, octahydroindene, decahydrobenzocycloheptene, and dodecahydroheptalene. In one embodiment, the $C_8$-$C_{12}$ bicyclic cycloalkyl group is substituted with one or more of the following groups: -halo, —O—($C_1$-$C_6$ alkyl), —OH, —CN, —COOR', —OC(O)R', —N(R')$_2$, —NHC(O) R' or —C(O)NHR' groups wherein each R' is independently —H or unsubstituted —$C_1$-$C_6$ alkyl. Unless indicated, the $C_8$-$C_{12}$ bicyclic cycloalkyl group is unsubstituted.

The term "$C_8$-$C_{12}$ bicyclic cycloalkenyl" as used herein is a 8-, 9-, 10-, 11- or 12-membered, aromatic or non-aromatic bicyclic cycloalkyl ring system, having at least one endocyclic double bond. It is to be understood that when any two groups, together with the carbon atom to which they are attached form a $C_8$-$C_{12}$ bicyclic cycloalkenyl group, the carbon atom to which the two groups are attached remains tetravalent. Representative $C_8$-$C_{12}$ bicyclic cycloalkenyl groups include, but are not limited to, tetrahydronaphthalene, octahydronaphthalene, hexahydronaphthalene, hexahydroindene, tetrahydroindene, octahydrobenzocycloheptene, hexahydrobenzocycloheptene, tetrahydrobenzocycloheptene, decahydroheptalene, octahydroheptalene, hexahydroheptalene, and tetrahydroheptalene. In one embodiment, the $C_8$-$C_{12}$ bicyclic cycloalkyl group is substituted with one or more of the following groups: -halo, —O—($C_1$-$C_6$ alkyl), —OH, —CN, —COOR', —OC(O)R', —N(R')$_2$, —NHC(O) R' or —C(O)NHR' groups wherein each R' is independently —H or unsubstituted —$C_1$-$C_6$ alkyl. Unless indicated, the $C_8$-$C_{12}$ bicyclic cycloalkenyl group is unsubstituted.

The term "2-cyclopentenyl" as used herein, refers to the following chemical group:

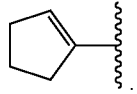

The term "3-cyclopentenyl" as used herein, refers to the following chemical group:

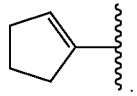

The term "2-cyclohexenyl" as used herein, refers to the following chemical group:

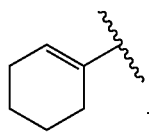

The term "3-cyclohexenyl" as used herein, refers to the following chemical group:

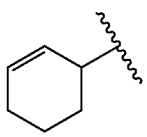

The term "4-cyclohexenyl" as used herein, refers to the following chemical group:

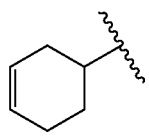

The term "effective amount" as used herein, refers to an amount of a Purine Derivative that is effective for treating or preventing a Condition.

The term "halo" as used herein refers to —F, —Cl, —Br or —I.

The term "3- to 7-membered monocyclic heterocycle" refers to: (i) a 3- or 4-membered non-aromatic monocyclic cycloalkyl in which 1 of the ring carbon atoms has been replaced with an N, O or S atom; or (ii) a 5-, 6-, or 7-membered aromatic or non-aromatic monocyclic cycloalkyl in which 1-4 of the ring carbon atoms have been independently replaced with a N, O or S atom. The non-aromatic 3- to 7-membered monocyclic heterocycles can be attached via a ring nitrogen, sulfur, or carbon atom. The aromatic 3- to 7-membered monocyclic heterocycles are attached via a ring carbon atom. Representative examples of a 3- to 7-membered monocyclic heterocycle group include, but are not limited to furanyl, furazanyl, imidazolidinyl, imidazolinyl, imidazolyl, isothiazolyl, isoxazolyl, morpholinyl, oxadiazolyl, oxazolidinyl, oxazolyl, oxazolidinyl, pyrimidinyl, phenanthridinyl, phenanthrolinyl, piperazinyl, piperidinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, quinuclidinyl, tetrahydrofuranyl, thiadiazinyl, thiadiazolyl, thienyl, thienothiazolyl, thienooxazolyl, thienoimidazolyl, thiomorpholinyl, thiophenyl, triazinyl, triazolyl, In one embodiment, the 3- to 7-membered monocyclic heterocycle group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the 3- to 7-membered monocyclic heterocycle group is unsubstituted.

The term "8- to 12-membered bicyclic heterocycle" refers to a bicyclic 8- to 12-membered aromatic or non-aromatic bicyclic cycloalkyl in which one or both of the of the rings of the bicyclic ring system have 1-4 of it's ring carbon atoms independently replaced with a N, O or S atom. Included in this class are 3- to 7-membered monocyclic heterocycles that are fused to a benzene ring. A non-aromatic ring of an 8- to 12-membered monocyclic heterocycle is attached via a ring nitrogen, sulfur, or carbon atom. An aromatic 8- to 12-membered monocyclic heterocycles are attached via a ring carbon atom. Examples of 8- to 12-membered bicyclic heterocycles include, but are not limited to, benzimidazolyl, benzofuranyl, benzothiofuranyl, benzothiophenyl, benzoxazolyl, benzthiazolyl, benztriazolyl, benztetrzolyl, benzisoxazolyl, benzisothiazolyl, benzimidazolinyl, cinnolinyl, decahydroquinolinyl, 1H-indazolyl, indolenyl, indolinyl, indolizinyl, indolyl, isobenzofuranyl, isoindazolyl, isoindolyl, isoindolinyl, isoquinolinyl, naphthyridinyl, octahydroisoquinolinyl, phthalazinyl, pteridinyl, purinyl, quinoxalinyl, tetrahydroisoquinolinyl, tetrahydroquinolinyl, and xanthenyl. In one embodiment, each ring of a the -8- to 12-membered bicyclic heterocycle group can substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the 8- to 12-membered bicyclic heterocycle group is unsubstituted.

The term "3- to 7-membered nitrogen-containing monocyclic heterocycle" refers to: (i) a 3- or 4-membered non-aromatic monocyclic cycloalkyl in which 1 of the ring carbon atoms has been replaced with a N atom; or (ii) a 5-, 6-, or 7-membered aromatic or non-aromatic monocyclic cycloalkyl in which 1 of the ring carbon atoms has been replaced with a N atom and 0-3 of the remaining ring carbon atoms have been independently replaced with a N, O or S atom. The non-aromatic 3- to 7-membered nitrogen-containing monocyclic heterocycles can be attached via a ring nitrogen, sulfur, or carbon atom. The aromatic 3- to 7-membered nitrogen-containing monocyclic heterocycles are attached via a ring carbon atom. Representative examples of a 3- to 7-membered nitrogen-containing monocyclic heterocycle group include, but are not limited to furanyl, furazanyl, imidazolidinyl, imidazolinyl, imidazolyl, isothiazolyl, isoxazolyl, morpholinyl, oxadiazolyl, oxazolidinyl, oxazolyl, oxazolidinyl, pyrimidinyl, phenanthridinyl, phenanthrolinyl, piperazinyl, piperidinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, quinuclidinyl, tetrahydrofuranyl, thiadiazinyl, thiadiazolyl, thienyl, thienothiazolyl, thienooxazolyl, thienoimidazolyl, thiomorpholinyl, triazinyl or triazolyl. In one embodiment, the 3- to 7-membered nitrogen-containing monocyclic heterocycle group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently -H or unsubstituted —$C_1$-$C_6$ alkyl. Unless indicated, the 3- to 7-membered nitrogen-containing monocyclic heterocycle group is unsubstituted.

The term "8- to 12-membered nitrogen-containing bicyclic heterocycle" refers to an 8- to 12-membered aromatic or non-aromatic bicyclic cycloalkyl in which 1 of the ring carbon atoms has been replaced with a N atom and 0-3 of the remaining ring carbon atoms have been independently replaced with a N, O or S atom. Included in this class are 3- to 7-membered nitrogen-containing monocyclic heterocycles that are fused to a benzene ring. A non-aromatic ring of an 8- to 12-membered nitrogen-containing monocyclic heterocycle is attached via a ring nitrogen, sulfur, or carbon atom. The aromatic 8- to 12-membered nitrogen-containing monocyclic heterocycles are attached via a ring carbon atom. Examples of 8- to 12-membered nitrogen-containing bicyclic heterocycles include, but are not limited to, benzimidazolyl, benzoxazolyl, benztriazolyl, benztetrazolyl, benzisoxazolyl, benzisothiazolyl, benzimidazolinyl, cinnolinyl, decahydroquinolinyl, 1H-indazolyl, indolenyl, indolinyl, indolizinyl, indolyl, isoindazolyl, isoindolyl, isoindolinyl, isoquinolinyl, naphthyridinyl, octahydroisoquinolinyl, phthalazinyl, pteridinyl, purinyl, quinoxalinyl, tetrahydroisoquinolinyl, tetrahydroquinolinyl, and xanthenyl. In one embodiment, each ring of a the -8- to 12-membered nitrogen-containing bicyclic heterocycle group can substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the -8- to 12-membered nitrogen-containing bicyclic heterocycle group is unsubstituted.

The term "phenylene" as used herein, refers to a benzene ring in which two of the benzene ring's hydrogen atoms have been replaced with single bonds. Representative examples of a "phenylene group" are depicted below:

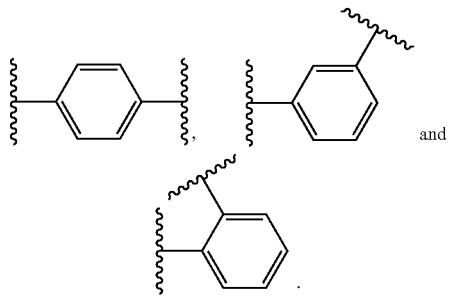

The phrase "pharmaceutically acceptable salt," as used herein, is a salt of an acid and a basic nitrogen atom of a Purine Derivative. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also refers to a salt of a Purine Derivative having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2—OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl)amine; N-methyl-D-glucamine; and amino acids such as arginine, lysine, and the like. The term "pharmaceutically acceptable salt" also includes a hydrate of a Purine Derivative.

A "subject" is a mammal, e.g., a human, mouse, rat, guinea pig, dog, cat, horse, cow, pig, or non-human primate, such as a monkey, chimpanzee or baboon. In one embodiment, the monkey is a rhesus. In one embodiment, the subject is a human.

The term "isolated and purified" as used herein means separate from other components of a reaction mixture or natural source. In certain embodiments, the isolate contains at least 30%, at least 35%, at least 40%, at least 45%, at least 50%, at least 55%, at least 60%, at least 65%, at least 70%, at least 75%, at least 80%, at least 85%, at least 90%, at least 95% or at least 98% of a Purine Derivative by weight of the isolate. In one embodiment, the isolate contains at least 95% of a Purine Derivative by weight of the isolate.

The term "substantially free of its corresponding opposite enantiomer" as used herein, means that a Purine Derivative contains no more than about 10% by weight of its corresponding opposite enantiomer. In one embodiment the Purine Derivative that is substantially free of its corresponding opposite enantiomer contains no more than about 5% by weight of its corresponding opposite enantiomer. In a further embodiment a Purine Derivative that is substantially free of its corresponding opposite enantiomer contains no more than about 1% by weight of its corresponding opposite enantiomer. In another embodiment a Purine Derivative that is substantially free of its corresponding opposite enantiomer contains no more than about 0.5% by weight of its corresponding opposite enantiomer. In still another embodiment a Purine Derivative that is substantially free of its corresponding opposite enantiomer contains no more than about 0.1% by weight of its corresponding opposite enantiomer.

The term "substantially free of its corresponding other anomer" as used herein, means that a Purine Derivative contains no more than about 10% by weight of its corresponding other anomer. In one embodiment the Purine Derivative that is substantially free of its corresponding other anomer contains no more than about 5% by weight of its corresponding other anomer. In a further embodiment a Purine Derivative that is substantially free of its corresponding other anomer contains no more than about 1% by weight of its corresponding other anomer. In another embodiment a Purine Derivative that is substantially free of its corresponding other anomer contains no more than about 0.5% by weight of its corresponding other anomer. In still another embodiment a Purine Derivative that is substantially free of its corresponding other anomer contains no more than about 0.1% by weight of its corresponding other anomer.

5.2 The Purine Derivatives

5.2.1 The Purine Derivatives of Formula (Ia)

As stated above, the present invention encompasses Purine Derivatives having the Formula (Ia):

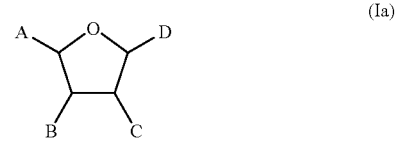

(Ia)

wherein A, B, C and D are defined above for the Purine Derivatives of Formula (Ia), and A and B are trans with respect to each other; B and C are cis with respect to each other; and C and D are cis or trans with respect to each other.

In one embodiment, $R^1$ is -3- to 7-membered monocyclic heterocycle.

In another embodiment, $R^1$ is -8- to 12-membered bicyclic heterocycle.

In one embodiment, $R^2$ is —CN.

In another embodiment, $R^2$ is —NHC(O)OR$^4$ or —NHC(O)NHR$^4$.

In another embodiment, $R^2$ is —NHNHC(O)R$^4$, —NHNHC(O)OR or —NHNHC(O)NHR$^4$.

In yet another embodiment, $R^2$ is —NH—N=C(R$^5$)R$^6$.

In one embodiment, $R^3$ is —C$_1$-C$_{10}$ alkyl.

In another embodiment, $R^3$ is -aryl.

In another embodiment, $R^3$ is -3- to 7-membered monocyclic heterocycle or -8- to 12-membered bicyclic heterocycle. In still another embodiment, $R^3$ is —C$_3$-C$_8$ monocyclic cycloalkyl, —C$_3$-C$_8$ monocyclic cycloalkenyl, —C$_8$-C$_{12}$ bicyclic cycloalkyl or —C$_8$-C$_{12}$ bicyclic cycloalkenyl.

In one embodiment, C and D are cis with respect to each other.

In another embodiment, C and D are trans with respect to each other.

The present invention also provides compositions comprising an effective amount of a Purine Derivative of Formula (Ia) and a physiologically acceptable vehicle.

The invention further provides Purine Derivatives of Formula (Ia) that are in isolated and purified form.

The invention still further provides methods for treating or preventing a Condition, comprising administering an effective amount of a Purine Derivative of Formula (Ia) to a subject in need thereof.

The Purine Derivatives of Formula (Ia) can exist in the form of a single enantiomer, for example, that depicted by either the Formula (Ia') or Formula (Ia"):

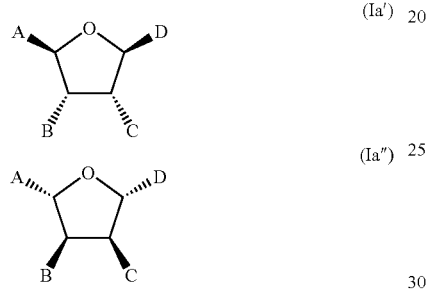

wherein A, B, C and D are defined above for the Purine Derivatives of Formula (Ia).

A Purine Derivative of Formula (Ia') is the corresponding opposite enantiomer of a Purine Derivative of Formula (Ia") when group A of the Purine Derivative of Formula (Ia') is the same as group A of the Purine Derivative of Formula (Ia") and when group D of the Purine Derivative of Formula (Ia') is the same as group D of the Purine Derivative of Formula (Ia").

A Purine Derivative of Formula (Ia") is the corresponding opposite enantiomer of a Purine Derivative of Formula (Ia') when group A of the Purine Derivative of Formula (Ia") is the same as group A of the Purine Derivative of Formula (Ia') and when group D of the Purine Derivative of Formula (Ia") is the same as group D of the Purine Derivative of Formula (Ia').

In one embodiment, the Purine Derivatives of Formula (Ia) have the formula (Ia'), depicted above, wherein A, B, C and D are defined above for the Purine Derivatives of Formula (Ia), and wherein the Purine Derivatives of Formula (Ia') are substantially free of their corresponding opposite enantiomer.

In another embodiment, the Purine Derivatives of Formula (Ia) have the formula (Ia"), depicted above, wherein A, B, C and D are defined above for the Purine Derivatives of Formula (Ia), and wherein the Purine Derivatives of Formula (Ia") are substantially free of their corresponding opposite enantiomer.

In another embodiment, the Purine Derivatives of Formula (Ia) exist as a mixture of a Purine Derivative of Formula (Ia') and a Purine Derivative of Formula (Ia") wherein the amount of the Purine Derivative of Formula (Ia') exceeds the amount of the Purine Derivative of Formula (Ia").

In a further embodiment, the Purine Derivatives of Formula (Ia) exist as a mixture of a Purine Derivative of Formula (Ia') and a Purine Derivative of Formula (Ia") wherein the amount of the Purine Derivative of Formula (Ia") exceeds the amount of the Purine Derivative of Formula (Ia').

In another embodiment, the Purine Derivatives of Formula (Ia) exist as a racemic mixture of a Purine Derivative of Formula (Ia') and a Purine Derivative of Formula (Ia").

In another embodiment, the Purine Derivatives of Formula (Ia) can exist in the form of a single enantiomer, for example, that depicted by either formula (Iaa') or (Iaa"):

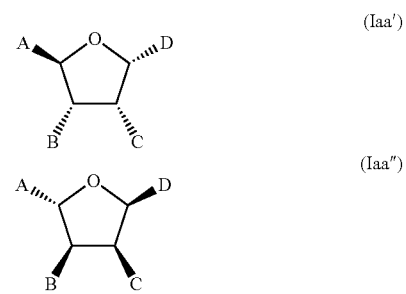

wherein A, B, C and D are defined above for the Purine Derivatives of Formula (Ia).

A Purine Derivative of Formula (Iaa') is the corresponding opposite enantiomer of a Purine Derivative of Formula (Iaa") when group A of the Purine Derivative of Formula (Iaa') is the same as group A of the Purine Derivative of Formula (Iaa") and when group D of the Purine Derivative of Formula (Iaa') is the same as group D of the Purine Derivative of Formula (Iaa").

A Purine Derivative of Formula (Iaa") is the corresponding opposite enantiomer of a Purine Derivative of Formula (Iaa') when group A of the Purine Derivative of Formula (Iaa") is the same as group A of the Purine Derivative of Formula (Iaa') and when group D of the Purine Derivative of Formula (Iaa") is the same as group D of the Purine Derivative of Formula (Iaa').

In one embodiment, the Purine Derivatives of Formula (Ia) have the formula (Iaa'), depicted above, wherein A, B, C and D are defined above for the Purine Derivatives of Formula (Ia), and wherein the Purine Derivatives of Formula (Iaa') are substantially free of their corresponding opposite enantiomer.

In another embodiment, the Purine Derivatives of Formula (Ia) have the formula (Iaa"), depicted above, wherein A, B, C and D are defined above for the Purine Derivatives of Formula (Ia), and wherein the Purine Derivatives of Formula (Iaa") are substantially free of their corresponding opposite enantiomer.

In another embodiment, the Purine Derivatives of Formula (Ia) exist as a mixture of a Purine Derivative of Formula (Iaa') and a Purine Derivative of Formula (Iaa") wherein the amount of the Purine Derivative of Formula (Iaa') exceeds the amount of the Purine Derivative of Formula (Iaa").

In a further embodiment, the Purine Derivatives of Formula (Ia) exist as a mixture of a Purine Derivative of Formula (Iaa') and a Purine Derivative of Formula (Iaa") wherein the amount of the Purine Derivative of Formula (Iaa") exceeds the amount of the Purine Derivative of Formula (Iaa').

In another embodiment, the Purine Derivatives of Formula (Ia) exist as a racemic mixture of a Purine Derivative of Formula (Iaa') and a Purine Derivative of Formula (Iaa").

A Purine Derivative of Formula (Iaa') is the corresponding other anomer of a Purine Derivative of Formula (Ia') when group A of the Purine Derivative of Formula (Iaa') is the same as group A of the Purine Derivative of Formula (Ia') and when group D of the Purine Derivative of Formula (Iaa') is the same as group D of the Purine Derivative of Formula (Ia').

A Purine Derivative of Formula (Ia') is the corresponding other anomer of a Purine Derivative of Formula (Iaa') when group A of the Purine Derivative of Formula (Ia') is the same as group A of the Purine Derivative of Formula (Iaa') and when group D of the Purine Derivative of Formula (Ia') is the same as group D of the Purine Derivative of Formula (Iaa').

A Purine Derivative of Formula (Iaa") is the corresponding other anomer of a Purine Derivative of Formula (Ia") when group A of the Purine Derivative of Formula (Iaa") is the same as group A of the Purine Derivative of Formula (Ia") and when group D of the Purine Derivative of Formula (Iaa") is the same as group D of the Purine Derivative of Formula (Ia").

A Purine Derivative of Formula (Ia") is the corresponding other anomer of a Purine Derivative of Formula (Iaa") when group A of the Purine Derivative of Formula (Ia") is the same as group A of the Purine Derivative of Formula (Iaa") and when group D of the Purine Derivative of Formula (Ia") is the same as group D of the Purine Derivative of Formula (Iaa").

In one embodiment, the Purine Derivatives of Formula (Ia) have the formula (Iaa'), depicted above, wherein A, B, C and D are defined above for the Purine Derivatives of Formula (Ia), and wherein the Purine Derivatives of Formula (Iaa') are substantially free of their corresponding other anomer.

In another embodiment, the Purine Derivatives of Formula (Ia) have the formula (Iaa"), depicted above, wherein A, B, C and D are defined above for the Purine Derivatives of Formula (Ia), and wherein the Purine Derivatives of Formula (Iaa") are substantially free of their corresponding other anomer.

In one embodiment, the Purine Derivatives of Formula (Ia) have the formula (Ia'), depicted above, wherein A, B, C and D are defined above for the Purine Derivatives of Formula (Ia), and wherein the Purine Derivatives of Formula (Ia') are substantially free of their corresponding other anomer.

In another embodiment, the Purine Derivatives of Formula (Ia) have the formula (Ia"), depicted above, wherein A, B, C and D are defined above for the Purine Derivatives of Formula (Ia), and wherein the Purine Derivatives of Formula (Ia") are substantially free of their corresponding other anomer.

In one embodiment, the Purine Derivatives of Formula (Ia) exist as a mixture of a Purine Derivative of Formula (Ia') and a Purine Derivative of Formula (Iaa') wherein the amount of the Purine Derivative of Formula (Ia') exceeds the amount of the Purine Derivative of Formula (Iaa').

In another embodiment, the Purine Derivatives of Formula (Ia) exist as a mixture of a Purine Derivative of Formula (Ia') and a Purine Derivative of Formula (Iaa') wherein the amount of the Purine Derivative of Formula (Iaa') exceeds the amount of the Purine Derivative of Formula (Ia').

In a further embodiment, the Purine Derivatives of Formula (Ia) exist as an equimolar mixture of a Purine Derivative of Formula (Ia') and a Purine Derivative of Formula (Iaa').

In one embodiment, the Purine Derivatives of Formula (Ia) exist as a mixture of a Purine Derivative of Formula (Ia") and a Purine Derivative of Formula (Iaa") wherein the amount of the Purine Derivative of Formula (Ia") exceeds the amount of the Purine Derivative of Formula (Iaa").

In another embodiment, the Purine Derivatives of Formula (Ia) exist as a mixture of a Purine Derivative of Formula (Ia") and a Purine Derivative of Formula (Iaa") wherein the amount of the Purine Derivative of Formula (Iaa") exceeds the amount of the Purine Derivative of Formula (Ia").

In a further embodiment, the Purine Derivatives of Formula (Ia) exist as an equimolar mixture of a Purine Derivative of Formula (Ia") and a Purine Derivative of Formula (Iaa").

5.2.2 The Purine Derivatives of Formula (Ib)

As stated above, the present invention encompasses Purine Derivatives having the Formula (Ib):

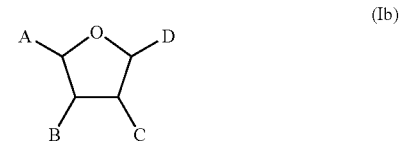

wherein A, B, C and D are defined above for the Purine Derivatives of Formula (Ib), and A and B are trans with respect to each other; B and C are cis with respect to each other; and C and D are cis or trans with respect to each other.

In one embodiment, $R^1$ is —H.
In another embodiment, $R^1$ is —$C_1$-$C_{10}$ alkyl.
In a specific embodiment, $R^1$ is ethyl.
In another embodiment, $R^1$ is -aryl or —$(CH_2)_n$-aryl.
In another embodiment, $R^1$ is —$C_3$-$C_8$ monocyclic cycloalkyl.
In another embodiment, $R^1$ is —$C_3$-$C_8$ monocyclic cycloalkenyl.
In another embodiment, $R^1$ is —$C_8$-$C_{12}$ bicyclic cycloalkyl or —$C_8$-$C_{12}$ bicyclic cycloalkenyl.
In one embodiment, $R^2$ is —NHC(O)$OR^4$ or —NHC(O)$NHR^4$.
In another embodiment, $R^2$ is —NHNHC(O)$R^4$, —NHNHC(O)$OR^4$ or —NHNHC(O)$NHR^4$.
In another embodiment, $R^2$ is —NH—N=C($R^9$)$R^{1-}$.
In still another embodiment, $R^2$ is —NH—N=CH—$C_3$-$C_8$ monocyclic cycloalkenyl.
In another embodiment, $R^2$ is —NH—N=CH-phenylene-$(CH_2)_m$COOH.
In a further embodiment, $R^2$ is —NH—N=CH-phenylene-$(CH_2)_m$-COO—($C_1$-$C_{10}$ alkyl).
In another embodiment, $R^2$ is —NH—N=CH-phenylene-$(CH_2)_m$—COO-(3- to 7-membered monocyclic heterocycle).
In one embodiment, $R^3$ is —$C_1$-$C_{10}$ alkyl.
In another embodiment, $R^3$ is -aryl.
In another embodiment, $R^3$ is -3- to 7-membered monocyclic heterocycle.
In a specific embodiment, $R^3$ is methyl.
In another specific embodiment, $R^3$ is ethyl.
In one embodiment, $R^1$ is —H and $R^3$ is —$C_1$-$C_{10}$ alkyl.
In a specific embodiment, $R^1$ is —H and $R^3$ is ethyl.
In another embodiment, $R^1$ is —$C_1$-$C_{10}$ alkyl and $R^3$ is —$C_1$-$C_{10}$ alkyl.
In a specific embodiment, $R^1$ and $R^3$ are each ethyl.
In one embodiment, $R^1$ is —H, $R^2$ is —NH—N=C($R^9$)$R^{10}$, and $R^3$ is —$C_1$-$C_{10}$ alkyl.
In a specific embodiment, $R^1$ is —H, $R^2$ is —NH—N=C($R^9$)$R^{10}$, and $R^3$ is ethyl.
In another specific embodiment, $R^2$ is —H and is $R^3$ is ethyl.
In one embodiment, C and D are cis with respect to each other.
In another embodiment, C and D are trans with respect to each other.

The present invention also provides compositions comprising an effective amount of a Purine Derivative of Formula (Ib) and a physiologically acceptable vehicle.

The invention further provides Purine Derivatives of Formula (Ib) that are in isolated and purified form.

The invention still further provides methods for treating or preventing a Condition, comprising administering an effective amount of a Purine Derivative of Formula (Ib) to a subject in need thereof.

The Purine Derivatives of Formula (Ib) can exist in the form of a single enantiomer, for example, that depicted by either the Formula (Ib') or Formula (Ib"):

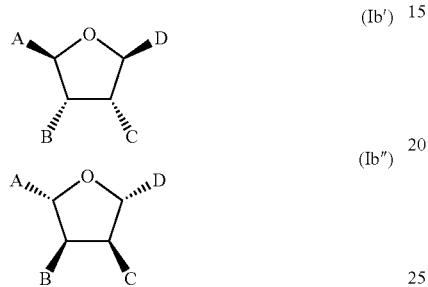

wherein A, B, C and D are defined above for the Purine Derivatives of Formula (Ib).

A Purine Derivative of Formula (Ib') is the corresponding opposite enantiomer of a Purine Derivative of Formula (Ib") when group A of the Purine Derivative of Formula (Ib') is the same as group A of the Purine Derivative of Formula (Ib") and when group D of the Purine Derivative of Formula (Ib') is the same as group D of the Purine Derivative of Formula (Ib").

A Purine Derivative of Formula (Ib") is the corresponding opposite enantiomer of a Purine Derivative of Formula (Ib') when group A of the Purine Derivatives of Formula (Ib") is the same as group A of the Purine Derivative of Formula (Ib') and when group D of the Purine Derivative of Formula (Ib") is the same as group D of the Purine Derivative of Formula (Ib').

In one embodiment, the Purine Derivatives of Formula (Ib) have the formula (Ib'), depicted above, wherein A, B, C and D are defined above for the Purine Derivatives of Formula (Ib), and wherein the Purine Derivatives of Formula (Ib') are substantially free of their corresponding enantiomer, represented by Formula (Ib").

In another embodiment, the Purine Derivatives of Formula (Ib) have the formula (Ib"), depicted above, wherein A, B, C and D are defined above for the Purine Derivatives of Formula (Ib), and wherein the Purine Derivatives of Formula (Ib") are substantially free of their corresponding enantiomer, represented by Formula (Ib').

In one embodiment, the Purine Derivatives of Formula (Ib) exist as a mixture of a Purine Derivative of Formula (Ib') and a Purine Derivative of Formula (Ib") wherein the amount of the Purine Derivative of Formula (Ib') exceeds the amount of the Purine Derivative of Formula (Ib").

In another embodiment, the Purine Derivatives of Formula (Ib) exist as a mixture of a Purine Derivative of Formula (Ib') and a Purine Derivative of Formula (Ib") wherein the amount of the Purine Derivative of Formula (Ib") exceeds the amount of the Purine Derivative of Formula (Ib').

In another embodiment, the Purine Derivatives of Formula (Ib) exist as a racemic mixture of a Purine Derivative of Formula (Ib') and a Purine Derivative of Formula (Ib").

In another embodiment, the Purine Derivatives of Formula (Ib) can exist in the form of a single enantiomer, for example, that depicted by either formula (Ibb') or (Ibb"):

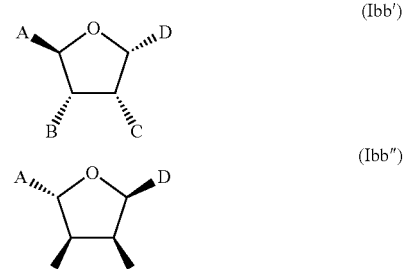

wherein A, B, C and D are defined above for the Purine Derivatives of Formula (Ib).

A Purine Derivative of Formula (Ibb') is the corresponding opposite enantiomer of a Purine Derivative of Formula (Ibb") when group A of the Purine Derivative of Formula (Ibb') is the same as group A of the Purine Derivative of Formula (Ibb") and when group D of the Purine Derivative of Formula (Ibb') is the same as group D of the Purine Derivative of Formula (Ibb").

A Purine Derivative of Formula (Ibb") is the corresponding opposite enantiomer of a Purine Derivative of Formula (Ibb') when group A of the Purine Derivative of Formula (Ibb") is the same as group A of the Purine Derivative of Formula (Ibb') and when group D of the Purine Derivative of Formula (Ibb") is the same as group D of the Purine Derivative of Formula (Ibb').

In one embodiment, the Purine Derivatives of Formula (Ib) have the formula (Ibb'), depicted above, wherein A, B, C and D are defined above for the Purine Derivatives of Formula (Ib), and wherein the Purine Derivatives of Formula (Ibb') are substantially free of their corresponding opposite enantiomer.

In another embodiment, the Purine Derivatives of Formula (Ib) have the formula (Ibb"), depicted above, wherein A, B, C and D are defined above for the Purine Derivatives of Formula (Ib), and wherein the Purine Derivatives of Formula (Ibb") are substantially free of their corresponding opposite enantiomer.

In another embodiment, the Purine Derivatives of Formula (Ib) exist as a mixture of a Purine Derivative of Formula (Ibb') and a Purine Derivative of Formula (Ibb") wherein the amount of the Purine Derivative of Formula (Ibb') exceeds the amount of the Purine Derivative of Formula (Ibb").

In a further embodiment, the Purine Derivatives of Formula (Ib) exist as a mixture of a Purine Derivative of Formula (Ibb') and a Purine Derivative of Formula (Ibb") wherein the amount of the Purine Derivative of Formula (Ibb") exceeds the amount of the Purine Derivative of Formula (Ibb').

In another embodiment, the Purine Derivatives of Formula (Ib) exist as a racemic mixture of a Purine Derivative of Formula (Ibb') and a Purine Derivative of Formula (Ibb").

A Purine Derivative of Formula (Ibb') is the corresponding other anomer of a Purine Derivative of Formula (Ib') when group A of the Purine Derivative of Formula (Ibb') is the same as group A of the Purine Derivative of Formula (Ib') and when group D of the Purine Derivative of Formula (Ibb') is the same as group D of the Purine Derivative of Formula (Ib').

A Purine Derivative of Formula (Ib') is the corresponding other anomer of a Purine Derivative of Formula (Ibb') when group A of the Purine Derivative of Formula (Ib') is the same as group A of the Purine Derivative of Formula (Ibb') and when group D of the Purine Derivative of Formula (Ib') is the same as group D of the Purine Derivative of Formula (Ibb').

A Purine Derivative of Formula (Ibb") is the corresponding other anomer of a Purine Derivative of Formula (Ib") when group A of the Purine Derivative of Formula (Ibb") is the same as group A of the Purine Derivative of Formula (Ib") and when group D of the Purine Derivative of Formula (Ibb") is the same as group D of the Purine Derivative of Formula (Ib").

A Purine Derivative of Formula (Ib") is the corresponding other anomer of a Purine Derivative of Formula (Ibb") when group A of the Purine Derivative of Formula (Ib") is the same as group A of the Purine Derivative of Formula (Ibb") and when group D of the Purine Derivative of Formula (Ib") is the same as group D of the Purine Derivative of Formula (Ibb").

In one embodiment, the Purine Derivatives of Formula (Ib) have the formula (Ibb'), depicted above, wherein A, B, C and D are defined above for the Purine Derivatives of Formula (Ib), and wherein the Purine Derivatives of Formula (Ibb') are substantially free of their corresponding other anomer.

In another embodiment, the Purine Derivatives of Formula (Ib) have the formula (Ibb"), depicted above, wherein A, B, C and D are defined above for the Purine Derivatives of Formula (Ib), and wherein the Purine Derivatives of Formula (Ibb") are substantially free of their corresponding other anomer.

In one embodiment, the Purine Derivatives of Formula (Ib) have the formula (Ib'), depicted above, wherein A, B, C and D are defined above for the Purine Derivatives of Formula (Ib), and wherein the Purine Derivatives of Formula (Ib') are substantially free of their corresponding other anomer.

In another embodiment, the Purine Derivatives of Formula (Ib) have the formula (Ib"), depicted above, wherein A, B, C and D are defined above for the Purine Derivatives of Formula (Ib), and wherein the Purine Derivatives of Formula (Ib") are substantially free of their corresponding other anomer.

In one embodiment, the Purine Derivatives of Formula (Ib) exist as a mixture of a Purine Derivative of Formula (Ib') and a Purine Derivative of Formula (Ibb') wherein the amount of the Purine Derivative of Formula (Ib') exceeds the amount of the Purine Derivative of Formula (Ibb').

In another embodiment, the Purine Derivatives of Formula (Ib) exist as a mixture of a Purine Derivative of Formula (Ib') and a Purine Derivative of Formula (Ibb') wherein the amount of the Purine Derivative of Formula (Ibb') exceeds the amount of the Purine Derivative of Formula (Ib').

In another embodiment, the Purine Derivatives of Formula (Ib) exist as an equimolar mixture of a Purine Derivative of Formula (Ib') and a Purine Derivative of Formula (Ibb').

In one embodiment, the Purine Derivatives of Formula (Ib) exist as a mixture of a Purine Derivative of Formula (Ib") and a Purine Derivative of Formula (Ibb") wherein the amount of the Purine Derivative of Formula (Ib") exceeds the amount of the Purine Derivative of Formula (Ibb").

In another embodiment, the Purine Derivatives of Formula (Ib) exist as a mixture of a Purine Derivative of Formula (Ib") and a Purine Derivative of Formula (Ibb") wherein the amount of the Purine Derivative of Formula (Ibb") exceeds the amount of the Purine Derivative of Formula (Ib").

In another embodiment, the Purine Derivatives of Formula (Ib) exist as an equimolar mixture of a Purine Derivative of Formula (Ib") and a Purine Derivative of Formula (Ibb").

Illustrative examples of the compounds of Formula (Ib') include the compounds listed below:

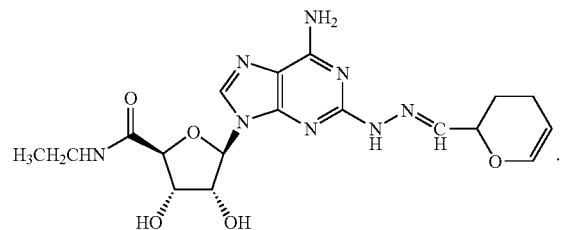

| Compound | $R^1$ | $R^9$ |
|---|---|---|
| 24 | —H | -4-cyclohexenyl |
| 25 | —H | -phenylene-4-($CH_2CH_2COOEt$) |
| 26 | —H | -phenylene-4-($CH_2CH_2COOH$) |
| 27 | —H | -phenylene-4-(-C≡C—$CH_2CH_2CH_2CH_3$) |
| 28 | —H | -(1-methyl)-1H-imidazol-5-yl |
| 29 | —H | -(1,3-dimethyl)-1H-pyrazol-5-yl |
| 30 | —H | -(1-methyl)-1H-pyrrol-4-yl-2-carboxylic acid methyl ester |
| 31 | —H | -(3,5-dimethyl)-isoxazol-4-yl |
| 32 | —H | -1H-imidazol-4-yl |
| 33 | —H | -(2-methyl)-furan-5-yl-3-carboxylic acid methyl ester |
| 34 | —H | -3,4-dihydro-2H-pyran-2-yl (racemate) |
| 35 | —H | -tetrahydrofuran-3-yl |
| 36 | —H | -furan-3-yl |
| 37 | —H | -furan-2-yl |
| 38 | —H | -tetrahydropyran-2-yl (racemate) |
| 39 | —H | -3,4-dihydro-2H-pyran-5-yl (racemate) |
| 40 | —H | -2H-chromen-3-yl |
| 41 | —H | —C(O)-phenyl |
| 42 | —$CH_2CH_3$ | -isobutyl |
| 43 | —H | -3,4-dihydro-2H-pyran-2-(R)-yl |
| 44 | —H | -3,4-dihydro-2H-pyran-2-(S)-yl |
| 45 | —H | -(5-hydroxymethyl)-furan-2-yl |
| 46 | —H | -(5-$CH_2CH_2COOH$)-furan-2-yl |
| 47 | —H | -benzo[1,3]dioxole-4-yl |
| 48 | —H | -2,3-dihydro-benzo[1,4]dioxine-6-yl |
| 49 | —H | —$CH_2CH_2CH(CH_3)_2$ | and pharmaceutically acceptable salts thereof.

The Compound of formula 34 is racemic and has the formula:

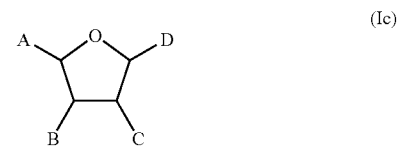

5.2.3 The Purine Derivatives of Formula (Ic)

As stated above, the present invention encompasses Purine Derivatives having the Formula (Ic):

(Ic)

wherein A, B, C and D are defined above for the Purine Derivatives of Formula (Ic), and A and B are trans with respect to each other; B and C are cis with respect to each other; and C and D are cis or trans with respect to each other.

In one embodiment, $R^1$ is —H.

In another embodiment, $R^1$ is —$C_1$-$C_{10}$ alkyl.

In a specific embodiment, $R^1$ is methyl.

In a specific embodiment, $R^1$ is ethyl.

In one embodiment, $R^1$ is -aryl or —$(CH_2)_n$-aryl.

In another embodiment, $R^1$ is —$C_3$-$C_8$ monocyclic cycloalkyl.

In a specific embodiment, $R^1$ is cyclopentyl.

In another embodiment, $R^1$ is —$C_3$-$C_8$ monocyclic cycloalkenyl.

In another embodiment, $R^1$ is —$C_8$-$C_{12}$ bicyclic cycloalkyl or —$C_8$-$C_{12}$ bicyclic cycloalkenyl.

In one embodiment, $R^2$ is —CN.

In another embodiment, $R^2$ is —NHC(O)$OR^4$ or —NHC(O)$NHR^4$.

In still another embodiment, $R^2$ is —NHNHC(O)$R^4$, —NHNHC(O)$OR^4$ or —NHNHC(O)$NHR^4$.

In one embodiment, $R^3$ is —$C_3$-$C_8$ monocyclic cycloalkenyl.

In another embodiment, $R^3$ is —$C_8$-$C_{12}$ bicyclic cycloalkyl or —$C_8$-$C_{12}$ bicyclic cycloalkenyl.

In yet another embodiment, $R^3$ is -3- to 7-membered monocyclic heterocycle or -8- to 12-membered bicyclic heterocycle;

In one embodiment, C and D are cis with respect to each other.

In another embodiment, C and D are trans with respect to each other.

The present invention also provides compositions comprising an effective amount of a Purine Derivative of Formula (Ic) and a physiologically acceptable vehicle.

The invention further provides Purine Derivatives of Formula (Ic) that are in isolated and purified form.

The invention still further provides methods for treating or preventing a Condition, comprising administering an effective amount of a Purine Derivative of Formula (Ic) to a subject in need thereof.

The Purine Derivatives of Formula (Ic) can exist in the form of a single enantiomer, for example, that depicted by either the Formula (Ic') or Formula (Ic"):

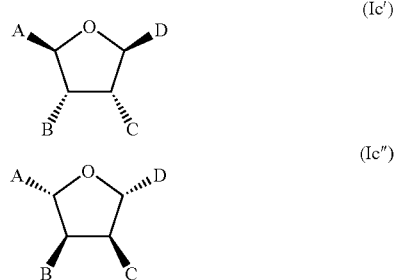

wherein A, B, C and D are defined above for the Purine Derivatives of Formula (Ic).

A Purine Derivative of Formula (Ic') is the corresponding opposite enantiomer of a Purine Derivative of Formula (Ic") when group A of the Purine Derivative of Formula (Ic") is the same as group A of the Purine Derivative of Formula (Ic') and when group D of the Purine Derivative of Formula (Ic') is the same as group D of the Purine Derivative of Formula (Ic").

A Purine Derivative of Formula (Ic") is the corresponding opposite enantiomer of a Purine Derivative of Formula (Ic') when group A of the Purine Derivatives of Formula (Ic") is the same as group A of the Purine Derivative of Formula (Ic') and when group D of the Purine Derivative of Formula (Ic") is the same as group D of the Purine Derivative of Formula (Ic').

In one embodiment, the Purine Derivatives of Formula (Ic) have the formula (Ic'), depicted above, wherein A, B, C and D are defined above for the Purine Derivatives of Formula (Ic), and wherein the Purine Derivatives of Formula (Ic') are substantially free of their corresponding enantiomer, represented by Formula (Ic").

In another embodiment, the Purine Derivatives of Formula (Ic) have the formula (Ic"), depicted above, wherein A, B, C and D are defined above for the Purine Derivatives of Formula (Ic), and wherein the Purine Derivatives of Formula (Ic") are substantially free of their corresponding enantiomer, represented by Formula (Ic').

In one embodiment, the Purine Derivatives of Formula (Ic) exist as a mixture of a Purine Derivative of Formula (Ic') and a Purine Derivative of Formula (Ic") wherein the amount of the Purine Derivative of Formula (Ic') exceeds the amount of the Purine Derivative of Formula (Ic").

In another embodiment, the Purine Derivatives of Formula (Ic) exist as a mixture of a Purine Derivative of Formula (Ic') and a Purine Derivative of Formula (Ic") wherein the amount of the Purine Derivative of Formula (Ic") exceeds the amount of the Purine Derivative of Formula (Ic').

In another embodiment, the Purine Derivatives of Formula (Ic) exist as a racemic mixture of a Purine Derivative of Formula (Ic') and a Purine Derivative of Formula (Ic").

In another embodiment, the Purine Derivatives of Formula (Ic) can exist in the form of a single enantiomer, for example, that depicted by either formula (Icc'0 or (Icc"):

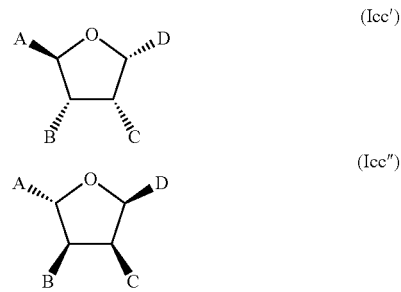

wherein A, B, C and D are defined above for the Purine Derivatives of Formula (Ic).

A Purine Derivative of Formula (Icc') is the corresponding opposite enantiomer of a Purine Derivative of Formula (Icc") when group A of the Purine Derivative of Formula (Icc'0 is the same as group A of the Purine Derivative of Formula (Icc") and when group D of the Purine Derivative of Formula (Icc') is the same as group D of the Purine Derivative of Formula (Icc").

A Purine Derivative of Formula (Icc") is the corresponding opposite enantiomer of a Purine Derivative of Formula (Icc') when group A of the Purine Derivative of Formula (Icc") is the same as group A of the Purine Derivative of Formula (Icc') and when group D of the Purine Derivative of Formula (Icc") is the same as group D of the Purine Derivative of Formula (Icc').

In one embodiment, the Purine Derivatives of Formula (Ic) have the formula (Icc'), depicted above, wherein A, B, C and D are defined above for the Purine Derivatives of Formula (Ic), and wherein the Purine Derivatives of Formula (Icc') are substantially free of their corresponding opposite enantiomer.

In another embodiment, the Purine Derivatives of Formula (Ic) have the formula (Icc"), depicted above, wherein A, B, C and D are defined above for the Purine Derivatives of Formula (Ic), and wherein the Purine Derivatives of Formula (Icc") are substantially free of their corresponding opposite enantiomer.

In another embodiment, the Purine Derivatives of Formula (Ic) exist as a mixture of a Purine Derivative of Formula (Icc') and a Purine Derivative of Formula (Icc") wherein the amount of the Purine Derivative of Formula (Icc') exceeds the amount of the Purine Derivative of Formula (Icc").

In a further embodiment, the Purine Derivatives of Formula (Ic) exist as a mixture of a Purine Derivative of Formula (Icc') and a Purine Derivative of Formula (Icc") wherein the amount of the Purine Derivative of Formula (Icc") exceeds the amount of the Purine Derivative of Formula (Icc').

In another embodiment, the Purine Derivatives of Formula (Ic) exist as a racemic mixture of a Purine Derivative of Formula (Icc') and a Purine Derivative of Formula (Icc").

A Purine Derivative of Formula (Icc') is the corresponding other anomer of a Purine Derivative of Formula (Ic') when group A of the Purine Derivative of Formula (Icc') is the same as group A of the Purine Derivative of Formula (Ic') and when group D of the Purine Derivative of Formula (Icc') is the same as group D of the Purine Derivative of Formula (Ic').

A Purine Derivative of Formula (Ic') is the corresponding other anomer of a Purine Derivative of Formula (Icc') when group A of the Purine Derivative of Formula (Ic') is the same as group A of the Purine Derivative of Formula (Icc') and when group D of the Purine Derivative of Formula (Ic') is the same as group D of the Purine Derivative of Formula (Icc').

A Purine Derivative of Formula (Icc") is the corresponding other anomer of a Purine Derivative of Formula (Ic") when group A of the Purine Derivative of Formula (Icc") is the same as group A of the Purine Derivative of Formula (Ic") and when group D of the Purine Derivative of Formula (Icc") is the same as group D of the Purine Derivative of Formula (Ic").

A Purine Derivative of Formula (Ic") is the corresponding other anomer of a Purine Derivative of Formula (Icc") when group A of the Purine Derivative of Formula (Ic") is the same as group A of the Purine Derivative of Formula (Icc") and when group D of the Purine Derivative of Formula (Ic") is the same as group D of the Purine Derivative of Formula (Icc").

In one embodiment, the Purine Derivatives of Formula (Ic) have the formula (Icc'), depicted above, wherein A, B, C and D are defined above for the Purine Derivatives of Formula (Ic), and wherein the Purine Derivatives of Formula (Icc') are substantially free of their corresponding other anomer.

In another embodiment, the Purine Derivatives of Formula (Ic) have the formula (Icc"), depicted above, wherein A, B, C and D are defined above for the Purine Derivatives of Formula (Ic), and wherein the Purine Derivatives of Formula (Icc") are substantially free of their corresponding other anomer.

In one embodiment, the Purine Derivatives of Formula (Ic) have the formula (Ic'), depicted above, wherein A, B, C and D are defined above for the Purine Derivatives of Formula (Ic), and wherein the Purine Derivatives of Formula (Ic') are substantially free of their corresponding other anomer.

In another embodiment, the Purine Derivatives of Formula (Ic) have the formula (Ic"), depicted above, wherein A, B, C and D are defined above for the Purine Derivatives of Formula (Ic), and wherein the Purine Derivatives of Formula (Ic") are substantially free of their corresponding other anomer.

In one embodiment, the Purine Derivatives of Formula (Ic) exist as a mixture of a Purine Derivative of Formula (Ic') and a Purine Derivative of Formula (Icc') wherein the amount of the Purine Derivative of Formula (Ic') exceeds the amount of the Purine Derivative of Formula (Icc').

In another embodiment, the Purine Derivatives of Formula (Ic) exist as a mixture of a Purine Derivative of Formula (Ic') and a Purine Derivative of Formula (Icc') wherein the amount of the Purine Derivative of Formula (Icc') exceeds the amount of the Purine Derivative of Formula (Ic').

In another embodiment, the Purine Derivatives of Formula (Ic) exist as an equimolar mixture of a Purine Derivative of Formula (Ic') and a Purine Derivative of Formula (Icc').

In one embodiment, the Purine Derivatives of Formula (Ic) exist as a mixture of a Purine Derivative of Formula (Ic") and a Purine Derivative of Formula (Icc") wherein the amount of the Purine Derivative of Formula (Ic") exceeds the amount of the Purine Derivative of Formula (Icc").

In another embodiment, the Purine Derivatives of Formula (Ic) exist as a mixture of a Purine Derivative of Formula (Ic") and a Purine Derivative of Formula (Icc") wherein the amount of the Purine Derivative of Formula (Icc") exceeds the amount of the Purine Derivative of Formula (Ic").

In another embodiment, the Purine Derivatives of Formula (Ic) exist as an equimolar mixture of a Purine Derivative of Formula (Ic") and a Purine Derivative of Formula (Icc").

5.2.4 The Purine Derivatives of Formula (Id)

As stated above, the present invention encompasses Purine Derivatives having the Formula (Id):

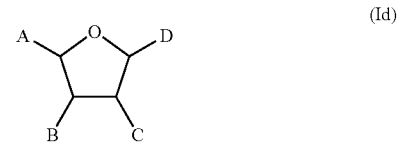

(Id)

wherein A, B, C and D are defined above for the Purine Derivatives of Formula (Id), and A and B are trans with respect to each other; B and C are cis with respect to each other; and C and D are cis or trans with respect to each other.

In one embodiment, $R^1$ is —H.

In another embodiment, $R^1$ is —$C_1$-$C_{10}$ alkyl.

In a specific embodiment, $R^1$ is ethyl.

In another embodiment, $R^1$ is -aryl or —$(CH_2)_n$-aryl.

In another embodiment, $R^1$ is —$C_3$-$C_8$ monocyclic cycloalkyl.

In another embodiment, $R^1$ is —$C_3$-$C_8$ monocyclic cycloalkenyl.

In another embodiment, $R^1$ is —$C_8$-$C_{12}$ bicyclic cycloalkyl or —$C_8$-$C_{12}$ bicyclic cycloalkenyl.

In one embodiment, $R^2$ is —CN.

In another embodiment, $R^2$ is —NHC(O)$OR^4$ or —NHC(O)$NHR^4$.

In another embodiment, $R^2$ is —NHNHC(O)$R^4$, —NHNHC(O)$OR^4$ or —NHNHC(O)$NHR^4$.

In another embodiment, $R^2$ is —NH—N=C($R^5$)$R^6$.

In still another embodiment, $R^2$ is —NH—N=CH—$C_3$-$C_8$ monocyclic cycloalkenyl.

In another embodiment, $R^2$ is —NH—N=CH-phenylene-$(CH_2)_m$COOH.

In a further embodiment, $R^2$ is —NH—N=CH-phenylene-$(CH_2)_m$—COO—($C_1$-$C_{10}$ alkyl).

In another embodiment, $R^2$ is —NH—N=CH-phenylene-$(CH_2)_m$—COO-(3- to 7-membered monocyclic heterocycle).

In one embodiment, $R^3$ is —$C_1$-$C_{10}$ alkyl.

In another embodiment, $R^3$ is -aryl.

In another embodiment, $R^3$ is -3- to 7-membered monocyclic heterocycle.

In still another embodiment, $R^3$ is -8- to 12-membered bicyclic heterocycle.

In yet another embodiment, $R^3$ is —$C_3$-$C_8$ monocyclic cycloalkyl.

In a further embodiment, $R^3$ is —$C_8$-$C_{12}$ bicyclic cycloalkyl or —$C_8$-$C_{12}$ bicyclic cycloalkenyl.

In a specific embodiment, $R^3$ is methyl.

In another specific embodiment, $R^3$ is ethyl.

In one embodiment, $R^1$ is —H and $R^3$ is —$C_1$-$C_{10}$ alkyl.

In a specific embodiment, $R^1$ is —H and $R^3$ is ethyl.

In another embodiment, $R^1$ is —$C_1$-$C_{10}$ alkyl and $R^3$ is —$C_1$-$C_{10}$ alkyl.

In a specific embodiment, $R_1$ and $R^3$ are each ethyl.

In one embodiment, $R^1$ is —H, $R^2$ is —NH—N=C($R^5$)$R^6$, and $R^3$ is —$C_1$-$C_{10}$ alkyl.

In a specific embodiment, $R^1$ is —H, $R^2$ is —NH—N=C($R^5$)$R^6$, and $R^3$ is ethyl.

In another specific embodiment, $R^2$ is —H and is $R^3$ is ethyl.

In one embodiment, $R^1$ is —H, $R^2$ is —CN, and $R^3$ is —$C_1$-$C_{10}$ alkyl.

In another embodiment, $R^1$ is —$C_1$-$C_{10}$ alkyl, $R^2$ is —CN, and $R^3$ is —$C_1$-$C_{10}$ alkyl.

In still another embodiment, $R^1$ is —$C_1$-$C_{10}$ alkyl, $R^2$ is —CN and $R^3$ is -methyl.

In a further embodiment, $R^1$ is—methyl, $R^2$ is —CN and $R^3$ is —$C_1$-$C_{10}$ alkyl.

In one embodiment, C and D are cis with respect to each other.

In another embodiment, C and D are trans with respect to each other.

The present invention also provides compositions comprising an effective amount of a Purine Derivative of Formula (Id) and a physiologically acceptable vehicle.

The invention further provides Purine Derivatives of Formula (Id) that are in isolated and purified form.

The invention still further provides methods for treating or preventing a Condition, comprising administering an effective amount of a Purine Derivative of Formula (Id) to a subject in need thereof.

The Purine Derivatives of Formula (Id) can exist in the form of a single enantiomer, for example, that depicted by either the Formula (Id') or Formula (Id"):

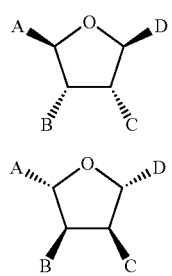

wherein A, B, C and D are defined above for the Purine Derivatives of Formula (Id).

A Purine Derivative of Formula (Id') is the corresponding opposite enantiomer of a Purine Derivative of Formula (Id") when group A of the Purine Derivative of Formula (Id') is the same as group A of the Purine Derivative of Formula (Id") and when group D of the Purine Derivative of Formula (Id') is the same as group D of the Purine Derivative of Formula (Id").

A Purine Derivative of Formula (Id") is the corresponding opposite enantiomer Io of a Purine Derivative of Formula (Id') when group A of the Purine Derivatives of Formula (Id") is the same as group A of the Purine Derivative of Formula (Id') and when group D of the Purine Derivative of Formula (Id") is the same as group D of the Purine Derivative of Formula (Id').

In one embodiment, the Purine Derivatives of Formula (Id) have the formula (Id'), depicted above, wherein A, B, C and D are defined above for the Purine Derivatives of Formula (Id), and wherein the Purine Derivatives of Formula (Id') are substantially free of their corresponding enantiomer, represented by Formula (Id").

In another embodiment, the Purine Derivatives of Formula (Id) have the formula (Id"), depicted above, wherein A, B, C and D are defined above for the Purine Derivatives of Formula (Id), and wherein the Purine Derivatives of Formula (Id") are substantially free of their corresponding enantiomer, represented by Formula (Id').

In one embodiment, the Purine Derivatives of Formula (Id) exist as a mixture of a Purine Derivative of Formula (Id') and a Purine Derivative of Formula (Id") wherein the amount of the Purine Derivative of Formula (Id') exceeds the amount of the Purine Derivative of Formula (Id").

In another embodiment, the Purine Derivatives of Formula (Id) exist as a mixture of a Purine Derivative of Formula (Id') and a Purine Derivative of Formula (Id") wherein the amount of the Purine Derivative of Formula (Id") exceeds the amount of the Purine Derivative of Formula (Id').

In another embodiment, the Purine Derivatives of Formula (Id) exist as a racemic mixture of a Purine Derivative of Formula (Id') and a Purine Derivative of Formula (Id").

In another embodiment, the Purine Derivatives of Formula (Id) can exist in the form of a single enantiomer, for example, that depicted by either formula (Idd') or (Idd"):

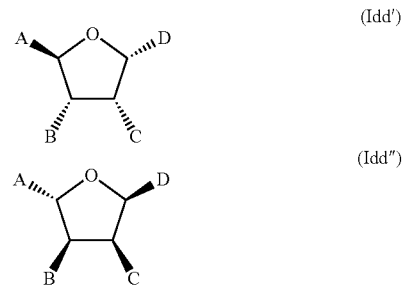

wherein A, B, C and D are defined above for the Purine Derivatives of Formula (Id).

A Purine Derivative of Formula (Idd') is the corresponding opposite enantiomer of a Purine Derivative of Formula (Idd") when group A of the Purine Derivative of Formula (Idd') is the same as group A of the Purine Derivative of Formula (Idd") and when group D of the Purine Derivative of Formula (Idd') is the same as group D of the Purine Derivative of Formula (Idd").

A Purine Derivative of Formula (Idd") is the corresponding opposite enantiomer of a Purine Derivative of Formula (Idd') when group A of the Purine Derivative of Formula (Idd") is the same as group A of the Purine Derivative of Formula (Idd')

and when group D of the Purine Derivative of Formula (Idd") is the same as group D of the Purine Derivative of Formula (Idd').

In one embodiment, the Purine Derivatives of Formula (Id) have the formula (Idd'), depicted above, wherein A, B, C and D are defined above for the Purine Derivatives of Formula (Id), and wherein the Purine Derivatives of Formula (Idd') are substantially free of their corresponding opposite enantiomer.

In another embodiment, the Purine Derivatives of Formula (Id) have the formula (Idd"), depicted above, wherein A, B, C and D are defined above for the Purine Derivatives of Formula (Id), and wherein the Purine Derivatives of Formula (Idd") are substantially free of their corresponding opposite enantiomer.

In another embodiment, the Purine Derivatives of Formula (Id) exist as a mixture of a Purine Derivative of Formula (Idd') and a Purine Derivative of Formula (Idd") wherein the amount of the Purine Derivative of Formula (Idd') exceeds the amount of the Purine Derivative of Formula (Idd").

In a further embodiment, the Purine Derivatives of Formula (Id) exist as a mixture of a Purine Derivative of Formula (Idd') and a Purine Derivative of Formula (Idd") wherein the amount of the Purine Derivative of Formula (Idd") exceeds the amount of the Purine Derivative of Formula (Idd').

In another embodiment, the Purine Derivatives of Formula (Id) exist as a racemic mixture of a Purine Derivative of Formula (Idd') and a Purine Derivative of Formula (Idd").

A Purine Derivative of Formula (Idd') is the corresponding other anomer of a Purine Derivative of Formula (Id') when group A of the Purine Derivative of Formula (Idd') is the same as group A of the Purine Derivative of Formula (Ib') and when group D of the Purine Derivative of Formula (Idd') is the same as group D of the Purine Derivative of Formula (Id').

A Purine Derivative of Formula (Id') is the corresponding other anomer of a Purine Derivative of Formula (Idd') when group A of the Purine Derivative of Formula (Id') is the same as group A of the Purine Derivative of Formula (Idd') and when group D of the Purine Derivative of Formula (Id') is the same as group D of the Purine Derivative of Formula (Idd').

A Purine Derivative of Formula (Idd") is the corresponding other anomer of a Purine Derivative of Formula (Id") when group A of the Purine Derivative of Formula (Idd") is the same as group A of the Purine Derivative of Formula (Id") and when group D of the Purine Derivative of Formula (Idd") is the same as group D of the Purine Derivative of Formula (Id").

A Purine Derivative of Formula (Id") is the corresponding other anomer of a Purine Derivative of Formula (Idd") when group A of the Purine Derivative of Formula (Id") is the same as group A of the Purine Derivative of Formula (Idd") and when group D of the Purine Derivative of Formula (Id") is the same as group D of the Purine Derivative of Formula (Idd").

In one embodiment, the Purine Derivatives of Formula (Id) have the formula (Idd'), depicted above, wherein A, B, C and D are defined above for the Purine Derivatives of Formula (Id), and wherein the Purine Derivatives of Formula (Idd') are substantially free of their corresponding other anomer.

In another embodiment, the Purine Derivatives of Formula (Id) have the formula (Idd"), depicted above, wherein A, B, C and D are defined above for the Purine Derivatives of Formula (Id), and wherein the Purine Derivatives of Formula (Idd") are substantially free of their corresponding other anomer.

In one embodiment, the Purine Derivatives of Formula (Id) have the formula (Id'), depicted above, wherein A, B, C and D are defined above for the Purine Derivatives of Formula (Id), and wherein the Purine Derivatives of Formula (Id') are substantially free of their corresponding other anomer.

In another embodiment, the the Purine Derivatives of Formula (Id) have the formula (Id'), depicted above, wherein A, B, C and D are defined above for the Purine Derivatives of Formula (Id), $R^1$ is —$C_1$-$C_{10}$ alkyl, $R^2$ is —CN, $R^3$ is —$C_1$-$C_{10}$ alkyl, and wherein the Purine Derivatives of Formula (Id') are substantially free of their corresponding other anomer.

In another embodiment, the Purine Derivatives of Formula (Id) have the formula (Id"), depicted above, wherein A, B, C and D are defined above for the Purine Derivatives of Formula (Id), and wherein the Purine Derivatives of Formula (Id") are substantially free of their corresponding other anomer.

In one embodiment, the Purine Derivatives of Formula (Id) exist as a mixture of a Purine Derivative of Formula (Id') and a Purine Derivative of Formula (Idd') wherein the amount of the Purine Derivative of Formula (Id') exceeds the amount of the Purine Derivative of Formula (Idd').

In another embodiment, the Purine Derivatives of Formula (Id) exist as a mixture of a Purine Derivative of Formula (Id') and a Purine Derivative of Formula (Idd') wherein the amount of the Purine Derivative of Formula (Idd') exceeds the amount of the Purine Derivative of Formula (Id').

In another embodiment, the Purine Derivatives of Formula (Id) exist as an equimolar mixture of a Purine Derivative of Formula (Id') and a Purine Derivative of Formula (Idd').

In one embodiment, the Purine Derivatives of Formula (Id) exist as a mixture of a Purine Derivative of Formula (Id") and a Purine Derivative of Formula (Idd") wherein the amount of the Purine Derivative of Formula (Id") exceeds the amount of the Purine Derivative of Formula (Idd").

In another embodiment, the Purine Derivatives of Formula (Id) exist as a mixture of a Purine Derivative of Formula (Id") and a Purine Derivative of Formula (Idd") wherein the amount of the Purine Derivative of Formula (Idd") exceeds the amount of the Purine Derivative of Formula (Id").

In another embodiment, the Purine Derivatives of Formula (Id) exist as an equimolar mixture of a Purine Derivative of Formula (Id") and a Purine Derivative of Formula (Idd").

Illustrative examples of the compounds of Formula (Id') include the compounds listed below:

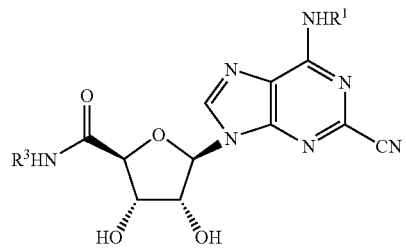

| Compound | $R^1$ | $R^3$ |
| --- | --- | --- |
| 50 | —H | —$CH_2CH_3$ |
| 51 | —H | —$CH_3$ |
| 52 | —$CH_2CH_3$ | —$CH_2CH_3$ |
| 53 | —$CH_2CH_3$ | —$CH_3$ |
| 54 | —$CH_3$ | —$CH_3$ |
| 55 | —$CH_3$ | —$CH_2CH_3$ | and pharmaceutically acceptable salts thereof.

Another illustrative compound of formula (Id') is the following compound:

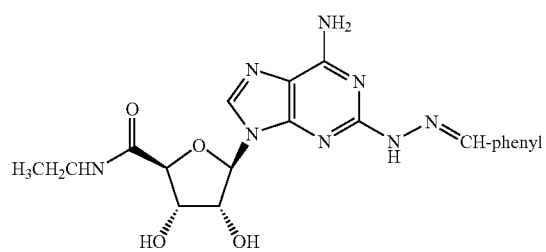

56 and pharmaceutically acceptable salts thereof.

The Purine Derivatives may contain one or more chiral centers. Where no stereochemistry is indicated in a chemical structure or name, the structure or name encompasses both enantiomers, its racemate and all mixtures thereof.

Additionally, the Purine Derivatives may contain one or more double bonds. Where no particular geometric isomer of a double bond is indicated in a chemical structure or name, the structure or name encompasses encompass the double bond's cis isomer, the trans isomer and all mixtures thereof.

5.3 Methods for Making the Purine Derivatives

The Purine Derivatives can be made according to methods well-known to one skilled in the art of organic chemistry or by using the synthetic procedures outlined below in Schemes 1-6.

Scheme 1 shows methods for making nucleoside intermediates that are useful for making the Purine Derivatives of Formulas (Ia), (Ib), (Ic) and (Id).

Scheme 1

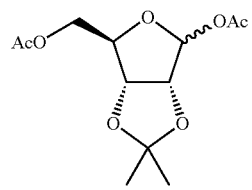

1

+

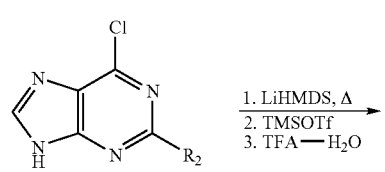

2

1. LiHMDS, Δ
2. TMSOTf
3. TFA—$H_2O$

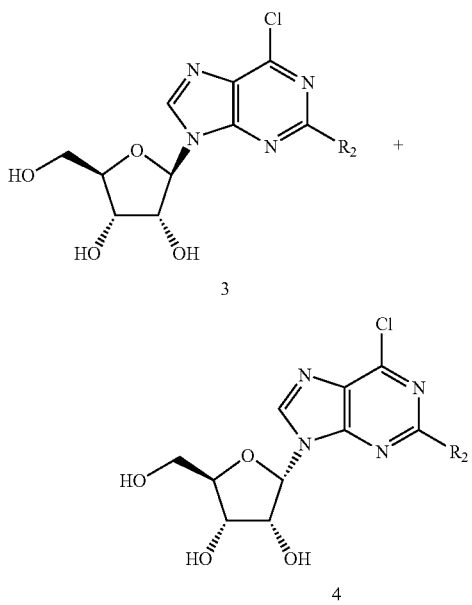

3

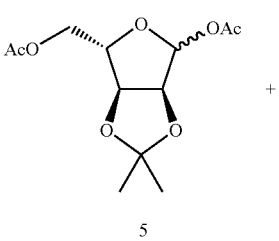

4

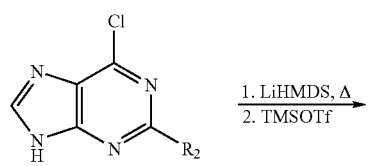

+

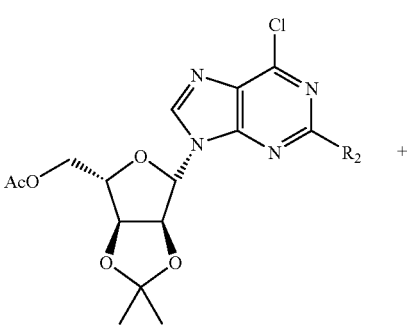

2

1. LiHMDS, Δ
2. TMSOTf

6

+

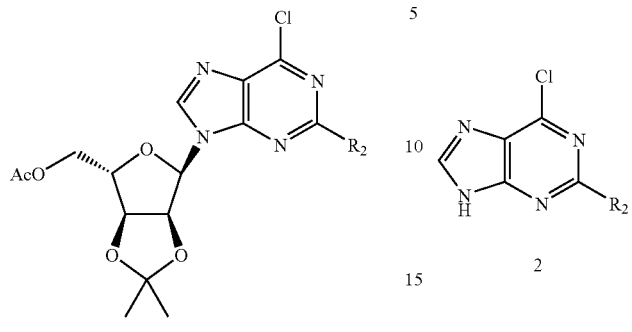

7

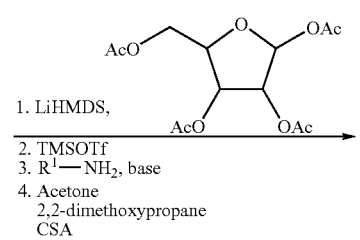

wherein R₂ is as defined above for the Purine Derivatives of Formulas (Ia), (Ib), (Ic) and (Id).

The protected ribose compound of Formula 1 can be coupled with a purine compound of Formula 2 using lithium hexamethyldisilazide and TMS triflate, followed by acetonide removal using TFA to provide nucleoside intermediates of Formula 3 and their corresponding other anomers of Formula 4. Similarly, the protected ribose tetraacetate of Formula 5 can be coupled with a compound of Formula 2 to provide protected acetyl nucleoside intermediates of Formula 6 and their corresponding other anomers of Formula 7.

Scheme 2 shows a method useful for making the adenosine intermediates of Formula 8 which are useful for making the Purine Derivatives of Formulas (Ia), (Ib), (Ic) and (Id).

Scheme 2

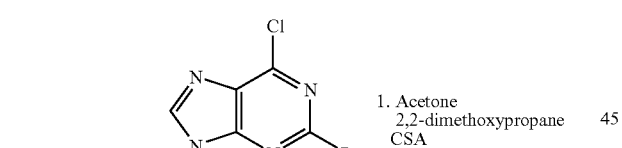

3a

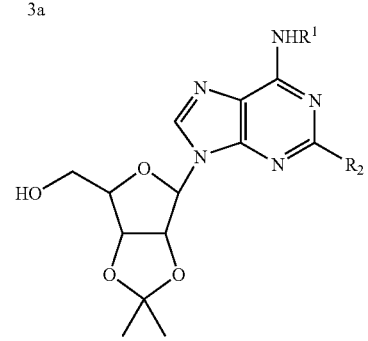

8 where $R^1$ and $R^2$ is defined above herein for the Purine Derivatives of Formulas (Ia)-(Id).

The 6-chloroadenosine derivative of formula 3a is converted to its 2',3'-acetonide using acetone and 2,2-dimethoxypropane in the presence of camphorsulfonic acid. The acetonide can then be further derviatized using an amine of formula $R^1$—$NH_2$ in the presence of base to provide compounds of formula 8.

Alternatively, a purine compound of Formula 2 can be coupled with a tetraacetate protected ribose compound of formula Z using lithium hexamethyldisilazide and TMS triflate. The resulting adduct can be protected as it's acetonide derivative using using acetone and 2,2-dimethoxypropane in the presence of camphorsulfonic acid to provide compounds of formula 8.

Scheme 3 illustrates a method useful for making the Purine Derivatives where $R^2$ is —NH—N=C($R^5$)$R^6$.

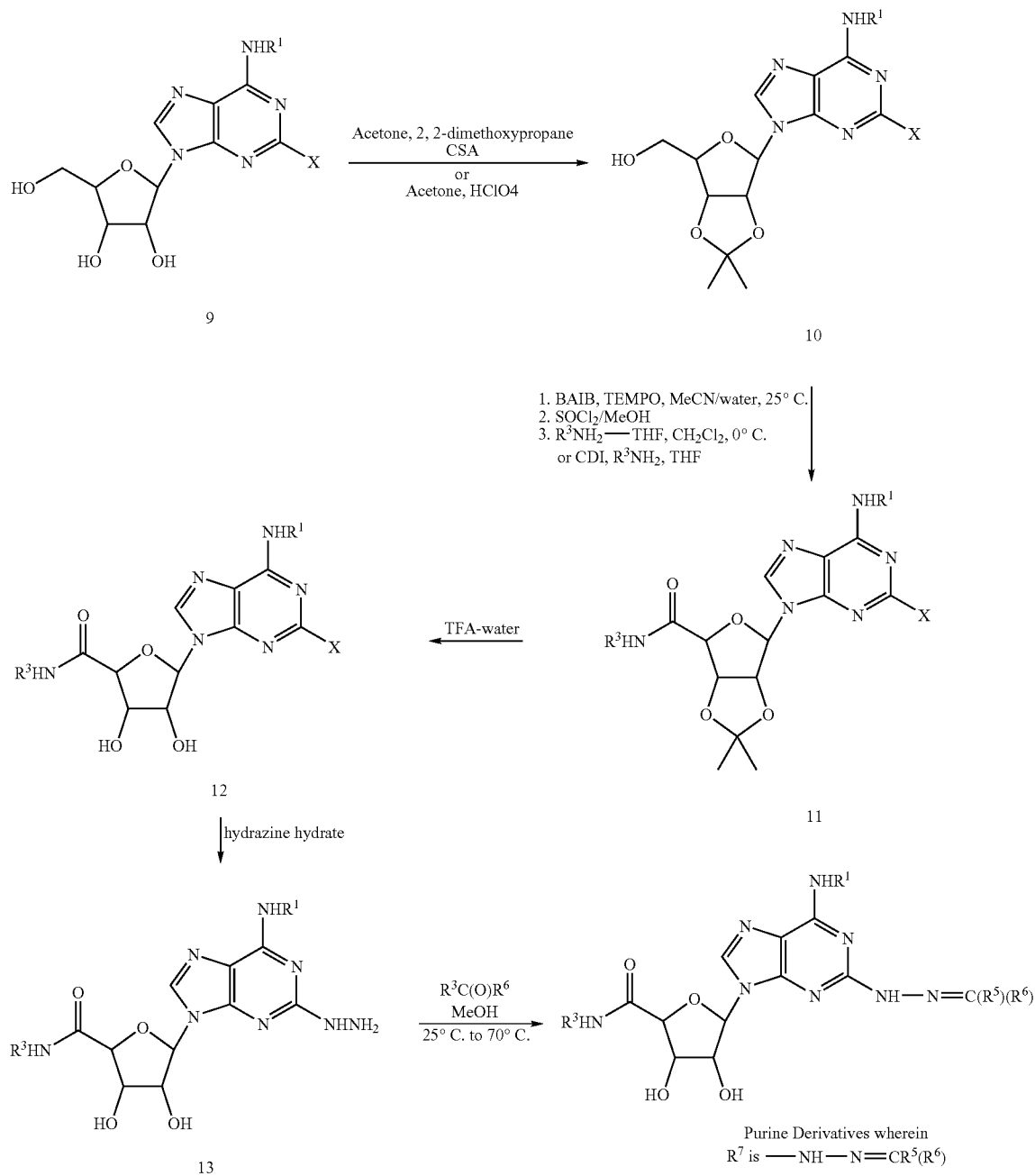

Scheme 3 wherein X is —Cl or —I, and $R^1$, $R^3$, $R^5$ and $R^6$ are as defined above herein for the Purine Derivatives.

The 2-chloroadenosine or 2-iodoadenosine derivatives of formula 9 are converted to their acetonide derivatives of formula 10 upon treatment with 2,2-dimethoxypropane in the presence of camphorsulfonic acid, or alternatively by treating with acetone in the presence of perchloric acid. The hydroxymethyl group of the compounds of formula 10 are then converted to the amides of formula 11 using a three-step procedure. The hydroxyl group of 10 is first oxidized using TEMPO (2,2,6,6-tetramethyl-1-piperidinyloxy, free radical) to provide the corresponding carboxylic acid intermediates, which are then converted to the corresponding acid chloride or ester intermediates using thionyl chloride in methanol. The acid chloride intermediates are then coupled with an amine of formula $R^3NH_2$ to provide the amide compounds of formula 11. The $NH_2$ group of the compounds of formula 11 can then optionally be derivatized by reacting with an electrophile of formula $R^1$-Z in the presence of base, or can be used as is in the next step if the target compound has $R^1$=H. The acetonide protecting group of the compounds of formula 11 are then removed using TFA to provide the 2',3'-dihydroxy compounds of formula 12 which can be derivatized at the 2-position to provide numerous classes of compounds. As specifically illustrated in Scheme 1, the compounds of formula 12 can be treated with hydrazine hydrate to provide the hydrazines of formula 13 which can subseqently be coupling with a ketone or aldehyde having the formula $R^5C(O)R^6$ to provide Purine Derivatives wherein $R^2$ is —NH—N=CR$^5$ (R$^6$).

Scheme 4 illustrates a method for making the Purine Derivatives wherein $R^2$ is —NHNHC(O)R$^4$, —NHNHC(O)OR$^4$ or —NHNHC(O)NHR$^4$.

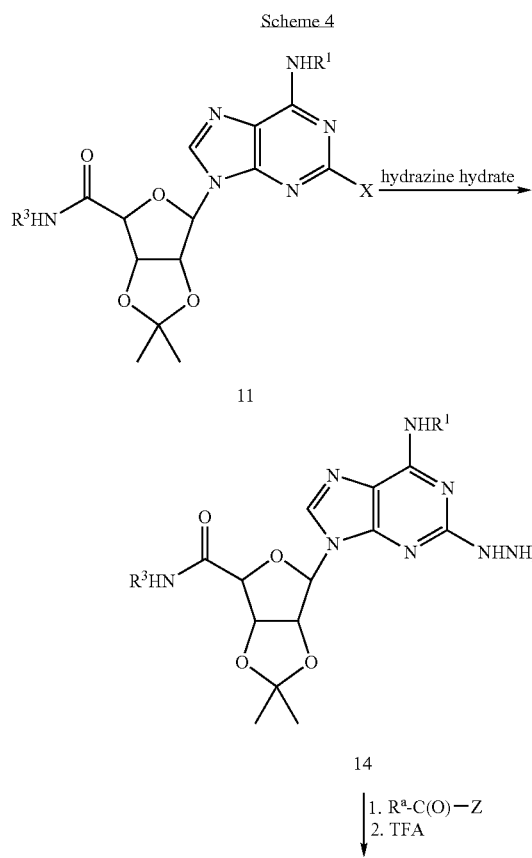

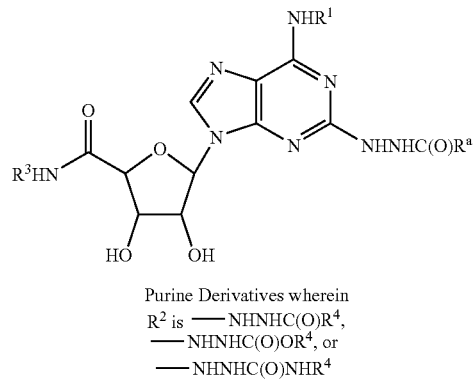

Purine Derivatives wherein
$R^2$ is —NHNHC(O)R$^4$,
—NHNHC(O)OR$^4$, or
—NHNHC(O)NHR$^4$ wherein X is —Cl or —I; $R^1$ and $R^3$ are as defined above herein for the Purine Derivatives of Formulas (Ia)-(Id); and $R^a$ is $R^4$, —OR$^4$ or —NHR$^4$.

2-Chloroadenosine or 2-iodoadenosine derivatives of formula 11 are reacted with hydrazine hydrate to provide the hydrazine compounds of formula 14. The hydrazine group of the compounds of formula 14 can then be coupled with a compound of formula $R^a$—C(O)-Z, then treated with TFA to provide the. Purine Derivatives where $R^2$ is —NHNHC(O)R$^4$, —NHNHC(O)OR$^4$ or —NHNHC(O)NHR$^4$.

Scheme 5 shows a method useful for making the Purine Derivatives where $R^2$ is —CN.

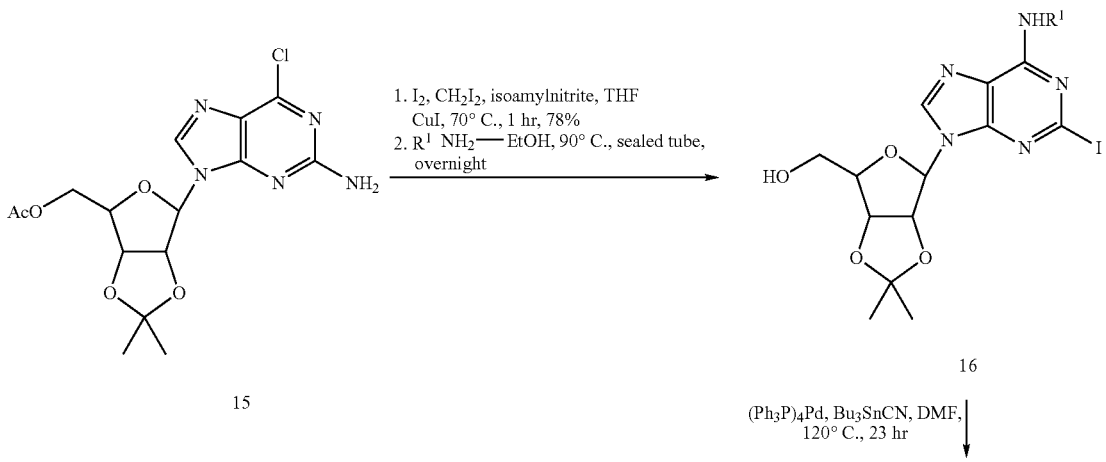

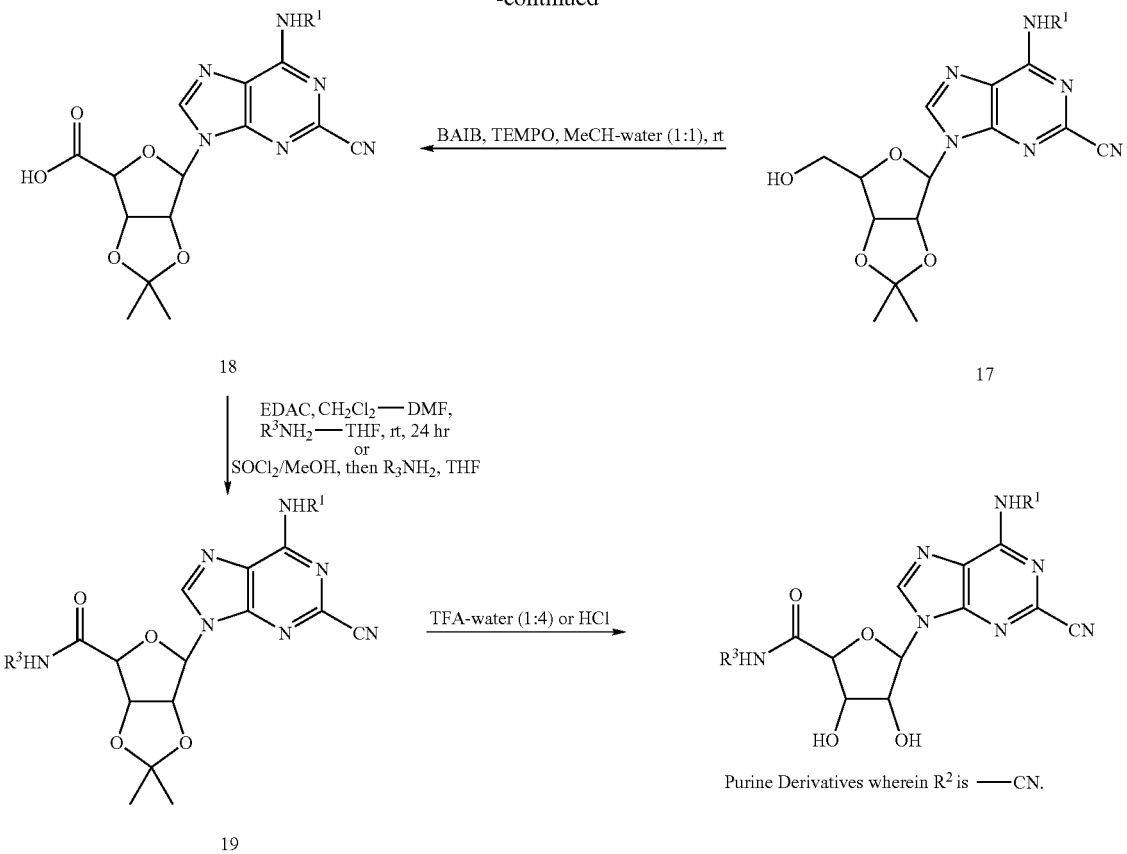

wherein R¹ and R³ are as defined above herein for the Purine Derivatives.

The 2-amino purinyl acetate of formula 15 is converted to its 2-iodo analog, which is then reacted with an amine of formula R¹NH₂ to provide the 2-iodo adenosine derviatives of formula 16. The compounds of formula 16 are then converted to their 2-cyano derivatives (17) upon Pd catalyzed cyanation of the aromatic iodide moiety of the compounds of formula 16. The free hydroxyl group of the compounds of formula 17 can be oxidized to the corresponding carboxylic acids of formula 18 using TEMPO. The carboxylic acids 18 can then be coupled with an amine having the formula R³NH₂ in the presence of EDAC (1-(3-dimethylaminopropyl)-3-ethylcarbodiimide hydrochloride) to provide the amides of formula 19 which are then treated with acid (TFA or HCl) to remove the acetonide group and provide Purine Derivatives wherein R² is —CN.

Scheme 6 shows a method for making the Purine Derivatives where R² is —NHC(O)OR⁴ or —NHC(O)NHR⁴.

Scheme 6

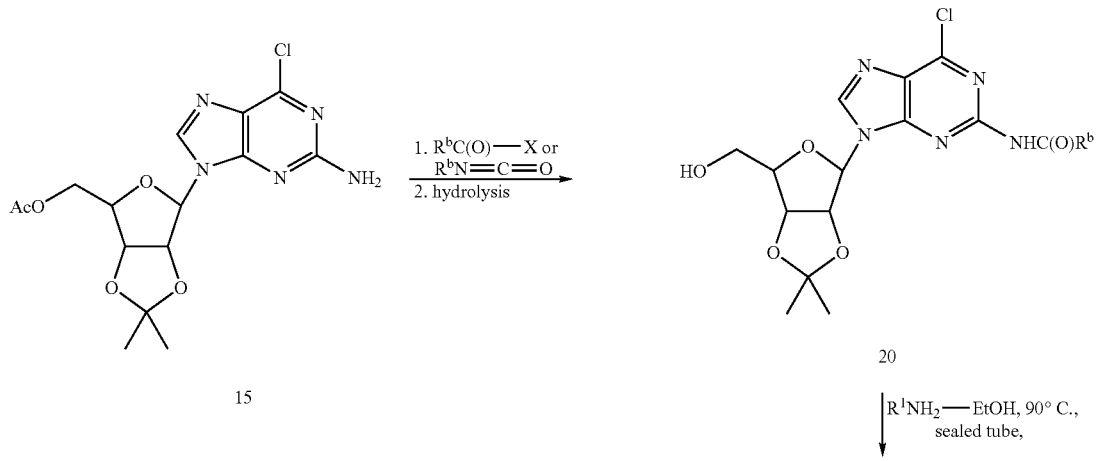

-continued

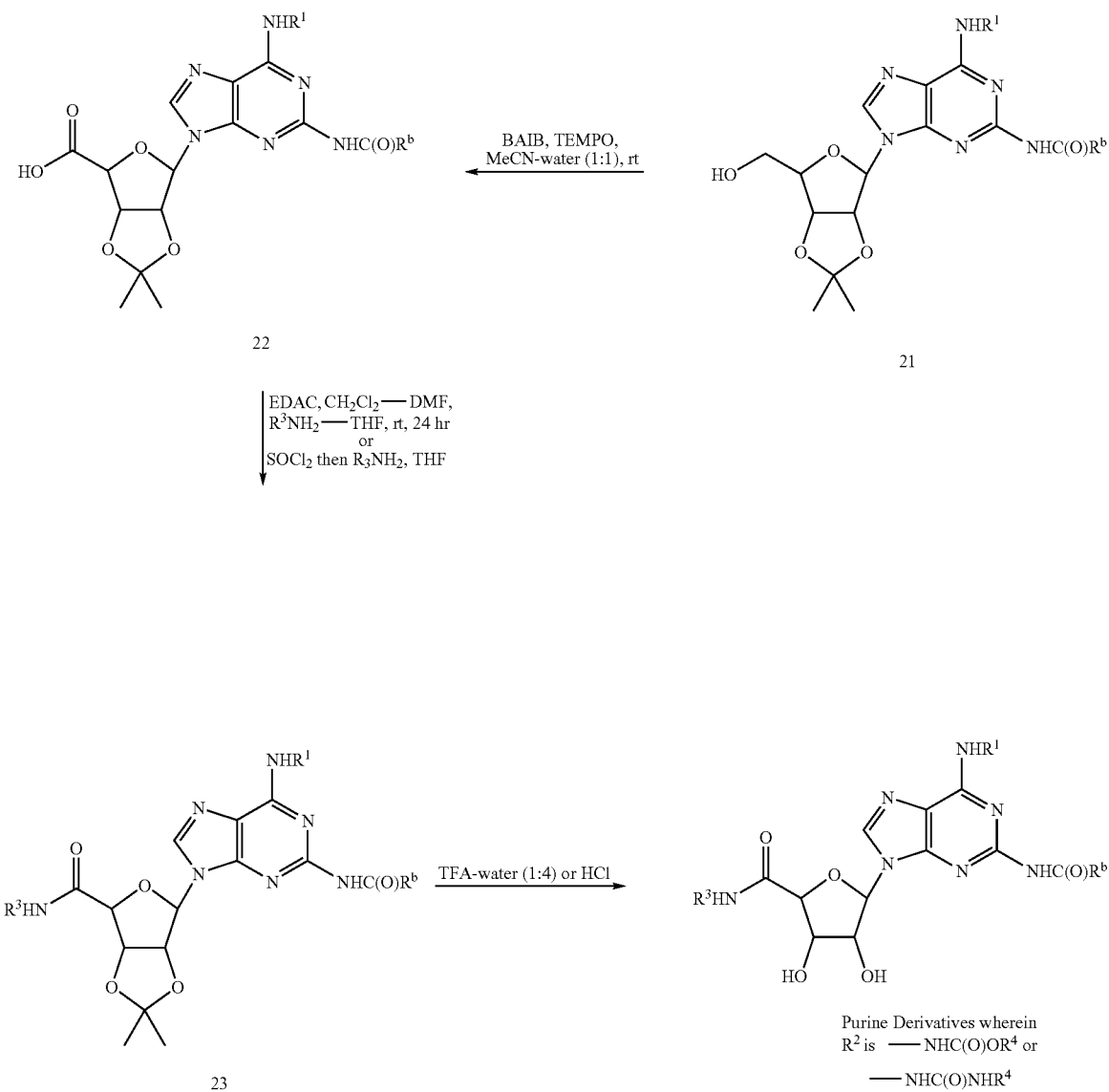

wherein $R^1$ and $R^3$ are as defined above herein for the Purine Derivatives; $R^b$ is —$R^4$, —$OR^4$, or —$NHR^4$; $R^4$ is defined as above for the Purine Derivatives of Formulas (Ia)-(Id); and X is —Cl or —Br.

The 2-amino group of the purinyl acetate of formula 15 is coupled with an acyl halide, haloformate, or halocarbamyl of formula $R^bC(O)$—X, then treated with potassium carbonate in methaol to provide the hydroxy compounds of formula 20. The chloro group of the compounds 20 is then reacted with an amine of formula $R^1$—$NH_2$ to provide the compounds of formula 21, which are oxidized using TEMPO to provide the carboxylic acid intermediates of formula 22. The carboxylic acids of formula 22 can then be coupled with an amine of formula $R^3NH_2$ to provide the carboxamido compounds of formula 23, then treated with acid to remove the acetonide group and provide the Purine Derivatives wherein $R^2$ is —NHC(O)$OR^4$ or —NHC(O)$NHR^4$.

Scheme 7 shows another method useful for making the Purine Derivatives where $R^2$ is —CN.

Scheme 7

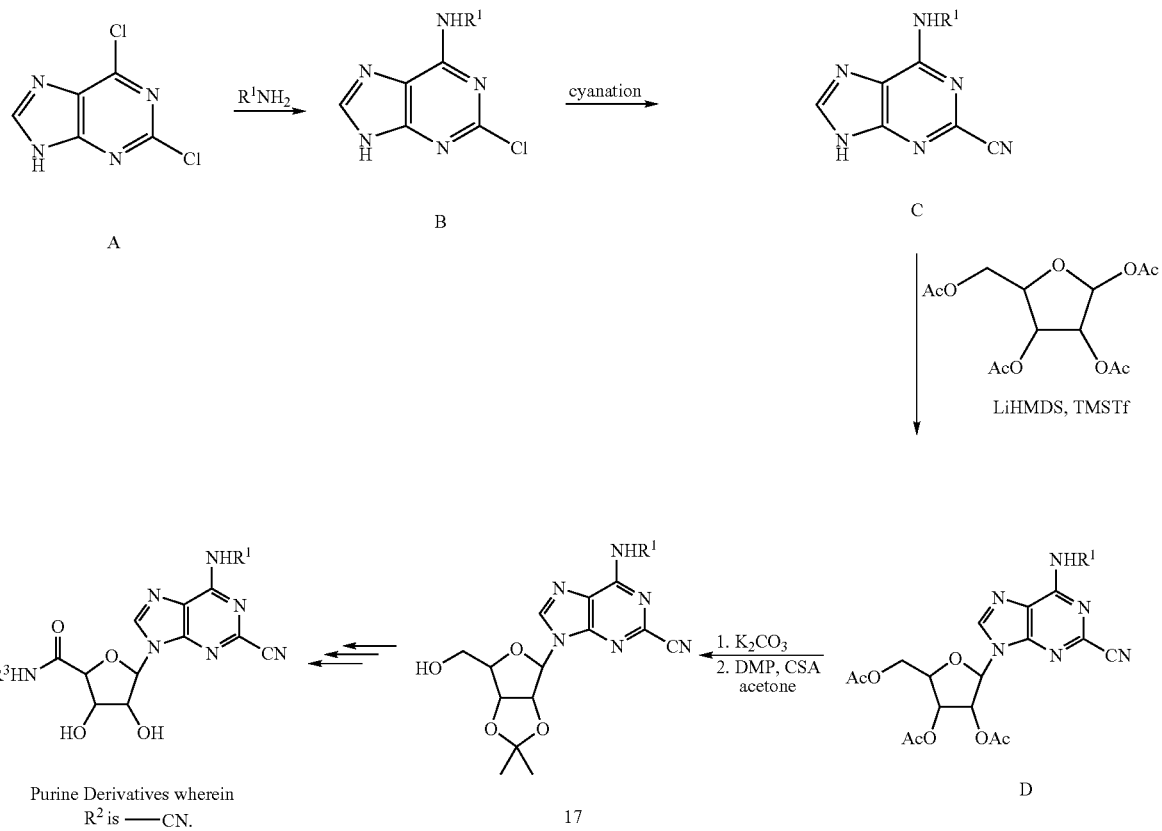

wherein $R^1$ and $R^3$ are as defined above herein for the Purine Derivatives. 2,6-dichloropurine (A) is reacted with an amine of formula $R^1NH_2$ to provide the corresponding amino compound of formula B. The 2-chloro group of B can then be converted to a nitrile using a palladium-catalyzed coupling reaction as described, for example, in Zapf, et al., *Chemical Communications*, 4:431-440 (2005), to provide a 2-cyano purinyl compound of formula C. The compound of formula C is then coupled with ribofuranose tetraacetate to provide a triacetate nucleoside compound of formula D. The acetate groups of D are subsequently hydrolyzed using, for example, potassium carbonate and the resultant 2',3'-diol is protected as its acetonide using 2,2-dimethoxypropane (DMP) and camphorsulfonic acid (CSA) in the presence of acetone, to provide a compound of formula 17, which can be further elaborated as described in Scheme 5 above to provide provide Purine Derivatives wherein $R^2$ is —CN.

Scheme 8 shows a method useful for making the Purine Derivatives where $R^2$ is —CN and wherein $R^1$ and $R^3$ are the same.

Scheme 8

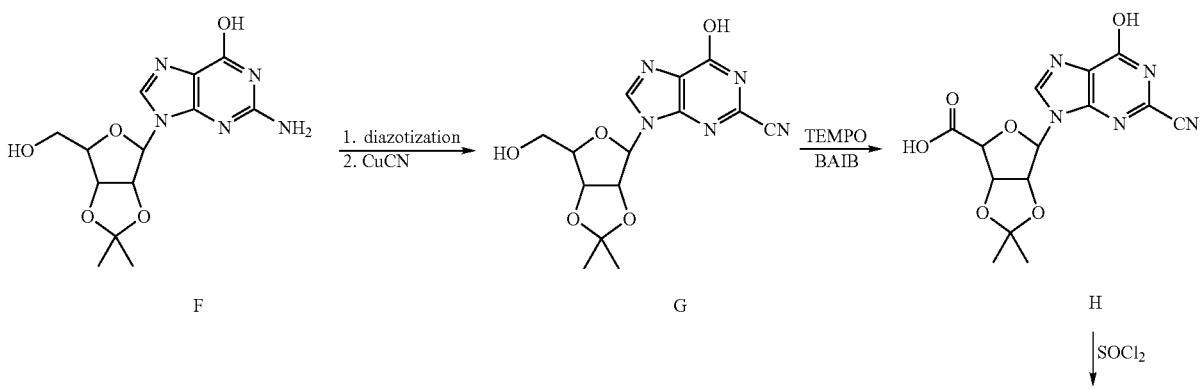

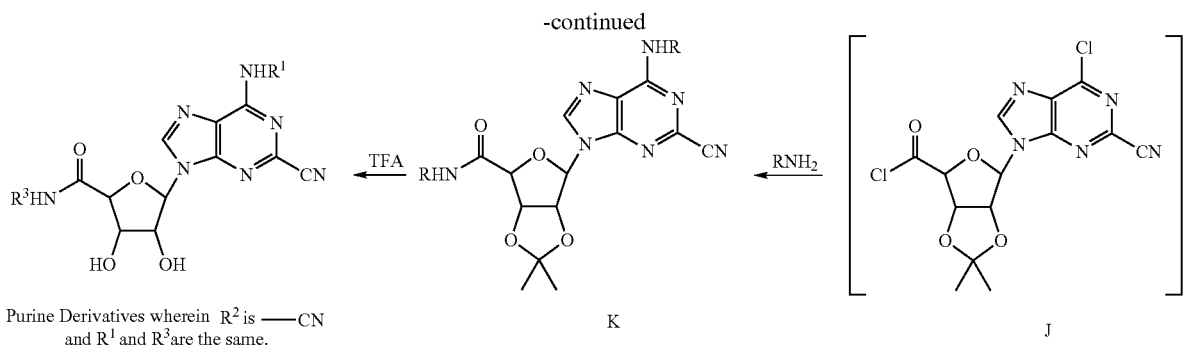

Purine Derivatives wherein $R^2$ is —CN and $R^1$ and $R^3$ are the same.

wherein $R^1$ and $R^3$ are as defined above herein for the Purine Derivatives.

The 2-amino group of the purinyl compound of formula F is diazotized using, for example, nitrous acid or an alkyl nitrite, and the resultant diazonium salt can then be reacted with CuCN to provide a 2-cyano purinyl compound of formula G. The 5'-hydroxy group of G is then oxidized to the corrsponding carboxylic acid H using TEMPO. The compound of formula H is then reacted with thionyl chloride to provide an intermediate 5',6'-dichloro compound of formula J, which is subsequently reacted with a stoichiometric excess of an amine of formula $RNH_2$ to provide a purinyl compound of formula K. The acetonide group of a compound of formula K can then be removed using TFA to provide Purine Derivatives wherein $R^2$ is —CN and wherein $R^1$ and $R^2$ are the same.

5.4 Therapeutic/Prophylactic Administration and Compositions of the Invention Due to their activity, the Purine Derivatives are advantageously useful in veterinary and human medicine. As described above, the Purine Derivatives are useful for treating or preventing a Condition in a subject in need thereof.

When administered to a subject, the Purine Derivatives can be administered as a component of a composition that comprises a physiologically acceptable carrier or vehicle. The present compositions, which comprise a Purine Derivative, can be administered orally. The Purine Derivatives can also be administered by any other convenient route, for example, by infusion or bolus injection, by absorption through epithelial (e.g., skin) or mucocutaneous linings (e.g., oral, rectal, and intestinal mucosa, etc.), or by inhalation, and can be administered together with another biologically active agent. Administration can be systemic or local. Various known delivery systems, including encapsulation in liposomes, microparticles, microcapsules, and capsules, can be used.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. In some instances, administration results in the release of the Purine Derivatives into the bloodstream. The mode of administration can be left to the discretion of the practitioner.

In one embodiment, the Purine Derivatives are administered orally.

In another embodiment, the Purine Derivatives are administered intravenously.

In another embodiment, the Purine Derivatives are administered topically.

In other embodiments, it can be desirable to administer the Purine Derivatives locally. This can be achieved, for example, and not by way of limitation, by local infusion during surgery, topical application, (e.g., directly to a wound or in conjunction with a wound dressing), by injection, by means of a catheter, by means of a suppository or enema, or by means of an implant, said implant being of a porous, non-porous, or gelatinous material, including membranes, such as sialastic membranes, or fibers.

In certain embodiments, it can be desirable to introduce the Purine Derivatives into the central nervous system, circulatory system or gastrointestinal tract by any suitable route, including intraventricular, intrathecal injection, paraspinal injection, epidural injection, enema, and by injection adjacent to a peripheral nerve. Intraventricular injection can be facilitated by an intraventricular catheter, for example, attached to a reservoir, such as an Ommaya reservoir.

Pulmonary administration can also be employed, e.g., by use of an inhaler of nebulizer, and formulation with an aerosolizing agent, or via perfusion in a fluorocarbon or synthetic pulmonary surfactant. In certain embodiments, the Purine Derivatives can be formulated as a suppository, with traditional binders and excipients such as triglycerides.

In another embodiment the Purine Derivatives can be delivered in a vesicle, in particular a liposome (see Langer, *Science* 249:1527-1533 (1990) and Treat or prevent et al., *Liposomes in the Therapy of Infectious Disease and Cancer* 317-327 and 353-365 (1989)).

In yet another embodiment the Purine Derivatives can be delivered in a controlled-release system or sustained-release system (see, e.g., Goodson, in Medical Applications of Controlled Release, supra, vol. 2, pp. 115-138 (1984)). Other controlled or sustained-release systems discussed in the review by Langer, *Science* 249:1527-1533 (1990) can be used. In one embodiment a pump can be used (Langer, *Science* 249:1527-1533 (1990); Sefton, *CRC Crit Ref. Biomed. Eng.* 14:201 (1987); Buchwald et al., *Surgery* 88:507 (1980); and Saudek et al., *N. Engl. J Med.* 321:574 (1989)). In another embodiment polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 2:61 (1983); Levy et al., *Science* 228:190 (1935); During et al., *Ann. Neural.* 25:351 (1989); and Howard et al., *J. Neurosurg.* 71:105 (1989)).

In yet another embodiment a controlled- or sustained-release system can be placed in proximity of a target of the Purine Derivatives, e.g., the spinal column, brain, colon, skin, heart, lung, or gastrointestinal tract, thus requiring only a fraction of the systemic dose.

The present compositions can optionally comprise a suitable amount of a physiologically acceptable excipient.

Such physiologically acceptable excipients can be liquids, such as water and oils, including those of petroleum, animal, vegetable, or synthetic origin, such as peanut oil, soybean oil, mineral oil, sesame oil and the like. The physiologically acceptable excipients can be saline, gum acacia, gelatin, starch paste, talc, keratin, colloidal silica, urea and the like. In addition, auxiliary, stabilizing, thickening, lubricating, and coloring agents can be used. In one embodiment the physiologically acceptable excipients are sterile when administered to a subject. Water is a particularly useful excipient when the Purine Derivative is administered intravenously. Saline solutions and aqueous dextrose and glycerol solutions can also be employed as liquid excipients, particularly for injectable solutions. Suitable physiologically acceptable excipients also include starch, glucose, lactose, sucrose, gelatin,. malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions. aerosols, sprays, suspensions, or any other form suitable for use. In one embodiment the composition is in the form of a capsule. Other examples of suitable physiologically acceptable excipients are described in *Remington's Pharmaceutical Sciences* 1447-1676 (Alfonso R. Gennaro eds., 19th ed. 1995), incorporated herein by reference.

In one embodiment the Purine Derivatives are formulated in accordance with routine procedures as a composition adapted for oral administration to human beings. Compositions for oral delivery can be in the form of tablets, lozenges, aqueous or oily suspensions, granules, powders, emulsions, capsules, syrups, or elixirs for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving a Purine Derivative are also suitable for orally administered compositions. In these latter platforms, fluid from the environment surrounding the capsule can be imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment the excipients are of pharmaceutical grade.

In another embodiment the Purine Derivatives can be formulated for intravenous administration. Typically, compositions for intravenous administration comprise sterile isotonic aqueous buffer. Where necessary, the compositions can also include a solubilizing agent. Compositions for intravenous administration can optionally include a local anesthetic such as lignocaine to lessen pain at the site of the injection. Generally, the ingredients are supplied either separately or mixed together in unit dosage form, for example, as a dry lyophilized powder or water-free concentrate in a hermetically sealed container such as an ampule or sachette indicating the quantity of active agent. Where the Purine Derivatives are to be administered by infusion, they can be dispensed, for example, with an infusion bottle containing sterile pharmaceutical grade water or saline. Where the Purine Derivatives are administered by injection, an ampule of sterile water for injection or saline can be provided so that the ingredients can be mixed prior to administration.

The Purine Derivatives can be administered by controlled-release or sustained-release means or by delivery devices that are well known to those of ordinary skill in the art. Such dosage forms can be used to provide controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled- or sustained-release.

Controlled- or sustained-release compositions can initially release an amount of a Purine Derivative that promptly produces the desired therapeutic or prophylactic effect, and gradually and continually release other amounts of the Purine Derivative to maintain this level of therapeutic or prophylactic effect over an extended period of time. To maintain a constant level of the Purine Derivative in the body, the Purine Derivative can be released from the dosage form at a rate that will replace the amount of Purine Derivative being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

The amount of the Purine Derivative that is effective for treating or preventing a Condition can be determined by standard clinical techniques. In addition, in vitro or in vivo assays can optionally be employed to help identify optimal dosage ranges. The precise dose to be employed can also depend on the route of administration, and the seriousness of the condition being treated and can be decided according to the judgment of a health-care practitioner. Suitable effective dosage amounts, however, range from about 10 micrograms to about 5 grams about every 4 h, although they are typically about 500 mg or less per every 4 hours. In one embodiment the effective dosage is about 0.01 mg, 0.5 mg, about 1 mg, about 50 mg, about 100 mg, about 200 mg, about 300 mg, about 400 mg, about 500 mg, about 600 mg, about 700 mg, about 800 mg, about 900 mg, about 1 g, about 1.2 g, about 1.4 g, about 1.6 g, about 1.8 g, about 2.0 g, about 2.2 g, about 2.4 g, about 2.6 g, about 2.8 g, about 3.0 g, about 3.2 g, about 3.4 g, about 3.6 g, about 3.8 g, about 4.0 g, about 4.2 g, about 4.4 g, about 4.6 g, about 4.8 g, and about 5.0 g, every 4 hours. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The number and frequency of dosages corresponding to a completed course of therapy can be determined according to the judgment of a health-care practitioner. The effective dosage amounts described herein refer to total amounts administered; that is, if more than one Purine Derivative is administered, the effective dosage amounts correspond to the total amount administered.

The amount of a Purine Derivative that is effective for treating or preventing a Condition typically ranges from about 0.01 mg/kg to about 100 mg/kg of body weight per day, in one embodiment, from about 0.1 mg/kg to about 50 mg/kg body weight per day, and in another embodiment, from about 1 mg/kg to about 20 mg/kg of body weight per day.

The Purine Derivatives can be assayed in vitro or in vivo for the desired therapeutic or prophylactic activity prior to use in humans.

The present methods for treating or preventing a Condition can further comprise administering another therapeutic agent to the subject being administered a Purine Derivative. In one embodiment the other therapeutic agent is administered in an effective amount.

Effective amounts of the other therapeutic agents are well known to those skilled in the art. However, it is well within the skilled artisan's purview to determine the other therapeutic agent's optimal effective amount range. In one embodiment of the invention, where, another therapeutic agent is administered to a subject, the effective amount of the Purine Derivative is less than its effective amount would be where the other therapeutic agent is not administered. In this case, without being bound by theory, it is believed that the Purine Derivatives and the other therapeutic agent act synergistically.

In one embodiment the other therapeutic agent is an anti-inflammatory agent. Examples of useful anti-inflammatory agents include, but are not limited to, adrenocorticosteroids, such as cortisol, cortisone, fluorocortisone, prednisone, prednisolone, 6a-methylprednisolone, triamcinolone, betamethasone, and dexamethasone; and non-steroidal anti-inflammatory agents (NSAIDs), such as aspirin, acetaminophen, indomethacin, sulindac, tolmetin, diclofenac, ketorolac, ibuprofen, naproxen, flurbiprofen, ketoprofen, fenoprofen, oxaprozin, mefenamic acid, meclofenamic acid, piroxicam, meloxicam, nabumetone, rofecoxib, celecoxib, etodolac, and nimesulide.

In a further embodiment the other therapeutic agent is an anti-cardiovascular-disease agent. Examples of useful anti-cardiovascular-disease agents include, but are not limited to, carnitine; thiamine; and muscarinic receptor antagonists, such as atropine, scopolamine, homatropine, tropicamide, pirenzipine, ipratropium, tiotropium, and tolterodine.

In another embodiment the other therapeutic agent is an anti-emetic agent. Suitable anti-emetic agents include, but are not limited to, metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine and tropisetron.

In another embodiment, the other therapeutic agent may be an hematopoietic colony stimulating. factor. Suitable hematopoietic colony stimulating factors include, but are not limited to, filgrastim, sargramostim, molgramostim and epoietin alfa.

In still another embodiment, the other therapeutic agent may be an analgesic agent. In one embodiment, the analgesic agent is an opioid analgesic. In another embodiment, the analgesic ia a non-opioid analgesic agent. Suitable opioid analgesic agents include, but are not limited to, morphine, heroin, codeine, nalbuphine, butorphanol, xylazine, metedomidine,hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanyl, sufentanil, alfentanil, remifentanil, levorphanol, dextromethorphan, phenazocine, pentazocine, cyclazocine, methadone, isomethadone and propoxyphene. Suitable non-opioid analgesic agents include, but are not limited to, acetaminophen, aspirin, celecoxib, rofecoxib, diclofinac, diflusinal, etodolac, fenoprofen, flurbiprofen, ibuprofen, ketoprofen, indomethacin, ketorolac, meclofenamate, mefanamic acid, nabumetone, naprosin, naproxen, piroxicam and sulindac.

In still another embodiment, the other therapeutic agent may be an anxiolytic agent. Suitable anxiolytic agents include, but are not limited to, buspirone, and benzodiazepines such as diazepam, lorazepam, oxazapam, chlorazepate, clonazepam, chlordiazepoxide and alprazolam.

In another embodiment, the other therapeutic agent may be an antibacterial agent. Suitable antibacterial agents include, but are not limited to, beta-lactams, such as the penicillins, the cephalosporins, moxalactam, imipenem/cilastatin, and aztreonam; aminoglycosides, such as amikasin, gentamycin, netilmycin and tobramycin; macrolides, such as erythromycin, azithromycin and clarithromycin; fluoroquinolines; metronidazole; sulfonamides; tetracyclines; trimethroprim; and vancomycin.

In still another embodiment, the other therapeutic agent may be an antiviral agent. Suitable antiviral agents include, but are not limited to, acyclovir, amantadine, didanosine, famicyclovir, foscarnet, ganciclovir, rimatandine, stavudine, zalcitavine and zitovudine.

In yet another embodiment, the other therapeutic agent may be an anti-fungal agent. Suitable anti-fungal agents include, but are not limited to, polyene anti-fungals, such as nystatin, amphotericin, candicidin; azole derivatives, such as itraconazole, clotrimazole, miconazole, ketoconazole and fluconazole; echinocandins; 5-fluorocytosine; griseofulvin; amphotericin B; flucytosine; triazoles, and terbinafine.

In a further embodiment, the other therapeutic agent may be an anti-parasitic agent. Suitable anti-parasitic agents include, but are not limited to, ivermectin, mebendazole, mefloquine, pentamidine, praziquantel, pyrimethamine and quinine.

In another embodiment, the other therapeutic agent may be an anti-pruritic agent. Suitable anti-pruritic agents include, but are not limited to, allantoin, lignocaine, meleleuca oil, pine tar and crotamiton.

A Purine Derivative and the other therapeutic agent can act additively or, in one embodiment, synergistically. In one embodiment, a Purine Derivative is adminsitered concurrently with another therapeutic agent. In one embodiment, a composition comprising an effective amount of a Purine Derivative and an effective amount of another therapeutic agent can be administered. Alternatively, a composition comprising an effective amount of a Purine Derivative and a different composition comprising an effective amount of another therapeutic agent can be concurrently administered.

In another embodiment, an effective amount of a Purine Derivative is administered prior or subsequent to administration of an effective amount of another therapeutic agent. In this embodiment, the Purine Derivative is administered while the other therapeutic agent exerts its therapeutic effect, or the other therapeutic agent is administered while the Purine Derivative exerts its preventative or therapeutic effect for treating or preventing a Condition.

A composition of the invention can be prepared using a method comprising admixing a Purine Derivative or a pharmaceutically acceptable salt and a physiologically acceptable carrier or excipient. Admixing can be accomplished using methods well known for admixing a compound (or salt) and a physiologically acceptable carrier or exipient.

5.6 Therapeutic or Prophylactic Uses of the Purine Derivatives

5.6.1 Treatment or Prevention of a Cardiovascular Disease

A cardiovascular disease can be treated or prevented by administration of an effective amount of a Purine Derivative.

Cardiovascular diseases that can be treated or prevented by administering an effective amount of a Purine Derivative include, but are not limited to, atherosclerosis, hypertension, congestive heart failure, circulatory shock, cardiomyopathy, cardiac transplant, cardiac ischemia, cardioplegia, myocardial infarction, and a cardiac arrhythmia, such as atrial fibrillation, supraventricular tachycardia, atrial flutter, and paroxysmal atrial tachycardia.

In one embodiment, the cardiovascular disease is a cardiac ischemia, hypertension or atherosclerosis.

5.6.2 Treatment or Prevention of an Inflammatory Disease

An inflammatory disease can be treated or prevented by administration of an effective amount of a Purine Derivative.

Inflammatory diseases that can be treated or prevented by administering an effective amount of a Purine Derivative include, but are not limited to, organ transplant rejection; reoxygenation injury resulting from organ transplantation including, but not limited to, transplantation of the following organs: heart, lung, liver and kidney; systemic inflammatory response syndrome; chronic inflammatory diseases of the joints, including arthritis, rheumatoid arthritis, osteoarthritis and bone diseases associated with increased bone resorption; inflammatory bowel diseases such as ileitis, ulcerative colitis, Barrett's syndrome, and Crohn's disease; inflammatory lung diseases such as asthma, adult respiratory distress syndrome, and chronic obstructive airway disease; inflammatory diseases of the eye including corneal dystrophy, trachoma, onchocerciasis, uveitis, sympathetic ophthalmitis and endophthalmitis; chronic inflammatory diseases of the gum, including gingivitis and periodontitis; inflammatory diseases of the joints including arthritis and osteoarthritis; inflammatory diseases of the kidney including uremic complications, glomerulonephritis and nephrosis; inflammatory diseases of the skin including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoinimune encephalitis; autoimmune diseases including Type I and Type II diabetes mellitus; diabetic complications, including, but not limited to, diabetic cataract, glaucoma, retinopathy, nephropathy, such as.microaluminuria and progressive diabetic nephropathy, polyneuropathy, gangrene of the feet, atherosclerotic coronary arterial disease, peripheral arterial disease, nonketotic hyperglycemic-hyperosmolar coma, mononeuropathies, autonomic neuropathy, foot ulcers, joint problems, and a skin or mucous membrane complication, such as an infection, a shin spot, a candidal infection or necrobiosis lipoidica diabeticorum; immune-complex vasculitis, systemic lupus erythematosus (SLE); inflammatory diseases of the heart such as cardiomyopathy, ischemic heart disease hypercholesterolemia, and atherosclerosis; as well as various other diseases that can have significant inflammatory components, including preeclampsia; chronic liver failure, brain and spinal cord trauma, and cancer. The inflammatory disease can also be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is adminstered as a treatment for cancer.

In one embodiment, the inflammatory disease is an inflammatory lung disease, an autoimmune inflammatory disease, an inflammatory disease of the eye, an inflammatory disease of the gum, an inflammatory disease of the central nervous system, an inflammatory disease of the skin, an inflammatory disease of the bowel or an inflammatory disease of a joint.

In one embodiment, the inflammatory disease of the skin is psoriasis.

In another embodiment, the inflammatory lung disease is asthma.

5.6.3 Treatment or Prevention of a Neurological Disorder

A neurological disorder can be treated or prevented by administration of an effective amount of a Purine Derivative.

Neurological disorders that can be treated or prevented by administering an effective amount of a Purine Derivative include, but are not limited to, a seizure disorder, such as epilepsy; pain, including acute postoperative pain, cancer pain, neuropathic pain, and a psychogenic pain syndrome; delirium and dementia, such as Lewy body dementia, Alzheimer's disease, Pick's disease, or a Creutzfeldt-Jakob disease; a sleep disorder, such as insomnia, hypersomnia, a sleep apnea syndrome, restless-leg syndrome, or a parasomnia; a cranial nerve disorder, such as Bell's palsy; a disorder of movement, such as tremor, dystonia, Tourette's Syndrome, myoclonus, Huntington's disease, cortico basal degeneration, chorea, a drug-induced movement disorder, progressive supranuclear palsy, Parkinson's disease, or a Parkinsonian Syndrome, such as multiple system atrophy, Wilson's disease or mult-infarct state; a demyelinating disease, such as multiple sclerosis or amyotrophic lateral sclerosis; a neuro-muscular disease, such as muscular dystrophy; a cerebrovascular disease, such as stroke; a neuroopthalmic disorder; and a psychiatric disorder, such as schizophrenia.

In one embodiment, the neurological disorder treated or prevented is epilepsy, pain, or stroke.

5.6.4 Treatment or Prevention of an Ischemic Condition

An ischemic condition can be treated or prevented by administration of an effective amount of a Purine Derivative.

Ischemic conditions that can be treated or prevented by administering an effective amount of a Purine Derivative include, but are not limited to, stable angina, unstable angina, myocardial ischemia, hepatic ischemia, mesenteric artery ischemia, intestinal ischemia, critical limb ischemia, chronic critical limb ischemia, erebral ischemia, acute cardiac ischemia, and an ischemic disease of the central nervous system, such as stroke or cerebral ischemia.

In one embodiment, the ischemic condition is myocardial ischemia, stable angina, unstable angina, stroke, ischemic heart disease or cerebral ischemia.

5.6.5 Treatment or Prevention of a Reperfusion Injury

A reperfusion injury can be treated or prevented by administration of an effective amount of a Purine Derivative. Reperfusion injury can result following a naturally occurring episode, such as a myocardial infarction, stroke, or during a surgical procedure where blood flow in vessels is intentionally or unintentionally blocked.

Reperfusion injuries that can be treated or prevented by administering an effective amount of a Purine Derivative include, but are not limited to, intestinal reperfusion injury, myocardial reperfusion injury; and reperfusion injury resulting from cardiopulmonary bypass surgery, thoracoabrominal aneurysm repair surgery, carotid endaretectomy surgery, or hemorrhagic shock.

In one embodiment, the reperfusion injury results from cardiopulmonary bypass surgery, thoracoabrominal aneurysm repair surgery, carotid endarerectomy surgery or hemorrhagic shock.

5.6.6 Treatment or Prevention of a Skin Disorder

A skin disorder can be treated or prevented by administration of an effective amount of a Purine Derivative.

Skin disorders that can be treated or prevented by administering an effective amount of a Purine Derivative include, but are not limited to, pruritis; acne; skin rashes, such as psoriasis, dermatitis, rosacea, lichen planus, keratosis, drug rashes and granuloma annulare; sunburn and skin photosensitivity reactions; warts, such as plantar warts, common warts, filiform warts, flat worts, genital warts, and keratoses; and skin pigment disorders such as albinism, melasma and vitiligo.

In one embodiment, the skin disorder is psoriasis.

5.6.7 Treatment or Prevention of a Cellular Proliferative Disorder

A cellular proliferative disorder can be treated or prevented by administration of an effective amount of a Purine Derivative.

Types of cellular proliferative disorders that can be treated or prevented by administering an effective amount of a Purine Derivative include, but are not limited to, cancer, uterine fibroids, benign prostatic hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, fungal infections, and defective apoptosis-associated conditions.

In one embodiment, the cellular proliferative disorder is cancer.

5.6.7.1 Treatment or Prevention of Cancer

In one embodiment, the Purine Derivatives can also be administered to prevent progression to a neoplastic or malignant state, including but not limited to the cancers listed in Table 1. Such prophylactic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, Basic Pathology, 2d Ed., W.B. Saunders Co., Philadelphia, pp. 68-79). Hyperplasia is a form of controlled cell proliferation involving an increase in cell number in a tissue or organ, without significant alteration in structure or function. For example, endometrial hyperplasia often precedes endometrial cancer and pre-cancerous colon polyps often transform into cancerous lesions. Metaplasia is a form of controlled cell growth in which one type of adult or fully differentiated cell substitutes for another type of adult cell. Metaplasia can occur in epithelial or connective tissue cells. A typical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a subject, can indicate the desirability of prophylactic/therapeutic administration of the composition of the invention. Such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. (see also id., at pp. 84-90 for characteristics associated with a transformed or malignant phenotype).

In a specific embodiment, leukoplakia, a benign-appearing hyperplastic or dysplastic lesion of the epithelium, or Bowen's disease, a carcinoma in situ, are pre-neoplastic lesions indicative of the desirability of prophylactic intervention.

In another embodiment, fibrocystic disease (cystic hyperplasia, mammary dysplasia, particularly adenosis (benign epithelial hyperplasia)) is indicative of the desirability of prophylactic intervention.

The prophylactic use of the compounds and methods of the present invention are also indicated in some viral infections that may lead to cancer. For example, human papilloma virus can lead to cervical cancer (see, e.g., Hernandez-Avila et al., Archives of Medical Research (1997) 28:265-271), Epstein-Barr virus (EBV) can lead to lymphoma (see, e.g., Herrmann et al., J Pathol (2003) 199(2): 140-5), hepatitis B or C virus can lead to liver carcinoma (see, e.g., El-Serag, J Clin Gastroenterol (2002) 35(5 Suppl 2):S72-8), human T cell leukemia virus (HTLV)-I can lead to T-cell leukemia (see e.g., Mortreux et al., Leukemia (2003) 17(1):26-38), human herpesvirus-8 infection can lead to Kaposi's sarcoma (see, e.g., Kadow et al., Curr Opin Investig Drugs (2002) 3(11): 1574-9), and Human Immune deficiency Virus (HIV) infection contribute to cancer development as a consequence of immunodeficiency (see, e.g., Dal Maso et al., Lancet Oncol (2003) 4(2): 110-9).

In other embodiments, a subject which exhibits one or more of the following predisposing factors for malignancy can treated by administration of the compounds or methods of the invention: a chromosomal translocation associated with a malignancy (e.g., the Philadelphia chromosome for chronic myelogenous leukemia, t(14;18) for follicular lymphoma, etc.), familial polyposis or Gardner's syndrome (possible forerunners of colon cancer), benign monoclonal gammopathy (a possible forerunner of multiple myeloma), a first degree kinship with persons having a cancer or precancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, 1976, Basic Pathology, 2d Ed., W.B. Saunders Co., Philadelphia, pp. 112-113) etc.), and exposure to carcinogens (e.g., smoking, and inhalation of or contacting with certain chemicals).

In a preferred embodiment, the present invention provides methods for treating cancer, including but not limited to: killing a cancer cell or neoplastic cell; inhibiting the growth of a cancer cell or neoplastic cell; inhibiting the replication of a cancer cell or neoplastic cell; or ameliorating a symptom thereof, the methods comprising administering to a subject in need thereof an amount of the Purine Derivatives effective to treat cancer.

In one embodiment, the invention provides a method for treating cancer, said method comprising administering to a subject in need thereof an amount of a Purine Derivative or a pharmaceutically acceptable salt thereof, said amount sufficient to treat cancer.

In another embodiment, the invention provides a method for treating cancer, said method comprising administering to a subject in need thereof a pharmaceutical composition comprising an amount of a Purine Derivative effective to treat cancer.

In a specific embodiment, the subject in need of treatment has previously undergone treatment for cancer. Such previous treatments include, but are not limited to, prior chemotherapy, radiotherapy, surgery, or immunotherapy, such as cancer vaccines.

Cancers that can be treated with the Compounds and methods of the Invention include, but are not limited to, cancers disclosed below in Table 1 and metastases thereof.

TABLE 1

Solid tumors, including but not limited to:

fibrosarcoma
myxosarcoma
liposarcoma
chondrosarcoma
osteogenic sarcoma
chordoma
angiosarcoma
endotheliosarcoma
lymphangiosarcoma TABLE 1-continued lymphangioendotheliosarcoma
synovioma
mesothelioma
Ewing's tumor
leiomyosarcoma
rhabdomyosarcoma
colon cancer
colorectal cancer
kidney cancer
pancreatic cancer
bone cancer
breast cancer
ovarian cancer
prostate cancer
esophageal cancer
stomach cancer
oral cancer
nasal cancer
throat cancer
squamous cell carcinoma
basal cell carcinoma
adenocarcinoma
sweat gland carcinoma
sebaceous gland carcinoma
papillary carcinoma
papillary adenocarcinomas
cystadenocarcinoma
medullary carcinoma
bronchogenic carcinoma
renal cell carcinoma
hepatoma
bile duct carcinoma
choriocarcinoma
seminoma
embryonal carcinoma
Wilms' tumor
cervical cancer
uterine cancer
testicular cancer
small cell lung carcinoma
bladder carcinoma
lung cancer
epithelial carcinoma
glioma
glioblastoma multiforme
astrocytoma
medulloblastoma
craniopharyngioma
ependymoma
pinealoma
hemangioblastoma
acoustic neuroma
oligodendroglioma
meningioma
skin cancer
melanoma
neuroblastoma
retinoblastoma
blood-borne cancers, including but not limited to:

acute lymphoblastic leukemia ("ALL")
acute lymphoblastic B-cell leukemia
acute lymphoblastic T-cell leukemia
acute myeloblastic leukemia ("AML")
acute promyelocytic leukemia ("APL")
acute monoblastic leukemia
acute erythroleukemic leukemia
acute megakaryoblastic leukemia
acute myelomonocytic leukemia
acute nonlymphocyctic leukemia
acute undifferentiated leukemia
chronic myelocytic leukemia ("CML")
chronic lymphocytic leukemia ("CLL")
hairy cell leukemia
multiple myeloma
acute and chronic leukemias:

lymphoblastic
myelogenous

TABLE 1-continued lymphocytic
myelocytic leukemias
Lymphomas:

Hodgkin's disease
non-Hodgkin's Lymphoma
Multiple myeloma
Waldenstrom's macroglobulinemia
Heavy chain disease
Polycythemia vera In one embodiment, the cancer is lung cancer, breast cancer, colorectal cancer, prostate cancer, brain cancer, esophageal cancer, pancreatic cancer, stomach cancer, liver cancer, kidney cancer, adrenal cancer, testicular cancer, ovarian cancer, cervical cancer, leukemia, Hodgkin's disease, non-Hodgkin's lympoma, skin cancer, bone cancer, a cancer of the central nervous system, or a cancer of the blood or lymphatic system.

5.6.7.2 Multi-Modality Therapy for Cancer

The Purine Derivatives can be administered to a subject that has undergone or is currently undergoing one or more additional anticancer treatment modalities including, but not limited to, chemotherapy, radiotherapy, surgery or immunotherapy, such as cancer vaccines.

In one embodiment, the invention provides methods for treating cancer comprising (a) administering to a subject in need thereof a therapeutically effective amount of a Purine Derivative; and (b) administering to said subject one or more additional anticancer treatment modalities including, but not limited to, radiotherapy, chemotherapy, surgery or immunotherapy, such as a cancer vaccine. In one embodiment, the administering of step (a) occurs prior to the administering of step (b). In another embodiment, the administering of step (a) occurs subsequent to the administering of step (b). In still another embodiment, the administering of step (a) occurs concurrently with the administering of step (b).

In one embodiment, the additional anticancer treatment modality is chemotherapy.

In another embodiment, the additional anticancer treatment modality is surgery.

In yet another embodiment, the additional anticancer treatment modality is radiation therapy.

In still another embodiment, the additional anticancer treatment modality is immunotherapy, such as cancer vaccines.

The Purine Derivative and the additional treatment modalities of the combination therapies of the invention can act additively or synergistically. A synergistic combination allows the use of lower dosages of the Purine Derivative and/or the additional treatment modality and/or less frequent administration of the Purine Derivative and/or additional treatment modality to a subject with cancer. The ability to utilize lower dosages of a Purine Derivative and/or an additional treatment modality and/or to administer a Purine Derivative and said additional treament modality less frequently can reduce the toxicity associated with the administration of a Purine Derivative and/or the additional treatment modality to a subject without reducing the efficacy of a Purine Derivative and/or the additional treatement modality in the treatment of cancer. In addition, a synergistic effect can result in the improved efficacy of the treatment of cancer and/or the reduction of adverse or unwanted side effects associated with the administration of a Purine Derivative and/or an additional anticancer treatment modality as monotherapy.

When the Purine Derivative and additional anticancer treatment modality are administered to a subject concurrently, the term "concurrently" is not limited to the administration of a Purine Derivative and an additional anticancer treatment modality at exactly the same time, but rather it is meant that they are administered to a subject in a sequence and within a time interval such that they can act synergistically to provide an increased benefit than if they were administered otherwise. For example, the Purine Derivatives may be administered at the same time or sequentially in any order at different points in time as an additional anticancer treament modality; however, if not administered at the same time, they should be administered sufficiently close in time so as to provide the desired therapeutic effect, preferably in a synergistic fashion. The Purine Derivative and the additional anticancer treatment modality can be administered separately, in any appropriate form and by any suitable route. When the Purine Derivative and the additional anticancer treatment modality are not administered concurrently, it is understood that they can be administered in any order to a subject in need thereof. For example, a Purine Derivative can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of an additional anticancer treatment modality (e.g., radiotherapy), to a subject in need thereof. In various embodiments the Purine Derivative and the additional anticancer treatment modality are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies of the invention are administered within the same office or hospital visit. In another embodiment, the Purine Derivative and the additional anticancer treatment modality are administered at 1 minute to 24 hours apart.

In one embodiment, a Purine Derivative is administered prior or subsequent to an additional anticancer treatment modality, preferably at least an hour, five hours, 12 hours, a day, a week, a month, more preferably several months (e.g., up to three months), prior or subsequent to administration of an additional anticancer treatment modality.

When the combination theapy of the invention comprises administering a Purine Derivative are with one or more additional anticancer agents, the Purine Derivative and the additional anticancer agents can be administered concurrently or sequentially to a subject. The agents can also be cyclically administered. Cycling therapy involves the administration of one or more anticancer agents for a period of time, followed by the administration of one or more different anticancer agents for a period of time and repeating this sequential administration, i.e., the cycle, in order to reduce the development of resistance to one or more of the anticancer agents of being administered, to avoid or reduce the side effects of one or more of the anticancer agents being administered, and/or to improve the efficacy of the treatment.

An additional anticancer agent may be administered over a series of sessions; any one or a combination of the additional anticancer agents listed below may be administered.

The present invention includes methods for treating cancer, comprising administering to a subject in need thereof a Purine Derivative, and one or more additional anticancer agents or pharmaceutically acceptable salts thereof. The Purine Derivative and the additional anticancer agent(s) can act additively or synergistically.

In one embodiment, the additional anti-cancer agent can be, but is not limited to, a drug listed in Table 2.

TABLE 2

| Alkylating agents | |
|---|---|
| Nitrogen mustards: | Cyclophosphamide |
| | Ifosfamide |
| | Trofosfamide |
| | Chlorambucil |
| Nitrosoureas: | Carmustine (BCNU) |
| | Lomustine (CCNU) |
| Alkylsulphonates: | Busulfan |
| | Treosulfan |
| Triazenes: | Dacarbazine |
| Platinum complexes: | Cisplatin |
| | Carboplatin |
| | Oxaliplatin |
| Plant Alkaloids | |
| Vinca alkaloids: | Vincristine |
| | Vinblastine |
| | Vindesine |
| | Vinorelbine |
| Taxoids: | Paclitaxel |
| | Docetaxel |
| DNA Topoisomerase Inhibitors | |
| Epipodophyllins: | Etoposide |
| | Teniposide |
| | Topotecan |
| | 9-aminocamptothecin |
| | Camptothecin |
| | Crisnatol |
| Mitomycins: | Mitomycin C |
| Anti-metabolites | |
| Anti-folates: | |
| DHFR inhibitors: | Methotrexate |
| | Trimetrexate |
| IMP dehydrogenase Inhibitors: | Mycophenolic acid |
| | Tiazofurin |
| | Ribavirin |
| | EICAR |
| Ribonuclotide reductase Inhibitors: | Hydroxyurea |
| | Deferoxamine |
| Pyrimidine analogs: | |
| Uracil analogs: | 5-Fluorouracil |
| | Floxuridine |
| | Doxifluridine |
| | Ratitrexed |
| Cytosine analogs: | Cytarabine (ara C) |
| | Cytosine arabinoside |
| | Fludarabine |
| | Gemcitabine |
| | Capecitabine |
| Purine analogs: | Mercaptopurine |
| | Thioguanine |
| DNA Antimetabolites: | 3-HP |
| | 2'-deoxy-5-fluorouridine |
| | 5-HP |
| | alpha-TGDR |
| | aphidicolin glycinate |
| | ara-C |
| | 5-aza-2'-deoxycytidine |
| | beta-TGDR |
| | cyclocytidine |
| | guanazole |

TABLE 2-continued

| | inosine glycodialdehyde |
|---|---|
| | macebecin II |
| | Pyrazoloimidazole |
| Hormonal therapies: | |
| Receptor antagonists: | |
| Anti-estrogen: | Tamoxifen |
| | Raloxifene |
| | Megestrol |
| LHRH agonists: | Goserelin |
| | Leuprolide acetate |
| Anti-androgens: | Flutamide |
| | Bicalutamide |
| Retinoids/Deltoids | Cis-retinoic acid |
| Vitamin A derivative: | All-trans retinoic acid (ATRA-IV) |
| Vitamin D3 analogs: | EB 1089 |
| | CB 1093 |
| | KH 1060 |
| Photodynamic therapies: | Vertoporfin (BPD-MA) |
| | Phthalocyanine |
| | Photosensitizer Pc4 |
| | Demethoxy-hypocrellin A |
| | (2BA-2-DMHA) |
| Cytokines: | Interferon-α |
| | Interferon-β |
| | Interferon-γ |
| | Tumor necrosis factor |
| Angiogenesis Inhibitors: | Angiostatin (plasminogen fragment) |
| | antiangiogenic antithrombin III |
| | Angiozyme |
| | ABT-627 |
| | Bay 12-9566 |
| | Benefin |
| | Bevacizumab |
| | BMS-275291 |
| | cartilage-derived inhibitor (CDI) |
| | CAI |
| | CD59 complement fragment |
| | CEP-7055 |
| | Col 3 |
| | Combretastatin A-4 |
| | Endostatin (collagen XVIII fragment) |
| | Fibronectin fragment |
| | Gro-beta |
| | Halofuginone |
| | Heparinases |
| | Heparin hexasaccharide fragment |
| | HMV833 |
| | Human chorionic gonadotropin (hCG) |
| | IM-862 |
| | Interferon alpha/beta/gamma |
| | Interferon inducible protein (IP-10) |
| | Interleukin-12 |
| | Kringle 5 (plasminogen fragment) |
| | Marimastat |
| | Metalloproteinase inhibitors (TIMPs) |
| | 2-Methoxyestradiol |
| | MMI 270 (CGS 27023A) |
| | MoAb IMC-1C11 |
| | Neovastat |
| | NM-3 |
| | Panzem |
| | PI-88 |
| | Placental ribonuclease inhibitor |
| | Plasminogen activator inhibitor |
| | Platelet factor-4 (PF4) |
| | Prinomastat |
| | Prolactin 16 kD fragment |
| | Proliferin-related protein (PRP) |
| | PTK 787/ZK 222594 |
| | Retinoids |
| | Solimastat |
| | Squalamine |
| | SS 3304 |
| | SU 5416 |
| | SU6668 |
| | SU11248 |
| | Tetrahydrocortisol-S |

TABLE 2-continued

| | |
|---|---|
| | Tetrathiomolybdate |
| | Thalidomide |
| | Thrombospondin-1 (TSP-1) |
| | TNP-470 |
| | Transforming growth factor-beta (TGF-β) |
| | Vasculostatin |
| | Vasostatin (calreticulin fragment) |
| | ZD6126 |
| | ZD 6474 |
| | farnesyl transferase inhibitors (FTI) |
| | Bisphosphonates |
| Antimitotic agents: | Allocolchicine |
| | Halichondrin B |
| | Colchicine |
| | colchicine derivative |
| | dolstatin 10 |
| | Maytansine |
| | Rhizoxin |
| | Thiocolchicine |
| | trityl cysteine |
| Others: | |
| Isoprenylation inhibitors: | |
| Dopaminergic neurotoxins: | 1-methyl-4-phenylpyridinium ion |
| Cell cycle inhibitors: | Staurosporine |
| Actinomycins: | Actinomycin D |
| | Dactinomycin |
| Bleomycins: | Bleomycin A2 |
| | Bleomycin B2 |
| | Peplomycin |
| Anthracyclines: | Daunorubicin |
| | Doxorubicin (adriamycin) |
| | Idarubicin |
| | Epirubicin |
| | Pirarubicin |
| | Zorubicin |
| | Mitoxantrone |
| MDR inhibitors: | Verapamil |
| $Ca^{2+}$ATPase inhibitors: | Thapsigargin |

In a further aspect of the invention the Purine Derivatives can be administered in conjunction with chemical agents that are understood to mimic the effects of radiotherapy and/or that function by direct contact with DNA. Preferred agents for use in combination with the Purine Derivatives for treating cancer include, but are not limited to cis-diamminedichloro platinum (II) (cisplatin), doxorubicin, 5-fluorouracil, taxol, and topoisomerase inhibitors such as etoposide, teniposide, irinotecan and topotecan.

Additionally, the invention provides methods of treatment of cancer using the Purine Derivatives as an alternative to chemotherapy alone or radiotherapy alone where the chemotherapy or the radiotherapy has proven or can prove too toxic, e.g., results in unacceptable or unbearable side effects, for the subject being treated. The subject being treated can, optionally, be treated with another anticancer treatment modality such as chemotherapy, surgery, or immunotherapy, depending on which treatment is found to be acceptable or bearable.

The Purine Derivatives can also be used in vitro or ex vivo, such as for the treatment of certain cancers, including, but not limited to leukemias and lymphomas, such treatment involving autologous stem cell transplants. This can involve a multi-step process in which the subject's autologous hematopoietic stem cells are harvested and purged of all cancer cells, the subject is then administered an amount of a Purine Derivative effective to eradicate the subject's remaining bone-marrow cell population, then the stem cell graft is infused back into the subject. Supportive care can then be provided while bone marrow function is restored and the subject recovers.

5.6.8 Treatment of Wounds

Also encompassed are method for treating a wound, comprising administering to a subject in need thereof an effective amount of a Purine Derivative.

Wounds that can be treated by administering an effective amount of a Purine Derivative include, but are not limited to, an avulsion, an incision, a bruise, a laceration, an amputation, a puncture wound, an abrasion, an ischemic ulcer, a decubitus ulcer, an ulcer due to an infectious processe, an ulcer due to an inflammatory processe, and a wound caused by a burn.

The wounds may be caused accidentally or may be inflicted intentionally, such as those which are inflicted during surgery or other medical procedures.

In one embodiment, the methods for treating a wound expedite would healing.

In another embodiment, the methods for treating a wound can further comprise administering an effective amount of another therapeutic agent. Other therapeutic agents useful in the methods for treating a wound include, but are not limited to, an antibacterial agent, an antiviral agent, an antifungal agent, an antiparasitic agent, an antiinflammatory agent, an analgesic agent, an antipruritic agent, or any combination thereof, for example, as disclosed herein.

In another embodiment, the present invention provides a method for stimulating the influx of fibroblasts, vascular endothelial cells or epithelial cells into a wound, comprising administering to a subject in need thereof an effective amount of a Purine Derivative.

5.6.9 Treatment or Prevention of a Radiation-Induced Injury

A radiation-induced injury can be treated or prevented by administration of an effective amount of a Purine Derivative to a subject.

Examples of a radiation-induced injury treatable or preventable using the present methods include, but are not limited to, an acute radiation syndrome, such as a cerebral syndrome; a gastrointestinal syndrome; a hematopoietic syndrome; acute radiation sickness; pulmonary fibrosis; radiation proctitis; neuropathy; nausea; vomiting; alopecia; pain; headache; esophageal stricture; gastric ulcer; radiation pneumonitis; cardiomyopathy; photodamaged skin, which is characterized by locally exaggerated pigmentation, looseness, fine lines, wrinkles, enlarged pores, and the development of darkened plugs in the sebacious glands; skin cancer; sunburn; solar dermatitis; photoallergic dermatitis; sun spots; age spots; and sun poisoning.

In one embodiment, treating a radiation-induced injury includes increasing a subject's survival time following exposure to radiation.

In another embodiment, death is an example of a radiation-induced injury that is preventable according to the present invention.

The Purine Derivatives are also useful for protecting bystander healthy tissue from a radiation-induced injury during administration of therapeutic radiation.

A radiation-induced injury may result from exposure of a subject to ionizing radiation from numerous sources including, but not limited to, a nuclear weapon, such as an atomic bomb, a neutron bomb, or a "dirty bomb;" an industrial source, such as a nuclear power plant, a nuclear submarine, or a nuclear waste disposal site; sunlight; or a diagnostic or therapeutic medical or dental application, such as x-rays, CT scans, external radiation therapy, internal radiation therapy (e.g., radioactive "seed" implants used in cancer therapy). The injury might result from an accident, an act of war or terrorism, cumulative exposure at the home or workplace, purposeful exposure during medical diagnosis or treatment, or exposure to ultraviolet radiation, such as from sunlight.

Examples of a radiation-induced injury caused by exposure to sunlight include, but are not limited to photodamaged skin, which is characterized by locally exaggerated pigmentation, looseness, fine lines, wrinkles, enlarged pores, and the development of darkened plugs in the sebacious glands; skin cancer; sunburn; solar dermatitis; photoallergic dermatitis; sun spots; age spots; and sun poisoning. In one embodiment, a subject being treated for a radiation-induced injury caused by exposure to sunlight has been sensitized to sunlight by a disease or by medication (drug-induced sensitivity).

In one embodiment, the injury is induced by radiation from a nuclear weapon.

In another embodiment, the injury is induced by radiation from a nuclear power plant.

In still another embodiment, the injury is induced by radiation from radiation therapy that the subject is receiving for the treatment of a non-radiation related disorder.

In still another embodiment, the injury is induced by radiation from radiation therapy that the subject is receiving for the treatment of cancer.

In one embodiment, the injury is induced by radiation from a radioactive material that is ingested by a subject.

In another embodiment, the injury is caused by exposure to sunlight.

In one embodiment, the radiation-induced injury is in a cell or tissue that is exposed to a reactive species.

5.7 Kits

The invention encompasses kits that can simplify the administration of the Purine Derivatives or composition of the invention to a subject.

A typical kit of the invention comprises a unit dosage of a Purine Derivative. In one embodiment, the unit dosage form is in a container, which can be sterile, containing an effective amount of a Purine Derivative and a pharmaceutically acceptable vehicle. In another embodiment, the unit dosage form is in a container containing an effective amount of a Purine Derivative as a lyophilate or pharmaceutically acceptable salt. In this instance, the kit can further comprise another container that contains a solution useful for the reconstitution of the lyophilate or dissolution of the salt. The kit can also comprise a label or printed instructions for use of the Purine Derivatives.

In a further embodiment, the kit comprises a unit dosage form of a composition of the invention.

Kits of the invention can further comprise one or more devices that are useful for administering the unit dosage forms of the Purine Derivatives or a composition of the invention. Examples of such devices include, but are not limited to, a syringe, a drip bag, a patch or an enema, which optionally contain the unit dosage forms.

The present invention is not to be limited in scope by the specific embodiments disclosed in the examples which are intended as illustrations of a few aspects of the invention and any embodiments that are functionally equivalent are within the scope of this invention.

6. EXAMPLES

Materials: [³H]NECA was obtained from Du Pont NEN, Dreieich, Germany. All other unlabeled adenosine receptor agonists and antagonists can be obtained from RBI, Natick, Mass. The 96-well microplate filtration system (MultiScreen MAFC) was obtained from Millipore, Eschborn, Germany. Penicillin (100 U/mL), streptomycin (100 μg/mL), L-glutamine and G-418 were obtained from Gibco-Life Technologies, Eggenstein, Germany. Guanosine and 2',3'-isopropylideneguanosine were purchased from Sigma Aldrich Chemical Co., USA. 2-Chloro-NECA was prepared using the methods set forth in Hutchison et al., *J. Med. Chem.* 33:1919-1924 (1990). 2-Iodo-NECA was prepared by following Cristalli et al., *J. Med. Chem.* 35:2363-2368 (1992), and Cristalli et al., *J. Med. Chem.* 38:1462-1472 (1995). All other materials can be obtained as described in Klotz et al., *J. Biol. Chem.*, 260:14659-14664 (1985); Lohse et al., *Naunyn-Schmiedeberg's Arch. Pharmacol.*, 336:204-210 (1987); and Klotz et al., *Naunyn-Schmiedeberg's Arch. Pharmacol.*, 357: 1-9 (1998).

General Methods: Proton nuclear magnetic resonance (NMR) spectra were obtained from Varian 300 MHz spectrophotometer and chemical shifts are reported in parts per million. Compounds were characterized on the basis of NMR and Mass spectral (MS) data.

6.1 Example 1

Synthesis of Compounds 24-31, 33, 34, 38-40, 45, 47 and 48

Step A—Synthesis of 2-N-Hydrazinoadenosine-5'-N-ethylcarboxamide: A mixture of 2-chloro-5'-N-ethylcarboxarnidoadenosine (110 mg, prepared as described in Hutchison et al., *J. Med. Chem.* 33:1919-1924 (1990)) in hydrazine monohydrate (2 mL) was allowed to stir at about 25° C. for about 24 hours. The reaction mixture was then concentrated and dried in vacuo. The resultant residue was suspended in MeOH (3 mL) and the solid that separated out was filtered, washed using methanol and dried in vacuo to provide 2-N-hydrazinoadenosine-5'-N-ethylcarboxamide (100 mg).

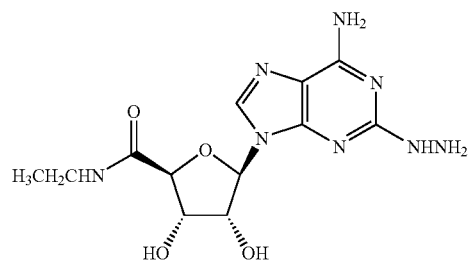

2-N-Hydrazinoadenosine-5'-N-ethylcarboxamide

Step B—General procedure for the synthesis of Compounds 24-31, 33, 34, 38-40, 45, 47 and 48: A solution of 2-N-hydrazinoadenosine-5'-N-ethylcarboxamide (prepared as described above) in methanol (about 0.5 to about 1.0 M solution) was treated with the corresponding aldehyde (2 to 5 eq.) and the resultant reaction was heated at reflux and the reaction was monitored using thin-layer chromatography until the 2-N-hydrazinoadenosine-5'-N-ethylcarboxamide was consumed. When the reaction was complete, the resultant reaction mixture was cooled to room temperature and concentrated in vacuo. The resultant residue was purified using flash column chromatography on silica gel (about 1% to about 25% methanol/dichloromethane as eluent) to provide the illustrative Purine Derivatives.

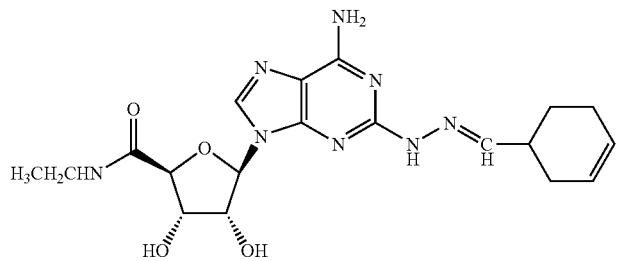

24: MS m/z 432.17 [M + H]$^+$;

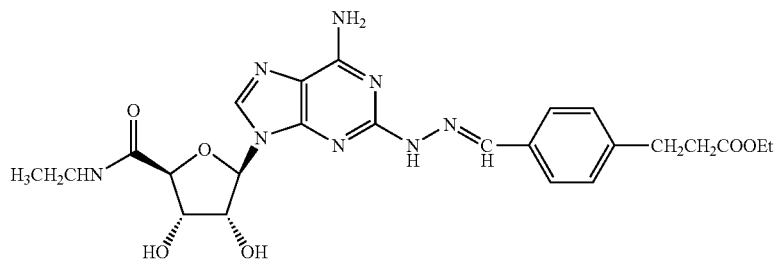

25: MS m/z 527.6 [M + H]$^+$;

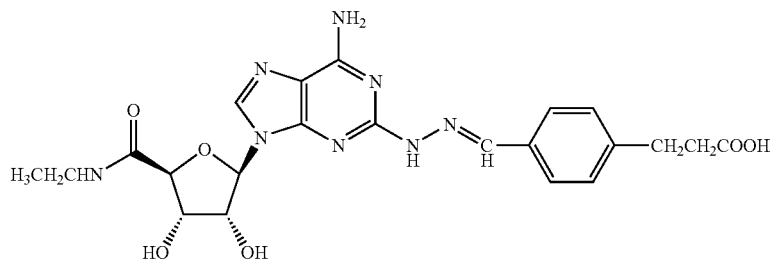

26: MS m/z 499.5 [M + H]$^+$;

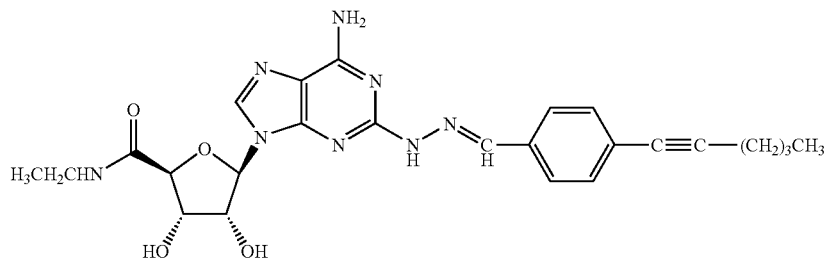

27: MS m/z 506.85 [M + H]$^+$;

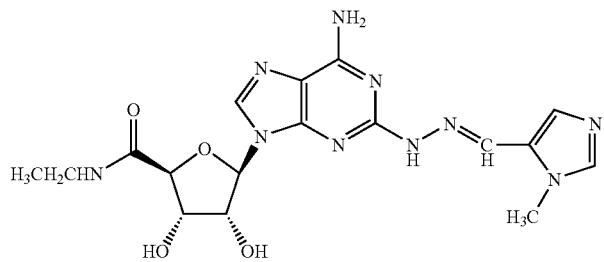

28: MS m/z 453.07 [M + Na]$^+$;

-continued
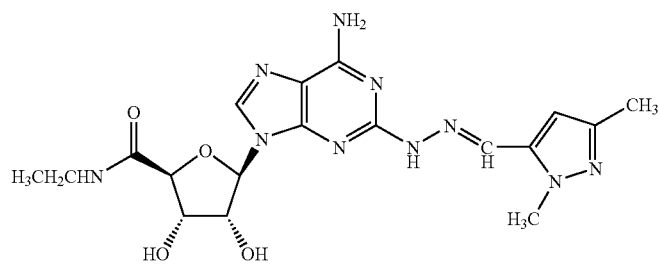
29: MS m/z 445.13 [M + H]+;
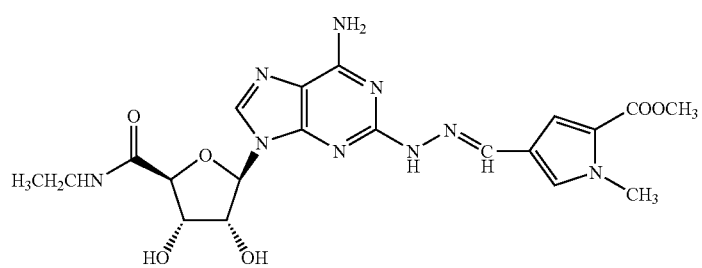
30: MS m/z 488.07 [M + H]+;
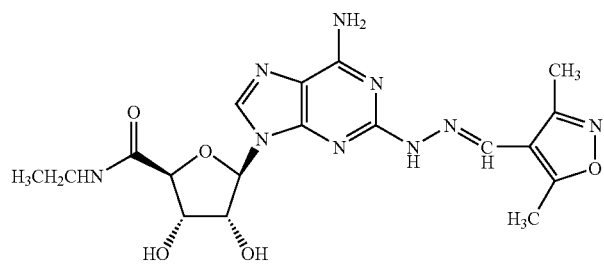
31: MS m/z 446.09 [M + H]+;
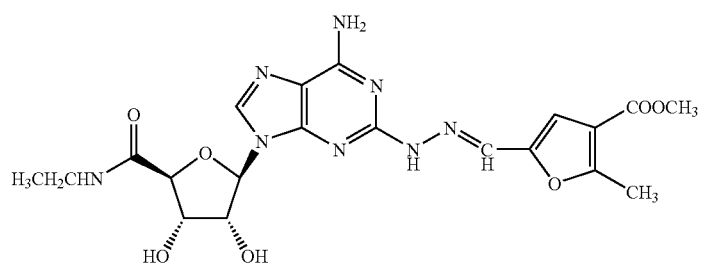
33: MS m/z 489.07 [M + H]+;
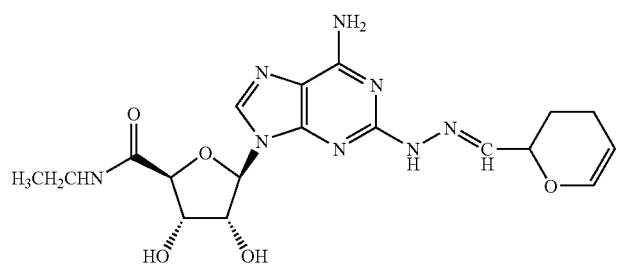
34: MS m/z 433.27 [M + H]+;

-continued
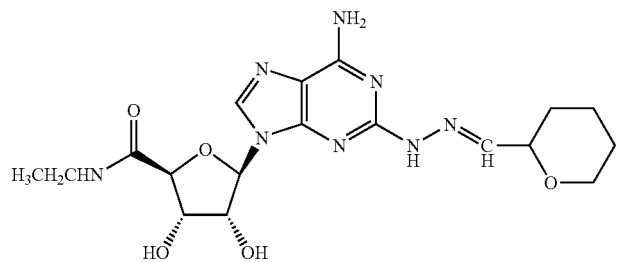
38: MS m/z 435.04 [M + H]+;
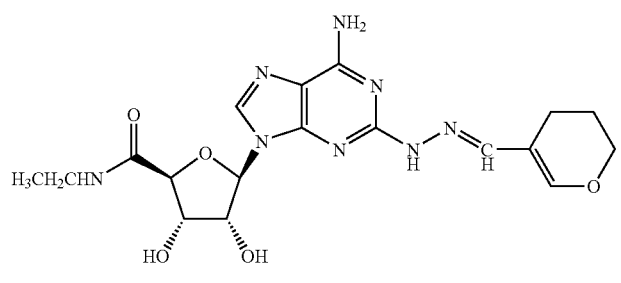
39: MS m/z 433.19 [M + H]+;
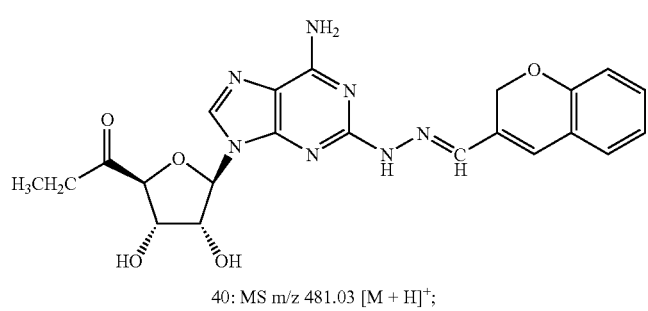
40: MS m/z 481.03 [M + H]+;
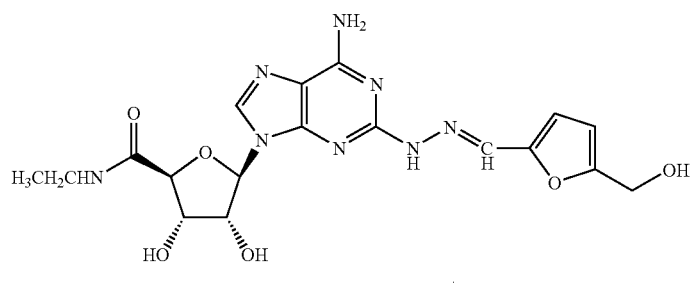
45: MS m/z 447.01 [M + H]+;
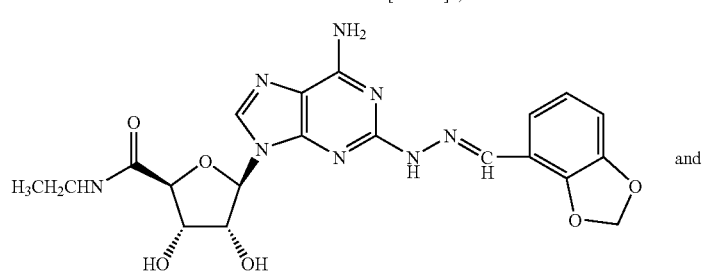
and
47: MS m/z 470.96 [M + H]+;

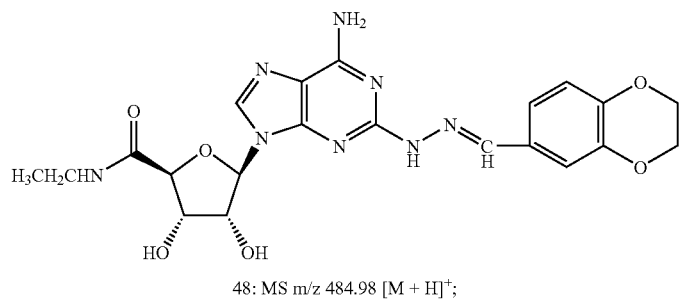

48: MS m/z 484.98 [M + H]+;

6.2 Example 2

Synthesis of Compound 42

Step A—Synthesis of 2-N-Hydrazino-$N^6$-ethyladenosine-5'-N-ethylcarboxamide: Using the method described in Example 1, step A and substituting 2-chloro-$N^6$-ethyladenosine-5'-N-ethylcarboxamide for 2-chloro-NECA in step A, 2-N-Hydrazino-$N^6$-ethyladenosine-5'-N-ethylcarboxamide was prepared.

2-N-Hydrazino-$N^6$-ethyladenosine-5'-N-ethylcarboxamide

Step B—Synthesis of Compound 42: Using the method described in Example 1, step B and substituting 2-N-Hydrazino-$N^6$-ethyladenosine-5'-N-ethylcarboxamide for 2-N-hydrazinoadenosine-5'-N-ethylcarboxamide, Compound 42 was prepared. MS m/z 421.54 [M+H]+.

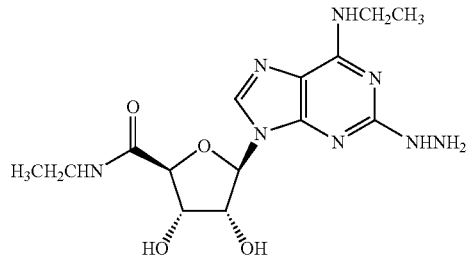

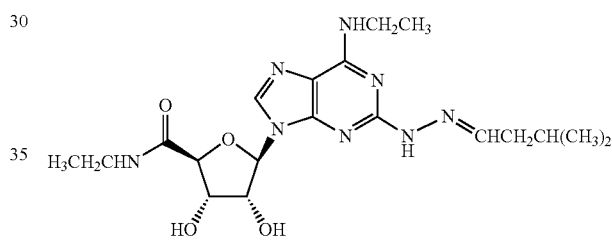

42

6.3 Example 3

Synthesis of (R)-3,4-dihyro-2H-pyran-2-carbaldehyde

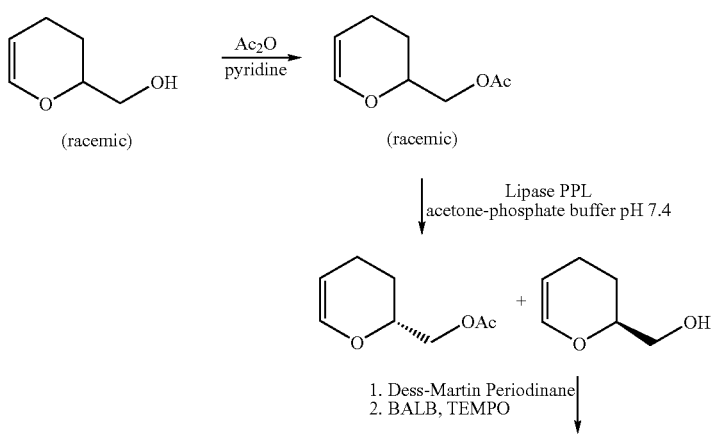

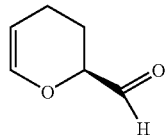

(R)-3,4-dihydro-2H-pyran-2-carbaldehyde

A mixture of (±)-3,4-dihydro-2H-pyran-2-methanol (514 g, 4.51 mol, 1 eq) and acetic anhydride (621 g, 6.09 mol, 1.35 eq) was cooled to 0° C. To the resultant mixture was added pyridine (35.6 g, 0.45 mol, 0.1 eq) and the resultant reaction mixture was allowed to warm to room temperature with stirring. The resultant reaction mixture was allowed to stir for an additional 8 hours after reaching room temperature and was shown to be complete by thin-layer chromatography (2:1 hexanes:ethyl acetate, 12 staining). The reaction mixture was concentrated in vacuo at 35° C. and the resultant residue was diluted using ethyl acetate (2 L). The resultant mixture was transferred to a separatory funnel and sequentially washed with deionized water (3×1 L), saturated aqueous NaHCO₃ (2×10 L), and brine (1.0 L). The organic layer was dried over sodium sulfate and concentrated in vacuo at 35° C. to provide (±)-3,4-dihydro-2H-pyran-2-yl-methyl acetate as a clear liquid (605.9 g, 86% yield). $^1$H NMR (300 MHz, CDCl₃) δ 1.6-2.2 (m, 4 H), 2.1 (s, 3 H), 4.2 (m, 3 H), 4.8 (m, 1 H), 6.4 (m, 1 H).

pH 7.4 buffer (47 L) was cooled to 0° C. and a solution of (±)-3,4-dihydro-2H-pyran-2-yl-methyl acetate (605.9 g, 3.88 mol, 1 eq) in acetone (215 mL) was added to the cooled buffer. To the resultant mixture was added Lipase (56.8 g, suspended in 1380 mL of Acetone—obtained from porcine pancreas, Type II). The resultant reaction mixture was allowed to stir at 0° C. and the pH of the reaction mixture was maintained at 7.40±0.20 using aqueous NaOH (2 M ). The reaction was monitored using chiral HPLC and was shown to be complete after 40 hours. The resultant reaction mixture was extracted using ethyl acetate (6×2.5 L). The organic layers were combined, and Celite (200 g) was suspended in the combined organic layers. The resultant mixture was then filtered and the filtrate was transferred to a separatory funnel. The ethyl acetate layer was collected and cooled to below 0° C. to freeze any residual water. The resultant ice crystals were filtered and the ethyl acetate was dried over sodium sulfate, filtrered and concentrated in vacuo at 35° C. to provide 368.7 g of a light yellow liquid residue. The residue was purified using column chromatography (4 inch diameter column packed with 1.8 kg of silica gel (5 g/g loading with respect to residue) which was slurried in hexanes). The column was sequentially eluted with hexanes (2 L), 90% hexanes/ethyl acetate (2 L), 75% hexanes/ethyl acetate (8 L), and 2 L of 50% hexanes/ethyl acetate (2 L) to provide (R)-3,4-dihydro-2H-pyran-2-carbaldehyde as a light yellow liquid (208 g, 69% yield). $^1$H NMR (300 MHz, CDCl₃) δ 1.6-2.2 (m, 4 H), 2.1 (s, 3 H), 4.2 (m, 3 H), 4.8 (m, 1 H), 6.4 (m, 1 H).

6.4 Example 4

Synthesis of Compound 43

Step A—Synthesis of 2-N-Hydrazinoadenosine-5'-N-ethylcarboxamide: Using the method described in Example 1, step A, 2-N-Hydrazino-5'-N-ethylcarboxamide was prepared.

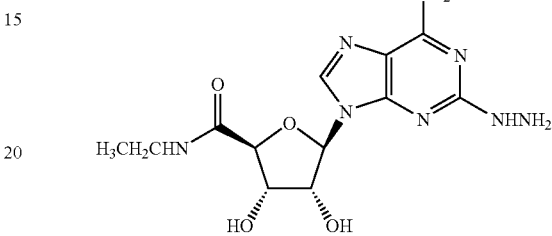

2-N-Hydrazinoadenosine-5'-N-ethylcarboxamide

Step B—Synthesis of Compound 43: Following the method described in Example 1, step 2 and using (R)-3,4-dihydro-2H-pyran-2-carbaldehyde (made as described in Example 3) as the aldehyde reactant, Compound 43 was prepared. MS m/z 433.19 [M+H]⁺;

43

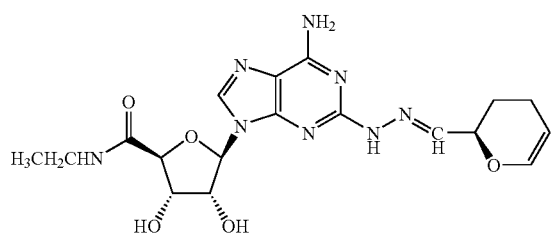

6.5 Example 5

Synthesis of Compound 44

Step A—Synthesis of 2-N-Hydrazinoadenosine-5'-N-ethylcarboxamide: Using the method described in Example 1, step A, 2-N-Hydrazino-5'-N-ethylcarboxamide was prepared.

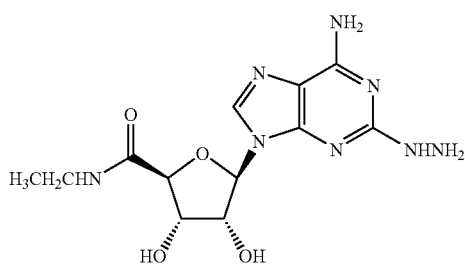

2-N-Hydrazinoadenosine-5'-N-ethylcarboxamide

Step B—Synthesis of Compound 44: Following the method described in Example 1, step B and using (S)-3,4-dihydro-2H-pyran-2-carbaldehyde as the aldehyde reactant, Compound 44 was prepared. MS m/z 433.02 [M+H]$^+$.

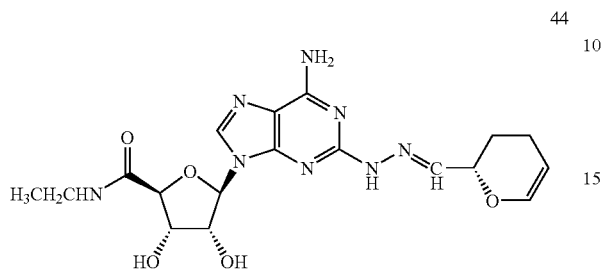

6.6 Example 6

Synthesis of Compound 50

Step A—Synthesis of 2',3'-Isopropylidene-2-cyanoadenosine-5'-carboxylic acid: A mixture of 2',3'-isopropylidene-2-cyanoadenosine(670 mg, prepared using the procedure set forth in Nair et al., *J. Am. Chem. Soc.* 111:8502-8504 (1989)), iodobenzene diacetate (1.418 g) and 2,2,6,6-tetramethylpiperidinooxy nitroxide(64 mg) were diluted with a 1:1 mixture of acetonitrile:water (8 mL) and the resultant reaction was allowed to stir at about 25° C. for about 18 hours. The reaction mixture was extracted using ethyl acetate and the organic layer was washed with water, dried over MgSO$_4$ and concentrated in vacuo. The resultant residue was suspended in methanol (10 mL) and the resultant solution was filtered, and the collected solid was dried in vacuo to provide to provide 2',3'-isopropylidene-2-cyanoadenosine-5'-carboxylic acid (340 mg). $^1$H NMR (DMSO-d$_6$, 300 MHz): 1.34 (s, 3H), 1.50 (s, 3H), 4.04-4.07 (m, 1H), 4.43-4.49 (m, 2H), 6.35 (s, 1H), 7.96 (s, 2H), 8.47 (s, 1H), 12.85 (s, 1H). MS m/z 347.4 [M+H]$^+$.

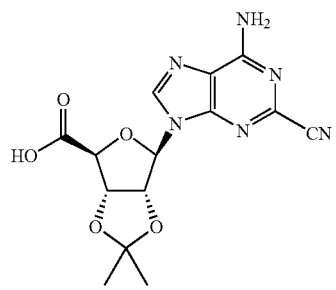

2',3'-Isopropylidene-2-cyanoadenosine-5'-carboxylic acid

Step B—Synthesis of N-Ethyl-2',3'-isopropylidene-2-cyanoadenosine-5'-carboxamide: A mixture of 2',3'-isopropylidene-2-cyanoadenosine-5'-carboxylic acid (150 mg), 1-ethyl-3-(3-dimethylaminopropyl)carbodiimide hydrochloride (1.5 eq.) in N,N-dimethylformamide (0.1 mL) and methylene chloride (5 mL) was stirred at room temperature and treated with the solution of ethylamine (2M solution in tetrahydrofuran, 10 mL). The reaction mixture was allowed to stir at room temperature for overnight and concentrated. After aqueous workup, the organic layer was dried and concentrated. The resultant residue was purified using column chromatography on silica gel column (10% methanol—methylene chloride eluent) to provide N-ethyl-2',3'-isopropylidene-2-cyanoadenosine-5'-carboxamide (35 mg). is $^1$H NMR (DMSO-d6, 300 MHz): 1.01 (t, J=7.2 Hz, 3H), 1.39 (s, 3H), 1.63 (s, 3H), 3.20-3.30 (m, 2H), 4.71 (s, 1H), 5.25-5.29 (m, 2H), 6.06 (s, 1H), 6.22 (s, 2H), 6.75 (s, 1H), 8.06 (s, 1 H). MS m/z 374.4 [M+H]$^+$.

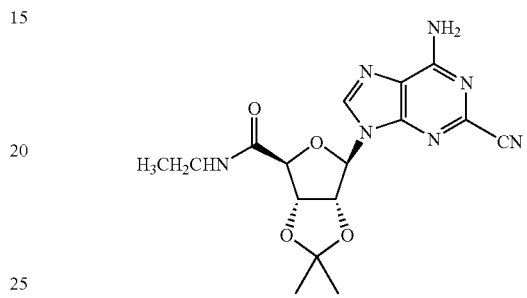

N-Ethyl-2',3'-isopropylidene-2-cyanoadenosine-5'-carboxamide

Step C—Synthesis of Compound 50: A solution of N-ethyl-2',3'-isopropylidene-2-cyanoadenosine-5'-carboxamide (34 mg) in trifluoroacetic acid (4 mL) and water (1 mL) was allowed to stir at room temperature for 1.5 hr and concentrated on rotavaporator. The residue obtained after concentration was recrystallized from ethyl acetate to provide Compound 50 (24 mg). $^1$H NMR (DMSO-d$_6$, 300 MHz): 1.02 (t, J=7.2 Hz, 3H). 3.15-3.19 (m, 2H), 4 17-4.18 (m, 1H), 4.31 (s, 1H), 4.56-4.58 (m, 1H), 5.96 (d, J=6.6 Hz. 1H), 8.06 (s, 2H), 8.25 (s, 1H), 8.70 (s, 1H). MS m/z 334.22 [M+H]$^+$.

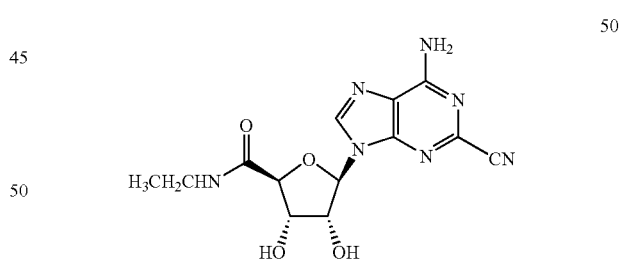

6.7 Example 7

Synthesis of Compound 52

Step A—Synthesis of 2',3'-isopropylidene-2-cyano-N$^6$-ethyladenosine-5'-carboxylic acid: Using the method set forth in Example 6, step A and substituting 2',3'-isopropylidene-2-cyano-N$^6$-ethyladenosine (prepared using the procedure set forth in Nair et al., *J. Am. Chem. Soc.* 111:8502-8504 (1989)) for 2',3'-isopropylidene-2-cyanoadenosine, 2',3'-isopropylidene-2-cyano-N$^6$-ethyladenosine-5'-carboxylic acid was prepared.

6.8 Example 8

Synthesis of Compound 53

Step A—Synthesis of 2',3'-isopropylidene-2-cyano-N⁶-ethyadenosine-5'-carboxylic acid: Using the method set forth in Example 6, step A and substituting 2',3'-isopropylidene-2-cyano-N⁶-ethyladenosine (prepared using the procedure set forth in Nair et al., m.*J. Am. Chem. Soc. II* 1:8502-8504 (1989)) for 2',3'-isopropylidene-2-cyanoadenosine, 2',3'-isopropylidene-2-cyano-N⁶-ethyladenosine-5'-carboxylic acid was prepared.

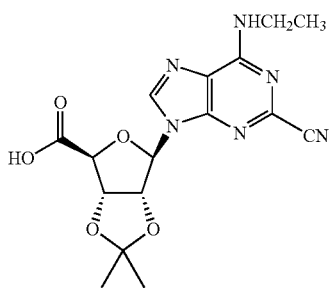

2',3'-isopropylidene-2-cyano-N⁶-ethyladenosine-5'-carboxylic acid

Step B—Synthesis of N-ethyl-2',3'-isopropylidene-2-cyano-N⁶-ethyladenosine-5'-carboxamide: Using the method set forth in Example 6, step B and substituting 2',3'-isopropylidene-2-cyano-N⁶-ethyladenosine-5'-carboxylic acid for 2',3'-isopropylidene-2-cyanoadenosine-5'-carboxylic acid, N-ethyl-2',3'-isopropylidene-2-cyano-N⁶-ethyladenosine-5'-carboxamide was prepared. MS m/z. 402.52 [M+H]⁺.

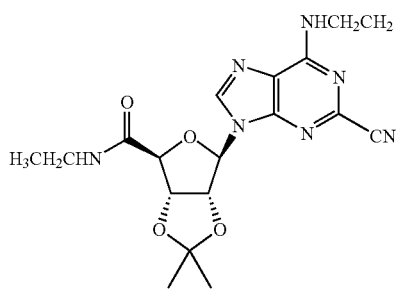

N-ethyl-2',3'-isopropylidene-2-cyano-N⁶-ethyladenosine-5'-carboxamide

Step C—Synthesis of Compound 52: Using the method set forth in Example 6, step C and substituting N-ethyl-2',3'-isopropylidene-2-cyano-N⁶-ethyladenosine-5'-carboxamide for N-ethyl-2',3'-isopropylidene-2-cyanoadenosine-5'-carboxamide, Compound 52 was prepared. MS m/z 362.38 [M+H]⁺.

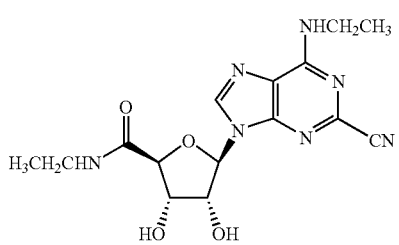

52

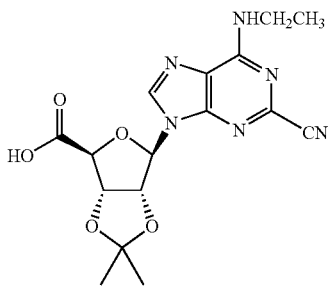

2',3'-isopropylidene-2-cyano-N⁶-ethyadenosine-5'-carboxylic acid

Step B—Synthesis of N-methyl-2',3'-isopropylidene-2-cyano-N⁶-ethyl-5'-N-carboxamide: Using the method set forth in Example 6, step B and substituting 2',3'-isopropylidene-2-cyano-N⁶-ethyladenosine-5'-carboxylic acid for 2',3'-isopropylidene-2-cyanoadenosine-5'-carboxylic acid, N-methyl-2',3'-isopropylidene-2-cyano-N⁶-ethyl-5'-N-carboxamide was prepared. MS m/z 388.25 [M+H]⁺.

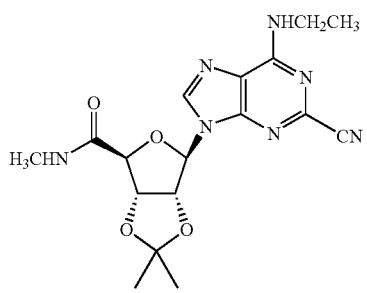

N-methyl-2',3'-isopropylidene-2-cyano-N⁶-ethyl-5'-N-carboxamide

Step C—Synthesis of Compound 53: Using the method set forth in Example 6, step C and substituting N-methyl-2',3'-isopropylidene-2-cyano-N⁶-ethyl-5'-N-carboxamide for N-ethyl-2',3'-isopropylidene-2-cyanoadenosine-5'-carboxamide, Compound 53 was prepared. MS m/z 347.95 [M+H]⁺.

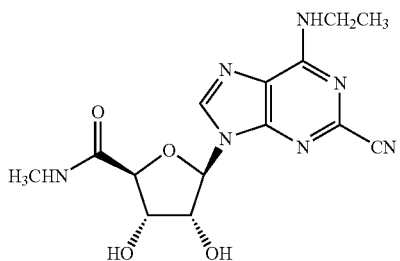

6.9 Example 9

Synthesis of Compound 54

Step A—Synthesis of 2',3'-isopropylidene-2-cyano-N⁶-methyadenosine-5'-carboxylic acid: Using the method set forth in Example 6, step A and substituting 2',3'-isopropylidene-2-cyano-N⁶-methyladenosine (prepared using the procedure set forth in Nair et al., *J. Am. Chem. Soc.* 11 1:8502-8504 (1989)) for 2',3'-isopropylidene-2-cyanoadenosine, 2',3'-isopropylidene-2-cyano-N⁶-methyladenosine-5'-carboxylic acid was prepared.

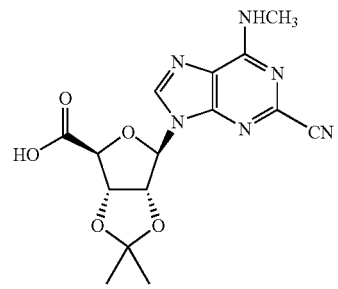

2',3'-isopropylidene-2-cyano-N⁶-methyladenosine-5'-carboxylic acid

Step B—Synthesis of N-methyl-2',3'-isopropylidene-2-cyano-N⁶-methyl-5'-N-carboxamide: Using the method set forth in Example 6, step B and substituting 2',3'-isopropylidene-2-cyano-N⁶-methyladenosine-5'-carboxylic acid for 2',3'-isopropylidene-2-cyanoadenosine-5'-carboxylic acid, N-ethyl-2',3'-isopropylidene-2-cyano-N⁶-methyl-5'-N-carboxamide was prepared. MS m/z 388.25 [M+H]⁺.

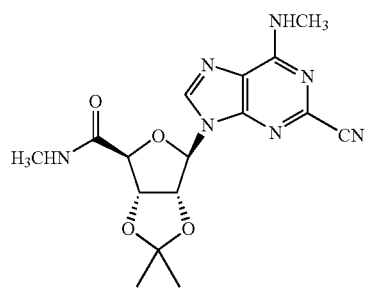

N-methyl-2',3'-isopropylidene-2-cyano-N⁶-methyl-5'-N-carboxamide

Step C—Synthesis of Compound 54: Using the method set forth in Example 5, step C and substituting N-ethyl-2',3'-isopropylidene-2-cyano-N⁶-methyl-5'-N-carboxamide for N-ethyl-2',3'-isopropylidene-2-cyanoadenosine-5'-carboxamide, Compound 54 was prepared. MS m/z 347.95 [M+H]⁺.

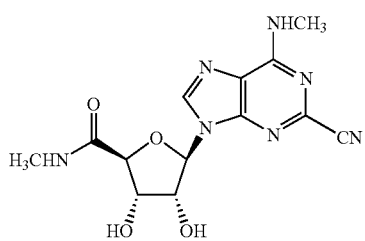

6.10 Example 10

Cell Culture and Membrane Preparation for Human Adenosine $A_{2A}$ or A3 Receptor-Binding Studies CHO cells stably transfected with either human adenosine $A_{2A}$ receptor or human adenosine $A_3$ receptor are grown and maintained in Dulbecco's Modified Eagles Medium with nutrient mixture F12 (DMEM/F12) without nucleosides, containing 10% fetal calf serum, penicillin (100 U/mL), streptomycin (100 µg/mL), L-glutamine (2 mM) and Geneticin (G-418, 0.2 mg/mL; $A_{2B}$, 0.5 mg/mL) at 37° C. in 5% $CO_2$/95% air. Cells are then split 2 or 3 times weekly at a ratio of between 1:5 and 1:20.

Membranes for radioligand binding experiments are prepared from fresh or frozen cells as described in Klotz et al., *Naunyn-Schmiedeberg's Arch. Pharmacol.*, 357:1-9 (1998). The cell suspension is then homogenized in ice-cold hypotonic buffer (5 mM Tris/HCl, 2 mM ethylenediamine-N,N-N'N'-tetraacetic acid, pH 7.4) and the homogenate is spun for 10 minutes (4° C.) at 1,000 g. The membranes are then sedimented from the supernatant for 30 minutes at 100,000 g and resuspended in 50 mM Tris/HCl buffer pH 7.4 (for $A_3$ adenosine receptors: 50 mM Tris/HCl, 10 mM $MgCl_2$, 1 mM EDTA, pH 8.25), frozen in liquid nitrogen at a protein concentration of 1-3 mg/mL and stored at –80° C.

6.11 Example 11

Anti-inflammatory Effects of the Purine Derivatives

Effect of the Purine Deriviatives on Induction of Endotoxic Shock

For cytokine production, Male BALB/c mice (6-8 weeks of age) are treated with a Purine Derivative (oral administration at 0.03 mg/kg) orally by gavage 30 minutes before being subjected to LPS (1 mg/kg i.p.) for 90 minutes. A blood sample is then taken and serum obtained for analysis. Serum is diluted 1:5 prior to being assayed for cytokines using species-specific ELISA kits (R & D Systems) for the chemokine MIP-1α and the cytokine TNF-α levels, which are expressed as pg/ml.

6.12 Example 12

Effect of the Purine Derivatives on Function Recovery after Global Ischemia/Reperfusion Heart Perfusion Male Sprague-Dawley rats (each having a body weight of 250 to 300 g) are heparinized using sodium heparin (1,000 U/kg i.p.), followed 10 minutes later by introduction of anesthesia via intraperitoneal administration of sodium pentobarbital (40 mg/kg). Once the subject is anesthetized, the thorax is opened, and the heart is rapidly removed and perfused through the ascending aorta using Krebs-Ringer buffer consisting of NaCl (118 mmol/liter), KCl (4.75 mmol/liter), $KH_2PO_4$ (1.18 mmol/liter), $MgSO_4$ (1.18 mmol/liter), $CaCl_2$ (2.5 mmol/liter), $NaHCO_3$ (25 mmol/liter), and glucose (11 mmol/liter). A mixture of 95% $O_2$ and 5% $CO_2$ at 37° C. is then bubbled through the perfusate. The heart is initially perfused at a constant pressure of 70 mm Hg. About 10 minutes after the constant pressure perfusion, perfusion is switched to constant flow perfusion achieved using a microtube pump. The perfusion pressure is maintained at the same level of constant pressure perfusion by adjusting flow rate. Once the flow rate is determined, it is maintained throughout the experiment. The hearts are stimulated by rectangular pulses at a rate of 5 Hz and 2-millisecond duration and twice the diastolic threshold, delivered from a stimulus isolation unit (ADInstruments Ltd, Australia).

Effect of the Purine Derivatives on Function Recovery after Ischemia/Reperfusion Rat hearts are initially perfused at a constant pressure of 70 mm Hg using the procedure described above under the heading "heart perfusion." After a 20 minute stabilization period, the hearts are subjected to 30 minute no-flow ischemia followed by 40 minute reperfusion. The Purine Derivatives are infused in hearts for 10 minutes prior to induction of ischemia. Bipolar epicardial electrocardiogram (ECG) is recorded by placing two electrodes on the surface of right appendage and apex. A stainless steel cannula is used as indifferent electrode. After a 20-minute equilibration period, regional ischemia is induced by ligation of the left anterior descending (LAD) coronary artery, and the ligature is released 30 minutes after occlusion. The hearts are then subject to 40 minutes of reperfusion A Purine Derivative is applied interperfusate 10 minutes before LAD ligation and is present during LAD ligation. The Purine Derivatives are typically tested in this model at 10, 30 and 100 pM concentrations.

To assess contractile function, a microtip catheter transducer (Millar Instruments Inc., Houston, Tex.) is inserted directly into the left ventricular cavity and data are collected using a PowerLab data acquisition system (ADInstruments Ltd, Australia) in conjunction with a Macintosh computer, and analyzed using Chart.3 computer package. Coronary perfusion pressure (CPP), left ventricular systolic pressures (LVSP), left ventricular end diastolic pressures (LVEDP), maximal rates of development of left ventricular pressure ($+dP/dt_{max}$, $-dP/dt_{min}$) can be measured using this method and. Left ventricular developed pressure (LVDP) can be calculated as the difference between the systolic and diastolic pressure.

6.13 Example 13

Effect of the Purine Derivatives on Wound Healing

Effect of the Purine Derivatives on Endothelial Cell and Fibroblast Migration

In vitro wound assays can be performed as described by Shleef et al., *Tissue Cell* 14:629-636 (1982). Cells, for example, human umbilical or saphenous vein endothelial cells, dermal fibroblasts, etc., are cultured in Medium 199 containing 10% fetal bovine serum until they form confluent monolayers, for example, in 12 well culture plates. The confluent monolayers are treated with mitomycin C (10.mu.g/ml) and 60 minutes later are wounded using a razor blade. The wounded cells are rinsed several times with saline and a predetermined amount of a Purine Derivative is then added to replicate wells. Cell migration into the wound is assessed at various times thereafter using phase contrast microscopy with an inverted microscope. Quantitation may be performed by aligning the original edge of the wound with the "0" line on a 10×10 grid-reticle and the counting the number of cells in each of the 10 rows defined by the reticle.

6.14 Example 14

Effect of Compound 34 on Asthma-Associated Inflammation

Aerosol Exposure and Bronchoalveolar Lavage

Four-week old male, viral-antibody-free BALB/c mice (Jackson Laboratory, Bar Harbor, Me.) were intraperitoneally immunized with 10 μg ovalbumin ("OVA," Grade III, Sigma Chemical Co., St. Louis, Mo.) and 1 mg alum (diluted from 2% Alhydrogel; Accurate Sci. Corp., Westbury, N.Y.) in 0.5 mL phosphate-buffered saline ("PBS") on days 0 and 7. Control mice received 1 mg alum in PBS solution on days 0 and 7.

On day 14, both immunized mice and control mice received a single aerosol exposure to 3% OVA (in PBS) for 30 minutes, followed by intraperitoneal administration of Compound 34 (5 μg per mouse in 0.2 mL buffer solution). About 18 hours after treatment, the mice were sacrificed and bronchoalveolar lavage ("BAL") was performed on their lungs. The fluid obtained from the mice via the BAL procedure was analyzed and the inflammatory cell counts and level of inflammatory mediators in the fluid samples was measured as described in Virag et al., *Med. Sci. Monit.* 10:BR77-83 (2004). Results indicate that inflammatory cell infiltration into the BAL fluid was reduced by 70±19% ($p<0.01$) in the treated animals vs. the control animals. As shown by the data in Table 3, animals treated with Compound 34 also showed reduced MIP-1α levels (74% reduction relative to control), reduced TNF-α levels (30% reduction relative to control), and reduced white blood cell counts (70% reduction relative to control).

TABLE 3

Effect of Compound 34 on TNF-α and MIP-1 levels in BALB-C Mice

|  | MIP-1α (pg/mL) | TNF-α (pg/mL) | White Blood Cells (cells/mL) |
|---|---|---|---|
| Untreated mice | 58 ± 19 | 81 ± 27 | 2.76 ± 1.3 |
| Mice treated with Compound 34 | 15 ± 5 | 56 ± 18 | 0.81 ± 0.5 |

Accordingly, Compound 34, an illustrative Purine Derivative, is useful for the treatment of asthma-associated inflammation in a subject.

6.15 Example 15

Effect of Compound 24 on Asthma-Associated Inflammation

Aerosol Exposure and Bronchoalveolar Lavage

Four-week old male, viral-antibody-free BALB/c mice (Jackson Laboratory, Bar Harbor, Me.) were intraperitoneally immunized with 10 μg ovalbumin ("OVA," Grade III, Sigma Chemical Co., St. Louis, Mo.) and 1 mg alum (diluted from 2% Alhydrogel; Accurate Sci. Corp., Westbury, N.Y.) in 0.5 mL phosphate-buffered saline ("PBS") on days 0 and 7. Control mice received 1 mg alum in PBS solution on days 0 and 7.

On day 14, both immunized mice and control mice received a single aerosol exposure to 3% OVA (in PBS) for 30 minutes, followed by intraperitoneal administration of Compound 24 (5 μg per mouse in 0.2 mL buffer solution). About 18 hours after treatment, the mice were sacrificed and bronchoalveolar lavage ("BAL") was performed on their lungs. The fluid obtained from the mice via the BAL procedure was analyzed and the inflammatory cell counts and level of inflammatory mediators in the fluid samples was measured as described in Virag et al., *Med. Sci. Monit.* 10:BR77-83 (2004). Results, reported in FIG. 1 and FIG. 2, indicate animals treated with Compound 24 also showed reduced MIP-1α levels (see FIG. 1) and reduced TNF-α levels (see FIG. 2) relative to control animals.

Accordingly, Compound 24, an illustrative Purine Derivative, is useful for the treatment of asthma-associated inflammation in a subject.

6.16 Example 16

Effect of Compound 43 on TPA-Induced Dermatitis

Induction of Dermatitis

Dermatitis was induced in the right ear of unanesthetized mice via the topical application of 12-O-tetradecanoylphorbol-13-acetate (TPA) (10 μL, 1% in DMSO) on both the inner and outer surfaces of the right ear. The left ear of each mouse had only vehicle (DMSO, 10 μL) topically applied on both the inner and outer surfaces.

Treatment of Dermatitis-Induced Ear with Compound 43

Immediately after application of TPA, the mice were topically treated on the inner and outer surfaces of their right ear only with either: (1) Compound 43 (10 μL, 0.1% in normal saline), (2) Compound 43 (10 μL, 0.3% in normal saline), or (3) normal saline (10 μL).

Six hours after the application of Compound 43 or normal saline, the animals were euthanized using $CO_2$ asphyxiation and a ¼ inch biopsy of both the left and right ear was taken and weighed. The biopsy samples were then analyzed for myloperoxidase (MPO) activity as a marker of neutrophil infiltration using standard methods.

The data in Table 4 show that the elevated weight in the right ear caused by the TPA-induced dermatitis was reduced in a dose-dependent fashion in the animals treated with Compound 43 compared to control animals (i.e., animals receiving normal saline only).

TABLE 4

Effect of Compound 43 on Ear Weight

| Treatment | n | Right ear (treated) Mean Weight (mg) | SEM | Left ear (untreated) Mean Weight (mg) | SEM | Difference mg | SEM |
|---|---|---|---|---|---|---|---|
| Compound 43 (0.3%) | 10 | 13.6 | 1.0 | 13.5 | 0.6 | 0.1 | 1.3 |
| Compound 43 (0.1%) | 10 | 17.7 | 1.2 | 12.4 | 0.5 | 5.3 | 1.1 |
| Normal saline | 10 | 20.2 | 0.3 | 10.1 | 0.4 | 10.1 | 0.5 |
| Untreated | 10 | 21.9 | 0.5 | 11.4 | 0.7 | 10.6 | 0.7 | n = number of animals
Untreated = animals receiving neither Compound 43 nor normal saline after TPA application
SEM = standard error of mean The data in Table 5 show that the administration of Compound 43 decreased MPO levels in the treated right ears. This is indicative of a reduction in inflammation in the animals treated with Compound 43 compared to control animals treated with only TPA and normal saline.

TABLE 5

Effect of Compound 43 on Myeloperoxidase (MPO) Levels

| Treatment | n | Right ear (treated) MPO ug/sample | SEM | Left ear (untreated) MPO ug/sample | SEM | Difference | SEM |
|---|---|---|---|---|---|---|---|
| Compound 43 (0.3%) | 9 | 3.34 | 0.69 | 1.69 | 0.17 | 1.65 | 0.62 |
| Compound 43 (0.1%) | 13 | 1.04 | 0.13 | 0.37 | 0.06 | 0.67 | 0.11 |
| Normal saline | 9 | 18.4 | 2.45 | 1.59 | 0.09 | 16.8 | 2.43 |
| Untreated | 12 | 2.84 | 0.36 | 0.48 | 0.04 | 2.36 | 0.38 | n = number of animals
Untreated = animals receiving neither Compound 43 nor normal saline after TPA application
SEM = standard error of mean Accordingly, Compound 43, an illustrative Purine Derivative, is useful for the treatment of dermatitis in a subject.

6.17 Example 17

Effect of Compound 54 on Dextran Sodium Sulfate-Induced Colitis

Colitis was induced in Swiss Webster mice by administration of dextran sodium sulfate (DSS) (5%, dissolved in distilled water, molecular weight 30-40 kDa) ad libitum for a total period of seven days. During this seven-day period, and concomitant with the administration of DSS, the mice were separately administered Compound 54 twice daily by gavage at a total daily dose of 0.1 mg/kg/day, 0.3 mg/kg/day or 1 mg/kg/day. At the end of the seventh day of administration of both DSS and Compound 54, the mice were euthanized and their colon was removed, measured, visually analyzed and colon biopsy samples were analyzed for malondialdehyde (MDA) and myeloperoxidase (MPO) levels.

The data in Table 6 indicate that administration of Compound 54 (at a dose of 0.1 mg/kg/day, 0.3 mg/kg/day or 1 mg/kg/day) protected against colon shortening and lowered the levels of MDA and MPO in a dose-dependent fashion compared to animals treated with vehicle. Decreased levels of MDA and MPO are associated with a decrease in inflammation and colon damage in an animal.

TABLE 6

Effect of Compound 54 on Colon Length, MPO levels and MDA levels

| | vehicle | 0.1 mg/ml | 0.3 mg/ml | 1 mg/ml |
|---|---|---|---|---|
| Colon Length (cm) | 3.97 | 4.95 | 5.51 | 5.87 |
| SEM | 0.18 | 0.32 | 0.24 | 0.31 |
| visual score (1-4) | 2 | 1.5 | 1.2 | 1.4 |
| SEM | 0.23 | 0.19 | 0.21 | 0.17 |
| MDA (nmol/mg protein) | 8.7 | 7.4 | 7.4 | 4.4 |
| SEM | 1.0 | 1.0 | 0.85 | 0.56 |
| MPO (mμ/mg protein) | 209 | 345 | 138 | 30 |
| SEM | 44 | 18 | 62 | 15 |

SD = standard deviation
SEM = standard error of mean
The term "visual score" refers to a visual assessment of colon damage with a score of 1 meaning that no damage was seen and a score of 4 meaning that extensive damage was seen.

Accordingly, Compound 54, an illustrative Purine Derivative, is useful for the treatment of colitis in a subject.

6.18 Example 18

Effect of Compound 54 on an LPS-Induced Chemokine and Cytokine Response

Male BALB/c mice were intraperitoneally administered Compound 54 (at a dose of either 0.3 mg/kg or 1.0 mg/kg) over a 30-minute period. Lipopolysaccharide (LPS) was then administered intraperitoneally at a dose of 1 mg/kg. Ninety minutes after LPS administration, serum was collected and the levels of MIP-1α and TNF-α were analyzed using specific ELISA.

The data shown in Table 7 indicate that Compound 54 dose-dependently reduces an LPS-induced increase in TNF-α and MIP-1α and as such, indicate that Compound 54 attenuates an LPS-induced inflammatory response.

TABLE 7

Affect of Compound 54 on Serum TNF-α and MIP-1α levels

| | LPS | Compound 54 (0.3 mg/kg) | Compound 54 (1.0 mg/kg) |
|---|---|---|---|
| Serum TNF-α | | | |
| mean(pg/ml) | 9741 | 5733 | 3727 |
| SD | 2022 | 2162 | 1456 |
| SEM | 715 | 764 | 514 |
| Serum MIP-1α | | | |
| mean(pg/ml) | 4150 | 4298 | 3906 |
| SD | 429 | 574 | 651 |
| SEM | 162 | 202 | 230 |

SD = standard deviation
SEM = standard error of mean

Accordingly, Compound 54, an illustrative Purine Derivative, is useful for the treatment of inflammatory disease in a subject.

6.19 Example 19

Effect of Compound 34 on an LPS-Induced Chemokine and Cytokine Response

Male BALB/c mice were intraperitoneally administered Compound 34 (at a dose of 0.03 mg/kg or 0.1 mg/kg) over a 30 minute period. Lipopolysaccharide (LPS) was then administered intraperitoneally at a dose of 1 mg/kg. Ninety minutes after LPS administration, serum was collected and the levels of MIP-1α and TNF-α were analyzed using specific ELISA.

The data shown in Table 8 indicate that Compound 34 dose-dependently reduces an LPS-induced increase in TNF-α and MIP-1α and as such, indicate that Compound 34 attenuates an LPS-induced inflammatory response.

TABLE 8

Affect of Compound 34 on Serum TNF-α and MIP-1α levels

| | LPS | Compound 34 (0.03 mg/kg) | Compound 34 (0.1 mg/kg) |
|---|---|---|---|
| Serum TNF-α | | | |
| mean(pg/ml) | 1949 | 814 | 552 |
| SD | 1077 | 578 | 368 |
| SEM | 380 | 204 | 130 |
| Serum MIP-1α | | | |
| mean(pg/ml) | 2544 | 1182 | 981 |
| SD | 916 | 183 | 313 |
| SEM | 323 | 64 | 110 |

SEM = standard error of mean

Accordingly, Compound 34, an illustrative Purine Derivative, is useful for the treatment of inflammatory disease in a subject.

The present invention is not to be limited in scope by the specific embodiments disclosed in the examples which are intended as illustrations of a few aspects of the invention and any embodiments that are functionally equivalent are within the scope of this invention.

All references cited herein are incorporated by reference in their entirety.

What is claimed is:

1. A compound of the following formula:

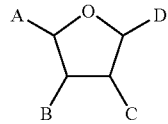

(Id)

or a pharmaceutically acceptable salt thereof,
wherein

A is —C(O)NHR$^3$;
B and C are —OH;
D is

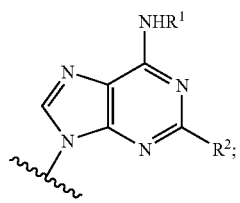

A and B are trans with respect to each other;
B and C are cis with respect to each other;
C and D are cis or trans with respect to each other;
R$^1$ is —H or —C$_1$-C$_{10}$ alkyl;
R$^2$ is —CN; and
R$^3$ is —C$_1$-C$_{10}$ alkyl.

2. The compound of claim 1, wherein R$^1$ is —H.
3. The compound of claim 1, wherein R$^1$ is —C$_1$-C$_{10}$ alkyl.
4. The compound of claim 1, wherein R$^3$ is methyl.
5. The compound of claim 1, wherein R$^3$ is ethyl.
6. The compound of claim 1 having the structure:

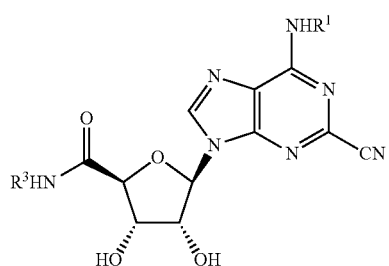

(Id')

or a pharmaceutically acceptable salt thereof;
wherein

R$^1$ is —H, —CH$_3$, or —CH$_2$CH$_3$; and
R$^3$ is —CH$_3$ or —CH$_2$CH$_3$.

7. The compound of claim 1, wherein said compound is selected from the group consisting of:

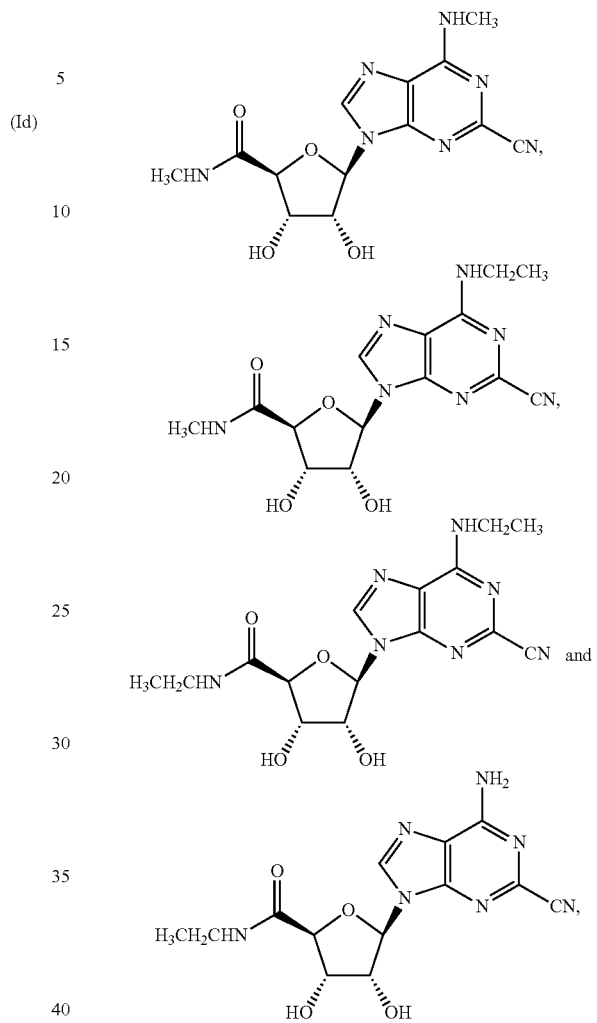

or a pharmaceutically acceptable salt thereof.

8. A therapeutic composition comprising an effective amount of the compound or a pharmaceutically acceptable salt of the compound of claim 1 and a physiologically acceptable vehicle.

9. A compound having the formula:

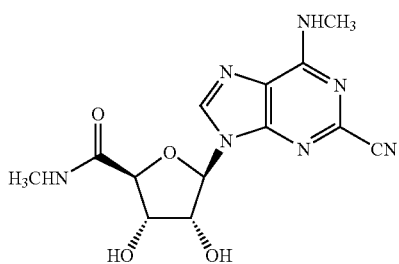

or a pharmaceutically acceptable salt thereof.

10. A therapeutic composition comprising an effective amount of the compound or a pharmaceutically acceptable salt of the compound of claim 9 and a physiologically acceptable vehicle.

* * * * *